(12) United States Patent
Homcy et al.

(10) Patent No.: US 6,333,447 B1
(45) Date of Patent: *Dec. 25, 2001

(54) TRANSGENIC MODEL OF HEART FAILURE

(75) Inventors: Charles C. Homcy, San Francisco, CA (US); Stephen F. Vatner, Wayland, MA (US); Thomas Wagner, Albany, OH (US); Yoshihiro Ishikawa, Brookline, MA (US)

(73) Assignees: The General Hospital Corporation, Boston, MA (US); Ohio University, Athens, OH (US); The Presidents and Fellows of Harvard College, Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/627,788

(22) Filed: Mar. 29, 1996

(51) Int. Cl.[7] .......................... C12N 15/09; C12N 15/63; C12N 15/00; C12N 5/00

(52) U.S. Cl. .................................. 800/18; 800/9; 800/13; 800/14; 800/17; 800/21; 800/25; 435/455; 435/320.1; 424/9.2

(58) Field of Search ............................. 800/2, DIG. 1–4, 800/9, 13, 14, 17, 21, 25, 18; 435/172.3, 455, 320.1; 424/9.1, 9.2

(56) References Cited

U.S. PATENT DOCUMENTS

| | | | |
|---|---|---|---|
| 4,736,866 | 4/1988 | Leder et al. | 800/1 |
| 5,162,215 | * 11/1992 | Bosselman et al. | 435/172.3 |
| 5,175,385 | 12/1992 | Wagner et al. | 800/2 |
| 5,545,808 | * 8/1996 | Hew et al. | 800/2 |

FOREIGN PATENT DOCUMENTS

| | | | |
|---|---|---|---|
| WO 88/10304 | 12/1988 | (WO) | C12N/15/00 |
| WO 91/02793 | 3/1991 | (WO) | C12N/15/00 |

OTHER PUBLICATIONS

Gaudin et al., Journal of Clinical Investigation, vol. 95, pp. 1676–1683, Apr. 1995.*

The Genomics Lexicon, http://genomics.phrma.org/lexicon/o.html, 2001.*

Krimpenfort et al. Generation of Transgenic Dairy Cattle Using 'In Vitro' Embryo Production. Bio/Technology, vol. 9, pp. 844–847, Sep. 1991.*

Mullins et al. Transgenesis in nonmurine species. Hypertension. vol. 22, No. 4, pp. 630–633, Oct. 1993.*

Wall R. J. Transgenic Livestock: Progess and prospects for the future. Theriogenology. vol. 45, pp. 57–68, 1996.*

Houdebine, L. M. Production of pharmaceutical proteins from transgenic animals. J of Biotech., vol. 34, pp. 269–287, 1994.*

Ishikawa et al. Characterization of Gs coupling to beta–adrenergic receptor and adenylyl cyclase in the hearts of transgenic mice overexpressing gs–alpha. Keystone symposium Feb. 6–13, 1994 and J. of Cellular Biochemistry, vol. 18B p. 220, I 138, Feb. 6, 1994.*

Gaudin et al. Overexpression of GS–alpha protein in the heart of transgenic mice. Meeting, Wash. D.C. Apr. 30 thru May 3, 1993 and Clin. Res., vol. 41, 145A, Apr. 30, 1993.*

A.C. Guyton (1982) *Human Physiology and Mechanisms of Disease,* Third Edition, W. B. Saunders Co., Philadelphia, PA, p. 205.

*Manual of Medical Therapeutics* (1989) Twenty–Sixth Edition, Little, Brown & Co., Boston (W. C. Dunagan and M. L. Ridner, eds.), pp. 106–109.

K. Kiuchi et al. (1993) "Myocardial β–Adrenergic receptor Function During The Development of Facing–Induced Heart Failure," *J. Clin. Invest.* 91:907–14.

*Goodman and Gilman's The Pharmacological Basis of Therapeutics* (1990) Eighth Edition, Pergamon Press, Inc. (Alfred Goodman Gilman et al., eds.), pp. 88–90.

D. E. Vatner et al. (1989) "Chronic Norepinephrine Elicits Desensitization by Uncoupling the β–Receptor," *J. Clin. Invest.* 84:1741–48.

M.R. Bristow et al. (1982) "Decreased Catecholamine Sensitivity and β–Adrenergic–Receptor Density In Failing Human Hearts," *N. Eng. J. Med.* 307:205–11.

W.F. Ganong (1987) *Review of Medical Physiology,* Thirteenth Edition, Appleton & Lange, CN, pp. 534–535.

R.A. Kloner and V. J. Dzau (1990) *Heart Failure,* Chapter 23 in *The Guide to Cardiology,* Second Edition, R. A. Kloner (ed.) Le Jacq Communications, p. 359.

L. Y. Young et al. (1989) *Handbook of Applied Therapeutics,* Applied Therapeutics, Inc., Vancouver, WA, pp. 7.1–7.12 and 9.1–9.10.

Michiels, et al., (1994) "Ongogenic Potential of Guanine Nucleotide Stimulatory Factor α Subunit in Thyroid Glands of Transgenic Mice," *Proc. Natl. Acad. Sci. USA* 91:10488.

Ma, et al. (1994) "Constitutively Active Stimulatory G–Protein $\alpha_s$ in β–Cells of Transgenic Mice Causes Counter–regulation of the Increased Adenosine 3',5'–Monophospate and Insulin Secretion." *Endocrinol.* 134:42.

(List continued on next page.)

*Primary Examiner*—Jill D. Martin
(74) *Attorney, Agent, or Firm*—Medlen & Carroll LLP

(57) ABSTRACT

The present invention relates to transgenic models of heart failure and, more particularly, to transgenic animals and methods for testing the usefulness of chemical compounds in treating or preventing heart failure. A transgenic mouse was developed wherein $G_{s\alpha}$ is selectively overexpressed approximately three-fold in the heart. Although steady state adenylyl cyclase activities are not altered, both the percent of agonist high affinity β-adrenergic receptors as well as the rate of catalyst activation are increased. In addition, physiological and pathological studies revealed that chronically-facilitated sympathetic stimulation causes adverse cardiac effects.

24 Claims, 17 Drawing Sheets

(2 of 17 Drawing Sheet(s) Filed in Color)

OTHER PUBLICATIONS

Brinster, et al. (1985), "Factors affecting the efficiency of introducing foreign DNA into Mice by Microinjecting eggs," *Proc. Natl. Acad. Sci. USA* 82:4438–4442.

Janenich (1976) "Germ line integration and Mendelian transmission of the exogenous Moloney leukemia virus, " *Proc. Natl. Acad. Sci. USA* 73:1260–1264.

Jahner, D. et al. (1985) "Insertion of the bacterial gpt gene into the germ line of mice by retroviral infection," *Proc. Natl. Acad Sci. USA* 82:6927–6931.

Van der Putten, et al. (1985) "Efficient insertion of genes into the mouse germ line via retroviral vectors," *Proc. Natl. Acad Sci. USA* 82:6148–6152.

Stewart, et al. (1987) "Expression of retroviral vectors in transgenic mice obtained by embryo infection," *EMBO J.* 6:383–388.

Jahner, D. et al. (1982) "De novo methylation and expression of retroviral genomes during mouse embryogenesis," *Nature* 298:623–628.

Evans, et al. (1981) "Establishment in culture of pluripotential cells from mouse embryos," *Nature* 292:154–156.

Bradley, et al. (1984) "Formation of germ–line chimaeras from embryo–derived teratocarcinoma cell lines," *Nature* 309:255–258.

Gossler, et al. (1986) "Transgenesis by means of blastocyst-derived embryonic stem cell lines," *Proc. Acad. Sci. USA* 83:9065–9069.

Robertson, et al. (1986) "Germ–line transmission of genes introduced into cultured pluripotential cells by retroviral vector," *Nature* 322:445–448.

Jaenisch (1988) "Transgenic Animals," *Science* 240:1468–1474.

C. J. Homcy et al. (1991) "β–Adrenergic Receptor Regulation in the Heart in Pathophysiologic States: Abnormal Adrenergic Responsiveness in Cardiac Disease," *Annu. Rev. Physiol.* 53:137–59.

A.G. Gilman (1987) "G Proteins: Transduceers of Receptor–Generated Signals," *Annu. Rev. Biochem.* 56:615–49.

D. E. Vatner et al. (1984) "Effects of Pressure Overload Left Ventricular Hypertrophy on β–Adrenergic Receptors, and Responsiveness to Catecholamines," *J. Clin. Invest.* 73:1473–82.

L. Chen et al. (1991) "Decreased $G_{sa}$ myna Levels Accompanying the Fall in $G_s$ and Adenylyl Cyclase Activities in Compensated Left Ventricular Hypertrophy," *J. Clin. Invest.* 87:293–98.

D. E. Vatner et al. (1985) "Loss of High Affinity Cardiac Beta Adrenergic Receptors in Dogs with Heart Failure," *J. Clin. Invest.* 76:2259–64.

J. P. Longabaugh et al. (1988) "Decreased Stimulatory Guanosine Triphosphate Binding Protein in Dogs with Pressure–Overload Left Ventricular Failure," *J. Clin. Invest.* 81:420–24.

E. E. Susanni et al. (1989) "One Hour of Myocardial Ischemia Decreases the Activity of the Stimulatory Guanine–Nucleotide Regulatory Protein $G_s$," *Circ. Res.* 65:1145–50.

A. A. Alousi et al. (1991) "Stoichiometry of Receptor–$G_s$–adenylate Cyclase Interactions," *FASEB* (Fed. Am. Soc. Exp. Biol.) J. 5:2300–03.

J. Rottman et al. (1990) "Myosin Heavy Chain Gene Expression: Interplay of Cis and Trans Factors Determines Hormonal and Tissue Specificity," in *The Dynamic State of Muscle Fibers* (D. Pett, ed.) Waltyer de Gruyter, New York, pp. 3–16.

J. Gulick et al. (1991) "Isolation and Characterization of the Mouse Cardiac Myosin Heavy Chain Genes," *J. Biol. Chem.* 266:9180–85.

A. Subramaniam et al. (1991) "Tissue Specific Regulation of the α–Myosin Heavy Chain Gene Promoter in Transgenic Mice," *J. Biol. Chem.* 266:24613–20.

R. Al–Shawi et al. (1990) "Expression of a Foreign Gene in a Line of Transgenic Mice Is Modulated by a Chromosomal Position Effect," *Mol. Cell Biol.* 10:1192–98.

E. B. Katz et al. (1992) "Cardiomyocyte Proliferation in Mice Expressing α–cardiac Myosin Heavy Chain–SV40 T–antigen Transgene," *Am. J. Physiol.* 262:H1867–H1876.

D. M. F. Cooper et al. (1995) "Adenylyl Cyclases and the Interaction Between Calcium and cAMP Signalling," *Nature* 374:421–24.

C. A. Milano et al. (1994) "Enhanced Myocardial Function in Transgenic Mice Overexpressing the $β_2$–Adrenergic Receptor," *Science* 264:582–86.

Dies et al. (1986) "Intermittent Dobutamine In Ambulatory Outpatients With Chronic Cardiac Failure," *Circ.* (Abstract) 74:11–38.

M. J. Krell et al. (1986) "Intermittent, ambulatory dobutamine infusions in patients with severe congetive heart failure," *Am. Heart J.* 112:787–92.

H. Lambertz et al. (1984) "Long–term hemodynamic effects of prenalterol in patients with severe congestive heart failure," *Circ.* 69:298–305.

Ryden et al. (1990) "Xamoterol in Severe Heart Failure," *Lancet* 336:1–6.

M. Packer et al. (1991) "Effect of Oral Milrinone on Mortality in Severe Chronic Heart Failure," *N. Engl. J. Med.* 325:1468–75.

S.N. Heilbrunn et al. (1989) "Increased β–Receptor Density and Improved Hemodynamic Response to Catecholamine Stimulation During Long–term Metoprolol Therapy in Heart Failure From Dilated Cardiomyopathy," *Circ.* 79:483–90.

F. Waagstein et al. (1989) "Long–term β–Blockade in Dilated Cardiomyopathy," *Circ.* 80:551–63.

M. Metra et al. (1994) "Effects of Short– and Long–Term Carvedilol Administration on Rest and Exercise Hemodynamic Variables, Exercise Capacity and Clinical Conditions in Patients with Idiopathic Dilated Cardiomyopathy," *J. Am. Coll. Cardiol.* 24:1678–87.

S. L. Olsen et al. (1995) "Carvedilol Improves Left Ventricular Function and Symptoms in Chronic Heart Failure: A Double–Blind Randomized Study," *J. Am. Coll. Cardiol.* 25:1225–31.

V. Mahdavi et al. (1984) "Cardiac α– and β–myosin Heavy Chain Genes are Organized in Tandem," *Proc. Natl. Acad. Sci. USA* 81:2626.

Y. Isikawa et al. (1990) "Alternative Promoter and 5' Exon Generate a Novel $G_{sa}$ myna," *J. Biol. Chem.* 265:8458–8462.

Kozasa et al (1988) "Isolation and Characterization of the Human $G_{sa}$ Gene," *Proc. Natl. Acad. Sci. USA* 85:2081.

R. L. Brinster et al. (1988) "Introns increase transcriptional efficiency in transgenic mice," *Proc. Natl. Acad. Sci. USA* 85:836–40.

*Current Protocols in Molecular Biology*, Ausubel, et al., eds., John Wiley and Sons, Inc. (1994) pp. 2.6.1–2.6.3.

Wagner et al. (1981) "Microinjection of a Rabbit β–globin Gene Into Zygotes and its Subsequent Expression in Adult Mice and their Offspring," *Proc. Natl. Acad. Sci. USA* 78:6376–80.

Gonzalez et al (1985) "Variation Among Human 28S Ribosomal RNA Genes," *Proc. Natl. Acad. Sci. USA* 82:7666–7670.

Bradford (1976) "A Rapid and Sensitive Method for the Quantitation of Microgram Quantities of Protein Utilizing the Principle of Protein–Dye Binding," *Anal. Biochem.* 72:248–54.

Liao and Homcy (1992) "Specific Receptor–Guanine Nucleotide Binding Protein Interaction Mediates the Release of Endothelium–Derived Relaxing Factor," *Circ. Res.* 70:1018–26.

Kozak (1986) "Point Mutations Define a Sequence Flanking the AUG Initiator Codon That Modulates Translation by Eukaryotic Ribosomes," *Cell* 44:283–92.

Kurosaki et al. (1991) "A subunit common to an IgG Fc receptor and the T–cell receptor mediates assembly through different interactions," *Proc. Natl. Acad. Sci. USA* 88:3837–41.

Linder et al. (1993) "Lipid modifications of G proteins, α subunits are palmitoylated," *Proc. Natl. Acad. Sci. USA* 90:3675–79.

Taussig et al. (1993) "Inhibition of Adenylyl Cyclase by $G_{i\alpha}$," *Science* 261:218–21.

Lewis and Bourne (1992) "Activation of the α Subunit of $G_s$ in Intact Cells Alters Its Abundance, Rate of Degradation, and Membrane Avidity," *J. Cell Biol.* 119:1297–1307.

P. C. Sternweis and A. G. Gilman (1979) "Reconstitution of Catecholamine–Sensitive Adenylate Cyclase," *J. Biol. Chem.* 254:3333–40.

E. M. Ross et al. (1977) "Relationship Between the β–Adrenergic Receptor and Adenylate Cyclase," *J. Biol. Chem.* 252:5761–75.

Longabaugh et al. (1988) "Decreased Stimulatory Guanosine Triphosphate Binding Protein in Dogs with Pressure–Overload Left Ventricular Failure," *J. Clin. Invest.* 81:42–24.

L. R. Jones et al. (1980) "Unmasking Effect of Alamethicin on the $Na^+,K^+$)–ATPase, β–adrengenic Receptor–coupled Adenylate Cyclase, and cAMP–Dependent Protein Kinase Activities of Cardiac Sarcolemmal Vesicles," *J. Biol. Chem.* 225(20):9971–80.

Y. Salomon. (1979) "Adenylate Cyclase Assay," *Adv. Cyclic Nucleotide Res.* 10:35–55.

C. W. Woon et al. (1989) "Expression of a $G_{as}$ $G_{ai}$ Chimera That Constitutively Activates Cyclic AMP Synthesis," *J. Biol. Chem.* 264:5687–93.

Birnbaumer et al. (1980) "Transient and Steady State Kinetics of the Interactions of Guanyl Nucleotides with the Adenylyl Cyclase from the Rat Liver Plasma Membranes," *J. Biol. Chem.* 255:3542–51.

P. J. Munson and D. Rodbard (1980) "Ligand: A Versatile Computerized Approach for Characterization of Ligand–Binding Systems," *Anal. Biochem.* 107:220–39.

B. D. Hoit et al. (1995) "In Vivo Echocardiographic Detection of Enhanced Left Ventricular Function in Gene–Targeted Mice With Phospholamban Deficiency," *Circ Res.* 77:632–37.

D. J. Sahn et al. (1978) "Recommendations Regarding Quantitation in M–Mode Echocardiography: Results of a Survey of Echocardiographic Measurements," *Circ* 58:1072–83.

Y–F Xioa et al. (1995) Enhancement of Cardiac $G_{s\alpha}$ and Chloride–currents in Transgenic Mice Overexpressing $G_{s\alpha}$ (Abstract) *Circ.* (In press).

H. Kume et al. (1992) "Stimulatory and inhibitory regulation of calcium–activaed potassium channels by guanine nucleotide–binding proteins," *Proc. Natl. Acad. Sci. USA* 89:11051–55.

H–Y Wang et al. (1992) "Antisense oligodeoxynucleotides to G, protein α–subunit sequence accelerate differentiation of fibroblast to adipocytes," *Nature* 358:334–37.

M. Bomsel and K. E. Mostov K.E. (1993) "Possible Role of Both the α an βγ Subunits of the Heterotrimeric G Protein $G_g$, in Transcytosis of the Polymeric Immunoglobulin Receptor," *J. Biol. Chem.* 268:25824–35.

I. J. Benjamin et al. (1989) "Isoproterenol–Induced Myocardial Fibrosis in Relation to Myocyte Necrosis," *Circ. Res.* 65:657–70.

R. J. Robbins and J. L. Swain (1992) "C–myc Protooncogene Modulates Cardic Hypertrophic Growth in Transgenic Mice," *Am. J. Physiol.* 262:H590–H597.

L. Hitinger et al. (1995) "Hemodynamic Mechanisms Responsible for Reduced Subendocardial Coronary Reserve in Dogs with Severe Left Ventricular Hypertrophy," *Cir.* 92:978–86.

Gaudin et al. (1995) "Overexpression of $G_{S\alpha}$ Protein in the Hearts of Transgenic Mice," *J. Clin. Invest.* 95:1676–1683.

Bachmann et al. (1992) "Transgenic Rats Carrying the Mouse Renin Gene—Morphological Characterization of a Low–renin Hypertension Model," *Kidney International* 41:24–36.

Behringer et al. (1988) "Heart and Bone Tumors in Transgenic Mice," *Proc. Natl. Acad. Sci. USA* 85:2648–2652.

Chalifour et al. (1990) "Polyomavirus Large T–antigen Expression in Heart of Transgenic Mice Causes Cardiomyopathy," *Oncogene* 5:1719–1726.

Chien, (1992) "Signalling Mechanisms for the Activation of an Embryonic Gene Program During the Hypertrophy of Cardiac Ventricular Muscle," *Basic Res. Cardiol.*, 82 (Suppl. 2):49–58.

Gruver et al., "Targeted Developmental Overexpression of Calmodulin Induce Proliferative and Hypertrophic Growth of Cardiomyocytes in Transgenic Mice," *Endocrinology* 133:376–388.

Field et al. (1988) "Atrial Natriuretic Factor–SV40 T Antigen Transgenes Produce Tumors and Cardiac Arrhythmias in Mice," *Science* 239:1029–1033.

Huen et al., "Dilated Heart Failure in Transgenic Mice Expressing the Epstein–Barr Virus Nuclear Antigen–Leader Protein," *J. Gen. Virol.* 74:1381–1391 (1993).

Jackson et al. (1990) "The c–myc Proto–oncogene Regulated Cardia Development in Transgenic Mice," *Molecular and Cellular Biology* 10:3709–3716.

Klinger et al. (1993) "Cardiopulmonary responses to chronic hypoxia in transgenic mice that overexpress ANP," *J. Appl. Physiol.* 75(1):198–205.

Landis et al. (1989) "GTPase Inhibiting Mutations Activate the α chain of $G_s$ and Stimulate Adenylyl Cyclase in Human Pituitary Tumours," *Nature* 340:692–696.

Milano et al. (1994) "Myocardial Expression of a Constitutively Active $\alpha_{1B}$–adrenergic Receptor in Transgenic Mice Induces Cardiac Hypertrophy," *Proc. Natl. Acad. Sci. USA* 91:10109–10113.

Milano et al. (1995) "Marked Enhancement in Myocardial Function Resulting from Overexpression of a Human β–adrenergic Receptor Gene," *The Journal of Thoracic and Cardiovascular Surgery* 109:236–241.

Palmiter et al. (1986) "Germ–line Transformation of Mice," *Ann. Rev. Genet.* 20:465–99.

Polge, et al., (1989) "Induced Expression of a Bovine Growth Hormone Construct in Transgenic Pigs," *Biotechnology in Growth Regulation;* Heap, Praser and Lamming, eds; pp. 189–199.

Seachrist (1994) "Gene Transfer to Spark a Failing Heart," *Science* 264:507–508.

Steinhelper et al. (1990) "Cardia Tumors and Dysrhythmias in Transgenic Mice," *Technologic Pathology* 18:464–469.

Tsukamoto et al. (1995) "Gene Transfer and Expression in Progeny After Intravenous DNA Injection into Pregnant Mice," *Nature Genetics* 9:243–248.

Thorburn et al. (1993) "HRas–dependent Pathways can Activate Morphological and Genetic Markers of Cardiac Muscle Cell Hypertrophy," *J. Biol. Chem.* 268:2244–2249.

Yatani et al., (1987) "A G Protein Directly Regulated Mammalian Cardiac Calcium Channels," *Science* 238:1288–1292.

Yee et al. (1989) "Cardiac and Neurological Abnormalities in v–fps Transgenic Mice," *Proc. Natl. Acad. Sci. USA* 86:5873–5877.

\* cited by examiner

TG

TRANSGENIC MODEL OF HEART FAILURE

This invention was made with government support under grant NIH 5 PO1 HL 38070 awarded by the National Institutes of Health and consortium grant PHS NIH 5 PO1 HL 38070 awarded by the Public Health Service, National Institutes of Health. The Government has certain rights in the invention.

FIELD OF THE INVENTION

The present invention relates to transgenic models of heart failure and, more particularly, to transgenic animals and methods for testing the usefulness of chemical compounds in the treatment of heart failure.

BACKGROUND OF THE INVENTION

Heart failure is one of the leading causes of morbidity and mortality in the United States. Heart failure can result from any condition that reduces the ability of the heart to pump blood. Most frequently, heart failure is caused by decreased contractility of the myocardium, resulting from reduced coronary blood flow. Many other factors may result in heart failure, including damage to the heart valves, vitamin deficiency, and primary cardiac muscle disease. [A. C. Guyton (1982) *Human Physiology and Mechanisms of Disease,* Third Edition, W. B. Saunders Co., Philadelphia, Pa., p. 205]. Heart failure is commonly manifested in association with myocardial infarction. [*Manual of Medical Therapeutics* (1989) Twenty-Sixth Edition, Little, Brown & Co., Boston (W. C. Dunagan and M. L. Ridner, eds.), pp. 106–09].

The precise physiological mechanisms of heart failure are not entirely understood. However, heart failure is generally believed to involve disorders in several cardiac autonomic properties, including sympathetic, parasympathetic, and baroreceptor responses. [K. Kiuchi et al. (1993) *J. Clin. Invest.* 91:907].

The sympathetic division of the autonomic nervous system plays a key role in cardiac function. Adrenergic impulses of the sympathetic system stimulate β-adrenergic receptors disposed in various regions of the heart. These regions include the sinoatrial node, the atrioventricular node, and the ventricles, which result in increased heart rate, increased automaticity and conduction velocity, and increased ventricular contractility, respectively. [Goodman and Gilman's *The Pharmacological Basis of Therapeutics* (1990) Eighth Edition, Pergamon Press, Inc. (Alfred Goodman Gilman et al., eds.), pp. 88–90]. Though the heart contains both $\beta_1$- and $\beta_2$-adrenergic receptors, the $\beta_1$-adrenergic receptors are more important for physiological responses.

The effect, if any, of elevated catecholamine levels on the density of β-adrenergic receptors has not been definitively elucidated. To illustrate, studies involving experimental animals with heart failure have shown an increase in β-adrenergic receptor density, no change in density, or a decrease in density. [K. Kiuchi et al. (1993) J. Clin. Invest. 91:907; see also D. E. Vatner et al. (1989) *J. Clin. Invest.* 84:1741]. Studies involving failing human hearts have been reported to contain fewer β-adrenergic receptors in the left ventricle [see, e.g., M. R. Bristow et al. (1982) *N Eng. J Med.* 307:205], and the receptors that are present bind catecholamine agonists with a reduced affinity. Thus, the failing heart shows a reduced responsiveness to catecholamines (i.e., catecholamine desensitization).

Whether activation of myocardial β-adrenergic receptors is beneficial or deleterious over the long term, particularly in the pathogenesis of human heart failure, remains enigmatic. Although it seems clear that the acute role of β-adrenergic receptor-activation over a time frame of seconds to hours evolved as an evolutionary advantage for predators and prey alike (i.e., the fight or flight response), a major clinical puzzle revolves around whether a persistent enhancement of sympathetic drive to the heart, as can occur following major insults such as myocardial infarction or cardiac failure, might paradoxically lead to gradual deterioration of healthy cardiocytes and thereby to global organ dysfunction.

Generally speaking, heart failure in humans begins with reduced myocardial contractility, which leads to reduced cardiac output. In turn, the reduced cardiac output triggers increased sympathetic discharge (ie., norepinephrine, also referred to as noradrenaline and levarterenol), leading to the chronic elevation of circulating catecholamine levels characteristic of heart failure. [W. F. Ganong (1987) *Review of Medical Physiology,* Thirteenth Edition, Appleton & Lange, CN, pp. 534–535]. Heart failure is also characterized by hypertrophy of the ventricles, manifested in part by an increase in the myocyte cross-sectional area. In addition to the presence of myocardial hypertrophy, the failing heart shows excess collagen deposition. [R. A. Kloner and V. J. Dzau (1990) Heart Failure, Chapter 23 in *The Guide to Cardiology,* Second Edition, R. A. Kloner (ed.) Le Jacq Communications, p. 359].

A. The Treatment Of Heart Failure

Modalities for treating heart failure can be divided into (i) non-pharmacological treatment and (ii) pharmacological treatment. Non-pharmacological treatment is primarily used as an adjunct to pharmacological treatment. One means of non-pharmacological treatment involves reducing the sodium in one's diet. In addition, non-pharmacological treatment also entails the elimination of certain precipitating drugs, including negative inotropic agents (e.g., certain calcium channel blockers and antiarrhytmic drugs like disopyramide), cardiotoxins (e.g., amphetamines) and plasma volume expanders (e.g., nonsteroidal antiinflammatory agents and glucocorticoids).

Treatment with pharmacological agents represents the primary mechanism for reducing or eliminating the manifestations of heart failure. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure.

If diuretics are ineffective, vasodilatory agents may be used; the angiotensin converting (ACE) inhibitors (e.g., enalopril and lisinopril) not only provide symptomatic relief, they also have been reported to decrease mortality. [L. Y. Young et al. (1989) *Handbook of Applied Therapeutics,* Applied Therapeutics, Inc., Vancouver, Wash., pp. 7.1–7.12 and 9.1–9.10]. Again, however, the ACE inhibitors are associated with adverse effects that result in their being contraindicated in patients with certain disease states (e.g., renal artery stenosis).

Similarly, an inotropic agent, ie., a drug that improves cardiac output by increasing the force of myocardial muscle contraction, may also be indicated if the diuretics do not result in adequate relief. The inotropic agent most commonly used by ambulatory patients is digitalis. However, it is associated with a panoply of adverse reactions, including gastrointestinal problems and central nervous system dysfunction.

B. The Study Of Heart Failure And The Design Of Rational Drug Treatments

The currently used pharmacological agents have severe shortcomings in particular patient populations. The availability of new safe and effective agents would undoubtedly benefit patients who either cannot use the pharmacological modalities presently available, or who do not receive adequate relief from those modalities.

Different methods of designing drugs are presently being used. Regardless of the methodology utilized, the development of new pharmacological agents generally entails a great deal of time, effort, and expense. Unfortunately, many chemically different entities must often be screened before an effective agent is found (if one is found at all) for a particular ailment. Obviously, it would not be possible to test a large number of chemical entities on human hearts that exhibit signs of heart failure; not only would it be unfeasible to gather enough subjects to perform the experiments, it would not be safe to test such agents in humans.

What is needed is a model of heart failure that may be used for the testing of chemical compounds in the treatment of heart failure. The model must not require the use of human hearts, and it must be easy and relatively inexpensive to construct so that a large number of chemical compounds can be tested. The model should provide scientists with a more thorough understanding of the characteristics of heart failure, and, in this regard, it must incorporate and be representative of the physiological characteristics of the human heart.

SUMMARY OF THE INVENTION

The present invention provides animal models for heart failure in mammals and in particular in humans. The present invention is illustrated by the use of transgenic mice containing a $G_{s\alpha}$ transgene. The invention is not limited by the particular type of animal used. Any non-human animal may be used for the production of the transgenic animals of the invention including but not limited to murines, porcines and lagomorphs. Furthermore, the present invention is not limited to any particular strain of mice, when the invention is practiced using transgenic mice. The invention is illustrated using C57BL/6J mice as embryo donors. Other suitable strains of mice include C57BL/6Ka, C3H, ICN, FEB, Balb/c, CD-1 and $F_1$ offspring produced by mating any of the aforementioned strains. In addition, $F_1$ offspring resulting from the mating of any of the above identified strains with one another may be used for the isolation of fertilized eggs (i.e., embryos) suitable for the generation of transgenic mice. The present invention is further not limited to the use of any particular breed or strain of pigs, when the invention is practiced using transgenic pigs. The invention is illustrated, but not limited to, the use of Landrace, Duroc, Hampshire and PBZ 991 breeds of pigs. The present invention is further not limited to the use of any particular breed or strain of rabbits, when the invention is practiced using transgenic rabbits; examples of suitable breeds of rabbits include but are not limited to the New Zealand and Dutch Belted breeds.

The present invention provides non-human animals overexpressing $G_{s\alpha}$ mRNA in the cardiac tissue of the non-human animal. In a preferred embodiment, the non-human animals overexpressing $G_{s\alpha}$ mRNA in the cardiac tissue do not overexpress $G_{s\alpha}$ mRNA in their skeletal muscle. In a preferred embodiment, the non-human animals overexpressing $G_{s\alpha}$ mRNA in the cardiac tissue display manifestations of heart failure; in particular the animals display a dilated cardiomyopathy and thus are particularly useful as an animal model of human dilated cardiomyopathy. In a particularly preferred embodiment, the non-human animals of the invention overexpress mRNA encoding the short isoform of a $G_{s\alpha}$ protein. In yet another embodiment, the genome of the non-human animals which overexpress $G_{s\alpha}$ mRNA in their cardiac tissue contains an oligonucleotide sequence encoding a $G_{s\alpha}$ protein. In another embodiment, the genome of the non-human animals which overexpress $G_{s\alpha}$ mRNA in their cardiac tissue contains a promoter element operably linked to an oligonucleotide sequence encoding a $G_{s\alpha}$ protein. In a preferred embodiment, the promoter element comprises an α-myosin heavy chain gene promoter. In a particularly preferred embodiment, the promoter element which is operably linked to an oligonucleotide sequence encoding a $G_{s\alpha}$ protein comprises the α-MHC-$G_{s\alpha}$ transgene. As discussed above, the present invention is not limited by the type of non-human animal chosen. In a preferred embodiment, the non-human animal is selected from the group consisting of porcines and murines.

The present invention further provides a method for producing a non-human transgenic animal overexpressing $G_{s\alpha}$ mRNA in cardiac tissue, the method comprises: a) introducing into an embryonal cell of a non-human animal an oligonucleotide sequence encoding a $G_{s\alpha}$ protein; b) transplanting the transgenic embryonal cell formed thereby into a recipient female parent; and c) identifing at least one offspring containing the transgene wherein $G_{s\alpha}$ mRNA is overexpressed in the cardiac tissue of the offspring. As discussed in detail below in the Experimental section, identification of offspring containing the transgene is accomplished by demonstrating the presence of the transgene in genomic DNA isolated from the offspring using methods known in the art such as Southern blotting or the use of primers corresponding to sequences present in the transgene in a polymerase chain reaction. Northern blot analysis or any other suitable method may be used to demonstrate that mRNA expressed from the transgene is present in elevated levels relative to the level of expression of the endogenous $G_{s\alpha}$ mRNA transcript.

In a preferred embodiment, the method for producing the non-human transgenic animal employs an oligonucleotide sequence encoding a $G_{s\alpha}$ protein, wherein the oligonucleotide sequence further comprises a promoter element operably linked to the oligonucleotide sequence encoding the $G_{s\alpha}$ protein capable of directing the expression of the oligonucleotide sequence encoding a $G_{s\alpha}$ protein in a cardiac-specific manner. In yet another preferred embodiment, the non-human transgenic animals which overexpress the $G_{s\alpha}$ mRNA in a cardiac-specific manner do not overexpress $G_{s\alpha}$ mRNA in skeletal muscle.

In a preferred embodiment, the method for producing the non-human transgenic animal employs an α-myosin heavy chain gene promoter operably linked to he oligonucleotide sequence encoding a $G_{s\alpha}$ protein. In a particularly preferred embodiment, the α-myosin heavy chain gene promoter is the rat α-myosin heavy chain gene promoter. In a particularly preferred embodiment, the α-MHC-$G_{s\alpha}$ transgene is used to produce the transgenic non-human animals of the present invention. The non-human animals used in the method for producing the non-human transgenic animals are preferably selected from the group consisting of porcines and murines.

The invention further provides a method for screening compounds for the ability to prevent or treat the manifestations of heart failure in a non-human transgenic animal which comprises: a) providing a non-human animal overexpressing $G_{s\alpha}$ mRNA in the cardiac tissue of the non-human animal; and b) administering a compound to the non-human animal. The compound may comprise a known or a potential therapeutic compound. In a preferred embodiment, the method further comprises c) measuring an improvement in the physiologic function of the heart of the non-human animal and thereby identifying a compound as therapeutic. In one embodiment, the compound is administered to the non-human animal prior to the onset of manifestations of heart failure. In another embodiment, the compound is administered to the non-human animal after the onset of manifestations of heart failure. The compound used to contact the non-human animal may comprise a β-adrenergic receptor antagonist; the β-adrenergic receptor antagonist is preferably selected from the group consisting of $β_1$-specific adrenergic receptor antagonists, $β_2$-specific adrenergic receptor antagonists, and non-selective β-adrenergic receptor antagonists. The β-adrenergic receptor antagonist may be a known β-adrenergic receptor antagonists (e.g., acebutolol, atenolol, butoxamine, carteolol, esmolol, labetolol, metoprolol, nadolol, penbutolol, propranolol, and timolol) or may be a derivatives of known β-adrenergic receptor antagonists. Indeed any compound, which functionally behaves as a β-adrenergic receptor antagonist is encompassed by the screening methods of the present invention.

In another embodiment, the therapeutic compound used to contact the non-human animal may comprise an angiotensin-converting enzyme inhibitor. The angiotensin-converting enzyme inhibitor may be selected from known angiotensin-converting inhibitors (e.g., benazepril, captopril, enalopril, fosinopril, lisinopril, quinapril and ramipril) or may be a derivatives of known angiotensin-converting inhibitors. Indeed any compound, which functionally behaves as an angiotensin-converting inhibitors is encompassed by the screening methods of the present invention.

The screening methods of the present invention are not limited to screening β-adrenergic receptor antagonists and angiotensin-converting enzyme inhibitors for the ability to prevent or treat the manifestations of heart failure. The screening methods of the present invention encompasses the use of other classes of compounds including but not limited to endothelin antagonists (e.g., BQ 123 and Bosentan), angiotensin II receptor antagonists, vasopressin receptor antagonists and antioxidants.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 5B is a comparison of $G_{Sα}$ protein expression among offspring and generations within the same line as determined by Western blot analysis.

FIG. 8A shows, among other things, the lag period necessary for GppNHp to exert its stimulatory effect in cardiac membranes from control mice (open circles); this lag period is decreased in cardiac membranes from transgenic mice (solid circles).

FIG. 8B shows individual results (indicated by the presence of several open and solid circles) between 0 and 9 minutes that constitute a statistically significant difference (*) between transgenic and control mice.

FIG. 9A compares steady-state slopes between transgenic and control mice.

FIG. 9B compares initial slopes between transgenic and control mice.

FIG. 9C compares initial and steady-state slopes in control mice.

FIG. 9D compares initial and steady-state slopes in transgenic mice.

FIG. 11B is a graph showing the relationship of left ventricular ejection fraction in response to graded infusion of isoproterenol (i.e.,a dose-response curve).

FIG. 11C depicts an example of phasic waveforms of left ventricular pressure, left ventricular contractility, electrocardiograms, and heart rate in a wild-type control (left) and a transgenic mouse (right) in response to isoproterenol.

FIG. 13B is a bar graph showing quantitative evaluation of myocardial fibrosis, as determined by the measurement of collagen.

DEFINITIONS

Figure 1:
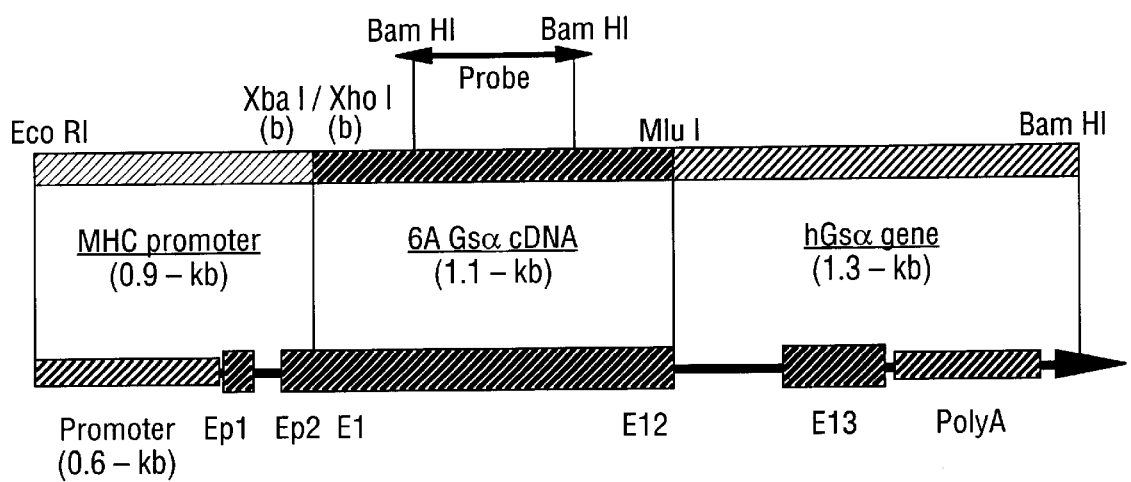
FIG. 1 is a diagram of the α-MHC-$G_{Sα}$ transgene.

To facilitate understanding of the invention, a number of terms are defined below.

The "non-human animals" of the invention comprise any non-human animal capable of overexpressing $G_{Sα}$ mRNA and/or proteins. Such non-human animals include vertebrates such as rodents, non-human primates, ovines, bovines, ruminants, lagomorphs, porcines, caprines, equines, canines, felines, aves, etc. Preferred non-human animals are selected from porcines (e.g., pigs), murines (e.g., rats and mice), most preferably mice and lagomorphs (e.g., rabbits).

The "non-human animals having a genetically engineered genotype" of the invention are preferably produced by experimental manipulation of the genome of the germline of the non-human animal. These genetically engineered non-human animals may be produced by several methods including the introduction of a "transgene" comprising nucleic acid (usually DNA) into an embryonal target cell or integration into a chromosome of the somatic and/or germ line cells of a non-human animal by way of human intervention, such as by the methods described herein. Non-human animals which contain a transgene are referred to as "transgenic non-human animals". A transgeneic animal is an animal whose genome has been altered by the introduction of a transgene.

The term "transgene" as used herein refers to a foreign gene that is placed into an organism by introducing the foreign gene into newly fertilized eggs or early embryos. The term "foreign gene" refers to any nucleic acid (e.g., gene sequence) which is introduced into the genome of an animal by experimental manipulations and may include gene sequences found in that animal so long as the introduced gene does not reside in the same location as does the naturally-ocurring gene.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The terms "promoter element" or "promoter" as used herein refers to a DNA sequence that precedes a gene in a DNA polymer and provides a site for initiation of the transcription of the gene into mRNA.

The transgenes of the present invention comprise a tissue-specific promoter operably linked to nucleic acid sequences which encode a non-mutant form of a $G_{s\alpha}$ protein. "Non-mutant" forms of a $G_{s\alpha}$ proteins are encoded by nucleic acid sequences which produce a protein which has the same function as the wild-type or non-mutated form of a $G_{s\alpha}$ protein. Non-mutant forms of $G_{s\alpha}$ protein may be encoded by the wild-type DNA or mRNA or by nucleic acid sequences which contain mutations or alterations relative to the wild-type sequence so long as these modifications do not effect the function of the $G_{s\alpha}$ protein. For example, a number of mutant forms of $G_{s\alpha}$ proteins have been described wherein the function of the $G_{s\alpha}$ protein is altered. These examples include the Arg-201→His mutant form of the $G_{s\alpha}$ hamster gene and the Arg-201→Cys mutant form of the hamster $G_{s\alpha}$ gene [Michiels, et al. (1994) Proc. Natl. Acad. Sci. USA 91:10488 and Ma, et al. (1994) Endocrinol. 134:42, respectively]. Both of these mutant forms of the hamster $G_{s\alpha}$ protein are constitutively active forms of the protein (i.e., these mutant forms of the protein are always in the active state). The expression of a constitutively active form of a $G_{s\alpha}$ protein leads to the constitutive activation of adenylyl cyclase which in turn leads to chronically elevated cAMP levels in the cell.

Embryonal cells at various developmental stages can be used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage [Brinster, et al. (1985) Proc. Natl. Acad. Sci. USA 82:4438–4442]. As a consequence, all cells of the transgenic non-human animal will carry the incorporated transgene. This will in general also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873191 describes a method for the micro-injection of zygotes; the disclosure of this patent is incorporated herein in its entirety.

Retroviral infection can also be used to introduce transgenes into a non-human animal. The developing non-human embryo can be cultured in vitro to the blastocyst stage. During this time, the blastomeres can be targets for retroviral infection [Janenich (1976) Proc. Natl. Acad. Sci. USA 73:1260–1264]. Efficient infection of the blastomeres is obtained by enzymatic treatment to remove the zona pellucida [Hogan et al. (1986) in Manipulating the Mouse Embryo, Cold Spring Harbor Laboratory Press, Cold Spring Harbor, N.Y.]. The viral vector system used to introduce the transgene is typically a replication-defective retrovirus carrying the transgene [Jahner, D. et al. (1985) Proc. Natl. Acad Sci. USA 82:6927–6931; Van der Putten, et al. (1985) Proc. Natl. Acad Sci. USA 82:6148–6152]. Transfection is easily and efficiently obtained by culturing the blastomeres on a monolayer of virus-producing cells [Van der Putten, supra; Stewart, et al. (1987) EMBO J. 6:383–388]. Alternatively, infection can be performed at a later stage. Virus or virus-producing cells can be injected into the blastocoele [Jahner, D. et al. (1982) Nature 298:623–628]. Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo [Jahner, D. et al. (1982) supra]. Additional means of using retroviruses or retroviral vectors to create transgenic animals known to the art involves the micro-injection of retroviral particles or mitomycin C-treated cells producing retrovirus into the perivitelline space of fertilized eggs or early embryos [PCT International Application WO 90/08832 (1990) and Haskell and Bowen (1995) Mol. Reprod. Dev. 40:386].

A third type of target cell for transgene introduction is the embryonal stem (ES) cell. ES cells are obtained by culturing pre-implantation embryos in vitro under appropriate conditions [Evans, et al. (1981) Nature 292:154–156; Bradley, et al. (1984) Nature 309:255–258; Gossler, et al. (1986) Proc. Acad. Sci. USA 83:9065–9069; and Robertson, et al. (1986) Nature 322:445–448]. Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal. For review see Jaenisch, (1988) *Science* 240:1468–1474. Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (see Example 3 for a protocol for performing Northern blot analysis). Appropriate controls are included on the Northern blot to control for differences in the amount of RNA loaded from each tissue analyzed (Example 3 herein provides an example of using the amount of 28S rRNA, an abundant RNA transcript present at essentially the same amount in all tissues, present in each sample as a means of normalizing or standardizing the $G_{s\alpha}$ mRNA-specific signal observed on Northern blots). The amount of mRNA present in the band corresponding in size to the correctly spliced $G_{s\alpha}$ transgene RNA is quantified; other minor species of RNA which hybridize to the transgene probe are not considered in the quantification of the expresssion of the transgenic mRNA (see Example 3).

"Cardiac-specific overexpression" refers to the expression of greater than about 3-fold higher levels of $G_{s\alpha}$ mRNA in cardiac tissue of animals harboring a $G_{s\alpha}$ transgene as compared to the level of expression of the endogenous $G_{s\alpha}$ mRNA in a control or non-transgenic animal; additionally the expression of $G_{s\alpha}$ mRNA from the transgene in non-cardiac tissues of transgenic animals will be no greater than about 2-fold higher than the levels observed in non-cardiac tissues of control or non-transgenic animals.

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rales and the like including laboratory findings associated with heart failure.

The term "treatment" or grammatical equivalents encompasses the improvement and/or reversal of the symptoms of heart failure (i.e, the ability of the heart to pump blood). "Improvement in the physiologic function" of the heart of the non-human transgenic animals of the present invention may be assesed using any of the measurements described herein (e.g., measurement of ejection fraction, fractional shortening, left ventricular internal dimension, heart rate, etc. in response to isoproterenol and/or norepinephrine), as well as any effect upon the transgenic animals' survival; the response of treated transgenic animals and untreated transgenic animals is compared using any of the assays described herein (in addition, treated and untreated non-transgenic animals may be included as controls). A compound which causes an improvement in any parameter associated with heart failure when used in the screening methods of the instant invention may thereby be identified as a therapeutic compound.

The term "dilated cardiomyopathy" refers to a type of heart failure characterized by the presence of a symmetrically dilated left ventricle with poor systolic contractile function and, in addition, frequently involving the right ventricle.

The term "compound" refers to any chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present invention. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of heart failure.

The term "β-adrenergic receptor antagonist" refers to a chemical compound or entity that is capable of blocking, either partially or completely, the beta (β) type of adrenoceptors (i.e., receptors of the adrenergic system that respond to catecholamines, especially norepinephrine). Some β-adrenergic receptor antagonists exhibit a degree of specificity for one receptor subtype (generally $β_1$); such antagonists are termed "$β_1$-specific adrenergic receptor antagonists" and "$β_2$-specific adrenergic receptor antagonists." The term "β-adrenergic receptor antagonist" refers to chemical compounds that are both selective and non-selective antagonists. Examples of β-adrenergic receptor antagonists include, but are not limited to, acebutolol, atenolol, butoxamine, carteolol, esmolol, labetolol, metoprolol, nadolol, penbutolol, propranolol, and timolol. The use of derivatives of known β-adrenergic receptor antagonists is encompassed by the methods of the present invention. Indeed any compound, which functionally behaves as a β-adrenergic receptor antagonist is encompassed by the methods of the present invention.

The terms "angiotensin-converting enzyme inhibitor" or "ACE inhibitor" refer to a chemical compound or entity that is capable of inhibiting, either partially or completely, the enzyme involved in the conversion of the relatively inactive angiotensin I to the active angiotensin II in the renin-angiotensin system. In addition, the ACE inhibitors concomitantly inhibit the degradation of bradykinin, which likely significantly enhances the antihypertensive effect of the ACE inhibitors. Examples of ACE inhibitors include, but are not limited to, benazepril, captopril, enalopril, fosinopril, lisinopril, quinapril and ramipril. The use of derivatives of known ACE inhibitors is encompassed by the methods of the present invention. Indeed any compound, which functionally behaves as an ACE inhibitor is encompassed by the methods of the present invention.

The term "reporter gene" refers to a nucleic acid sequence which encodes a product that is easily and quantifiably detected. Reporter genes are often operably linked to known or putative promoter and/or enhancer elements to permit the study of these elements (i.e., to define regions upstream of genes which are responsible for tissue-specific expression and/or constitutive or basal levels of expression). Genes commonly used as reporter genes in the study of eukaryotic gene expression include the bacterial genes encoding β-galactosidase, chloramphenicol acetyltransferase and β-glucuronidase.

DESCRIPTION OF THE INVENTION

The present invention relates to transgenic models of heart failure and, more particularly, to transgenic animals and methods for testing the usefulness of chemical compounds in the treatment of heart failure. The description of the invention is divided into the following parts: I) The Nature and Effect of the Heterotrimeric Guanine Nucleotide-Binding Stimulatory Protein; II) Cardiac-specific Expression of $G_{s\alpha}$ mRNA with the α-MHC Promoter; III) The Effect of Enhanced $G_{s\alpha}$ Expression; IV) The Physiological and Pathological Effects of Enhanced $G_{s\alpha}$ Expression; V) The Relationship of Enhanced $G_{s\alpha}$ Expression to the Pathogenesis of Heart Failure; VI) Screening Potential Therapeutic Compounds and VII) Other Transgenic Animal Models.

I. The Nature and Effect of the Heterotrimeric Guanine Nucleotide-Binding Stimulatory Protein In normal heart tissue, when an agonist (e.g., epinephrine) binds to the β-adrenergic receptor, the receptor forms a ternary complex with the $G_s$ protein (GTP-binding regulatory protein or heterotrimeric guanine nucleotide-binding stimulatory protein). [For review see, C. J. Homcy et al. (1991) Annu. Rev. Physiol. 53:137]. The $G_s$ protein is a heterotrimer comprising α, β and γ subunits ($G_{s\alpha}$, $G_{s\beta}$, and $G_{s\gamma}$, respectively); the heterotrimer binds GDP. When the $G_s$-receptor complex is formed, GTP is exchanged for GDP. Once GTP is bound, the complex dissociates and $a_{\alpha s}$-GTP associates with adenylyl cyclase. This association activates adenylyl cyclase and results in the synthesis of cAMP. Increased intracellular cAMP levels cause the phosphorylation of several proteins which are responsible for a calcium-mediated increase in contractility. Thus, the GTP-binding heterotrimeric regulatory protein ($G_s$) couples the β-adrenergic receptor to activation of adenylyl cyclase.

$G_s$ is a member of a large multigene family whose protein products play important roles in mediating signal transduction across the cell membrane. [A. G. Gilman (1987) Annu. Rev. Biochem. 56:615–49]. Existing models (human and animal) of heart failure have shown that alterations in β-adrenergic receptor-$G_s$-adenylyl cyclase coupling underlie the reduced catecholamine (e.g., epinephrine and norepinephrine) responsiveness characteristic of heart failure. [C. J. Homcy et al. (1991) Annu. Rev. Physiol. 53:137]. Studies conducted in a variety of animal models of cardiac hypertrophy [D. E. Vatner et al. (1984) J. Clin. Invest. 73:1473–82; L. Chen et al. (1991) J. Clin. Invest. 87:293–98], heart failure [D. E. Vatner et al. (1985) J. Clin. Invest. 76:2259–64; J. P. Longabaugh et al. (1988) J. Clin. Invest. 81:420–24], or ischemia [E. E. Susanni et al. (1989) Circ. Res. 65:1145–50], and in a model of in vivo desensitization [D. E. Vatner et al. (1989) J. Clin. Invest. 84:1741–48], indicate that primary alterations in the β-adrenergic receptor-$G_s$-adenylyl cyclase pathway do occur distal to the receptor.

In all of these models, there is a global reduction in adenylyl cyclase activation in cardiac sarcolemma (i.e., the plasma membrane of a muscle fiber), which can be associated with a reduction in $G_{s\alpha}$ activity. $G_{s\alpha}$ activity is frequently quantified by the S49 cyc⁻ reconstitution assay, which measures activity by determining the ability of solubilized sarcolemma to reconstitute fluoride-stimulated adenylyl cyclase activity in membranes prepared from S49 lymphoma cell line cyc⁻; that cell line is deficient in the $G_s$ protein, but does contain a functional adenylyl cyclase catalytic unit. [L. Chen et al. (1991) J. Clin. Invest. 87:293–98]. Changes in the amount of $G_{s\alpha}$ in these reports, however, are relatively small (~40%) considering the abundance of $G_{s\alpha}$ in cardiac membranes. Therefore, there is a question as to whether alterations in the expression of $G_{s\alpha}$ in pathophysiological states could contribute to the altered cAMP production in the failing hearts. A recent study in S49 lymphoma cells suggested that the availability of adenylyl cyclase, rather than the amount of $G_{s\alpha}$ protein, is the limiting factor for agonist stimulation of adenylyl cyclase. [A. A. Alousi et al. (1991) FASEB (Fed. Am. Soc. Exp. Biol.) J. 5:2300–03].

The role of stoichiometry in the regulation of β-adrenergic receptor-$G_s$-adenylyl cyclase interactions remains unknown in cardiocytes, particularly in vivo in the intact functioning heart. The present invention includes an examination of whether alteration in the amount of $G_{s\alpha}$ in the heart affects cAMP production and the physiologic effects thereof.

Two isoforms of the $G_{s\alpha}$ protein are known; the long isoform has an apparent molecular weight of approximately 52,000 on SDS-polyacrylamide gels and the short isoform has an apparent molecular weight of approximately 45,000. The two isoforms of the $G_{s\alpha}$ protein are encoded by two different mRNAs which arise via differential splicing of a primary RNA transcript encoded by a single $G_{s\alpha}$ gene [A. G. Gilman (1987) Annu. Rev. Biochem. 56:615–49]. In present invention, the short isoform of $G_{s\alpha}$ was overexpressed in the hearts of mice into whom a $G_{s\alpha}$ minigene construct, under the control of a rat α-MHC promoter [J. Rottman et al. (1990) in *The Dynamic State of Muscle Fibers* (D. Pett, ed.) Waltyer de Gruyter, New York, pp. 3–16], had been introduced as a transgene. Thus, the present invention involved an assessment of the efficacy of this promoter construct and the effects of $G_{s\alpha}$ overexpression on adenylyl cyclase activity in sarcolemmal membranes prepared from the hearts of transgenic mice.

II. Cardiac-Specific Expression of $G_{s\alpha}$ mRNA with the α-MHC Promoter

The present invention contemplates inducing cardiac-specific overexpression of $G_{s\alpha}$. To achieve this, a portion of the rat α-myosin heavy chain (α-MHC) gene containing the 0.6 kb α-MHC promoter element was used. [J. Rottman et al. (1990) in *The Dynamic State of Muscle Fibers* (D. Pett, ed.) Waltyer de Gruyter, New York, pp. 3–16] In vitro, this portion of the α-MHC gene can direct reporter gene expression specifically in cardiac myocytes.

The upstream portion of the mouse α-MHC gene has been used for the generation of transgenic mice. [J. Gulick et al. (1991) J. Biol. Chem. 266:9180–85; A. Subramaniam et al. (1991) J. Biol. Chem. 266:24613–20]. In these previous experiments, various amounts of sequences located 5' of the start of the coding region in the mouse α-MRC gene were inserted in front of the bacterial chloramphenicol acetyltransferase gene in order to identify regions responsible for tissue- and developmental stage-specific expression of the α-MHC gene. One of these experiments found that a 3.0 kb fragment located upstream of the mouse α-MHC gene (corresponding to a region where the sequence is preferentially conserved between mouse and rat) is competent to direct expression of the reporter gene in a cardiac-specific way. However, linkage of the chloramphenicol acetyltransferase gene to a short portion of the α-MHC gene with only 138 base pairs upstream of the transcriptional start site did not direct expression either in muscle or non-muscle cells. [Subramaniam et al. (1991) J. Biol. Chem. 266:24613–20].

The present invention utilized a 0.9 kb fragment of the rat α-MHC gene which contains the 0.6 kb promoter portion to direct cardiac specific expression of a $G_{S\alpha}$ transgene. The results obtained demonstrated that, using the rat promoter, only 0.6 kb 5' of the transcriptional start is sufficient to direct cardiac-specific expresssion of a transgene. The level of expression of $G_{S\alpha}$ mRNA directed by this 0.6 kb promoter fragment, however, differed among the positive lines of transgenic animals. While not intending to limit the invention to any particular mechanism, these differences in the expression level of the transgene may be related either to differences in copy number or the chromosomal position of integration of the foreign DNA. [R. Al-Shawi et al. (1990) Mol. Cell Biol. 10:1192–98]. In a study in which the SV40 large T antigen (TAG) was overexpressed in the heart utilizing a similar α-MHC promoter, the amount of TAG overexpression differed among individuals and different generations, even within the same line. [E. B. Katz et al. (1992) Am. J. Physiol. 262:H1867–H1876]. This contrasts with the results presented in the present invention where $G_{S\alpha}$ overexpression was consistently maintained across different generations and in which $G_{S\alpha}$ mRNA content was directly related to $G_{S\alpha}$ protein content across different transgenic lines (i.e., stable expression of the transgene was achieved). These differences may result from the different nature of the transgene products (a viral oncoprotein versus a housekeeping gene product) or from the inclusion of intronic sequences in the construct used in the present invention.

Since no overexpression was observed in skeletal muscle, in particular, or in a variety of other tissues (except brain), this analysis underscores the high degree of tissue-specificity of the 0.6 kb rat α-MHC promoter for cardiac muscle. In contrast with a previous observation where the mouse α-MHC upstream region was used [A. Subramaniam et al. (1991) *J. Biol. Chem.* 266:24613–20], no expression was observed in the lung of the transgene used in the present invention.

III. The Effect of Enhanced $G_{S\alpha}$ Expression

For over 40 years, experimental data have indicated that sympathetic activation of the heart becomes impaired in states of cardiac stress and that this process could contribute to eventual cardiac decompensation and heart failure. [C. J. Homcy et al. (1991) *Annu. Rev. Physiol.* 53:137–59]. Decreases in (i) total β-adrenergic receptor density, (ii) the high affinity fraction of β-adrenergic receptors, (iii) $G_s$ activity and (iv) adenylyl cyclase catalytic content have all been suggested as contributing to the process. In addition, the loss in $G_s$ functional activity accompanied by a decrease in $G_{S\alpha}$ mRNA content has been identified as a relatively early occurrence during the development of cardiac hypertrophy associated with chronic pressure-overload produced by aortic banding. [L. Chen et al. (1991) *J. Clin. Invest.* 87:293–98]. However, as indicated above, the decrement in $G_{S\alpha}$ content or activity reported in these studies was relatively small (~40%). Since $G_{S\alpha}$ protein exists in abundance relative to other proteins, e.g., receptors and adenylyl cyclase, in cardiac membranes, it has been unclear whether a small change in the content of this protein generates any functionally significant alteration.

In order to perform a critical analysis of the proposed causes of heart failure, it is important to first examine the effect of changing the content of any one of the above-mentioned components (e.g., $G_{S\alpha}$ mRNA content) in the normal heart, free of the confounding factors associated with heart failure. The availability of transgenic methods and animals provided by the present invention to alter the content of a particular gene product in the intact animal allows the assessment in the heart itself of altering the ratio of $G_{S\alpha}$ relative to receptor and the catalyst adenylyl cyclase. Enhancing $G_{S\alpha}$ expression would not only be informative, it is simpler than attempting to decrease $G_{S\alpha}$ content (although a decrement of $G_{S\alpha}$ expression is commonly observed in animal models of heart failure). For that reason, the short isoform of $G_{S\alpha}$ was overexpressed in a cardiac-specific manner in transgenic mice, using a rat α-MHC promoter that directs expression of the transgene to the heart.

The transgenic model of heart failure described in the present invention differs from prior models for several important reasons. First, the biochemical effect (i.e., rate of cAMP production) was a predicted outcome, although not a certain outcome since $G_{S\alpha}$ levels are in excess of levels of receptor and adenylyl cyclase. In all the pathological models described previously, the effects of changes in $G_{S\alpha}$ content could not be conclusively determined to be causal; rather, these models described simple associations. What was not predicted by the previous models was that the increase in $G_{S\alpha}$ content would have such a clear-cut physiological effect (e.g., increased heart rate and enhanced catecholamine responsiveness in mid-aged animals). Moreover, the previous models were not predictive of the cellular degeneration and fibrosis that occurs in animals as they age. The present hypothesis is that the increased sympathetic responsiveness in the heart secondary to increased $G_{S\alpha}$ is deleterious to the cardiocyte over time. Similarly, in the human, secondary to a cardiac insult, sympathetic nerve output is increased, and over time, this has deleterious effects on the, heart.

The constructs of the present invention resulted in $G_{S\alpha}$ mRNA levels being increased in the hearts of transgenic mice at a level 38-times the control. Despite this marked increase in mRNA, Western blotting identified only a 2.8-fold increase in the content of the $G_{S\alpha}$ short isoform protein, while $G_s$ activity was increased by 88%. The discrepancy between $G_{S\alpha}$ mRNA and $G_{S\alpha}$ protein levels suggests that the membrane content of $G_{S\alpha}$ is post-transcriptionally regulated.

Experiments were conducted to assess the effect of $G_{S\alpha}$ overexpression on adenylyl cyclase activity. These experiments revealed that steady-state adenylyl cyclase catalytic activity was not altered, either under basal or stimulated conditions (i.e., GTP+isoproterenol, GTPγS, NaF or forskolin). However, progress curves did show a significant decrease in the lag period necessary for GppNHp (guanyl-5'-yl imidodiphosphate) to stimulate adenylyl cyclase activity.

Additional studies showed that the relative number of β-adrenergic receptors binding agonist with high affinity was significantly increased (73±7% in transgenics vs. 55±4% in controls). The data demonstrate that a relatively small increase (approximately 2.5–3.0 fold) in the amount of the coupling protein $G_{S\alpha}$ can modify the rate of catalyst activation and the formation of agonist high-affinity receptors.

The methods and procedures of the present invention, as well as the specific results obtained, are presented in detail in the Experimental section below. However, from the discussion set forth above, it should be apparent that the availability of the transgenic lines provided by the present invention will allow one to examine receptor activation in the in vivo state or in isolated cardiomyocytes, as assessed by the ability of exogenously introduced catecholamines to increase heart rate, contractility or cAMP accumulation.

IV. The Physiological and Pathological Effects of Enhanced $G_{s\alpha}$ Expression The preceding discussion has focused primarily on the construction of the transgenic model of heart failure and the effect of $G_{s\alpha}$ overexpression on a molecular biological level. This part of the description presents an overview of the physiological and pathological effects of enhanced $G_{s\alpha}$ expression. The methodology and results of the specific experiments are set forth in detail in the Experimental section below. a. Physiological Effects Of $G_{s\alpha}$ Overexpression To study the physiological effect of myocardial $G_{s\alpha}$ overexpression in the transgenic mice of the present invention, responsiveness to sympathomimetic amines was examined by echocardiography in both transgenic and control mice. The average age of the mice was 10.3±0.2 months in both groups.

Initially, myocardial contractility in the transgenic mice of the present invention, as assessed by left ventricular fractional shortening (LVFS) and ejection fraction (EF), was not significantly different from that of control mice at baseline [LVFS 40±3 vs. 36±2%, EF 78±3 vs. 74±3% (transgenic mice vs. control mice, respectively)]. However, upon introduction of a sympathomimetic amine, myocardial contractility was found to be different. Specifically, LVFS and EF in the transgenic mice of the present invention during an isoproterenol infusion at 0.02 μg/kg/min were higher than those levels in control mice [LVFS 68±4 vs. 48±3%, EF 96±1 vs. 86±3% (transgenic mice vs. control mice, respectively)]. Similarly, a norepinephrine infusion at 0.2 μg/kg/min increased LVFS and EF in these transgenic mice more than in control mice [LVFS 59±4 vs. 47±3%, EF 93±2 vs. 85±3% (transgenic mice vs. control mice, respectively)]. In addition, heart rates of these transgenic mice were higher than those of control mice during infusions of both isoproterenol and norepinephrine.

While not intending to limit the invention to any particular mechanism, these results suggest that $G_{s\alpha}$ overexpression enhanced the efficacy of the β-adrenergic receptor-$G_S$-adenylyl cyclase signaling pathway. In turn, this leads to augmented inotropic and chronotropic responses to endogenous sympathetic stimulation. These responses mimic those often seen in heart failure in human beings because sympathetic nerve output is increased in failing hearts as a compensating mechanism to enhance cardiac output.

b. Pathological Effects Of $G_{s\alpha}$ Overexpression

The pathological effects of the overexpression of myocardial $G_{s\alpha}$ in the transgenic mice of the present invention were also assessed. Pathological and histological analyses of older transgenic mice hearts of these animals (16.0±0.8 months old) revealed hypertrophy, degeneration, atrophy of cells and replacement fibrosis. This was quantitatively reflected by significant increases (p<0.05) in collagen volume in the subendocardium [5.2±1.4% vs. 1.2±0.3% (transgenic mice vs. control mice, respectively)] and in the cross-sectional area of myocytes [298±29 μm² vs. 187±12 μm² (transgenic mice vs. control mice, respectively)].

Thus, the augmented inotropic and chronotropic responses to endogenous sympathetic stimulation, described in the previous section, result in readily detectable pathological consequences. As previously alluded to, over the life of the animal, this action results in myocardial damage characterized by cellular degeneration, necrosis and replacement fibrosis, with the remaining cells undergoing compensatory hypertrophy. Again, these responses mimic those often seen in heart failure in humans and indicate that overexpression of $G_{s\alpha}$ in an animal can provide a useful model for both studying heart failure (mimicking the enhanced sympathetic nerve output seen in the patient with heart failure) and for screening compounds useful in the treatment thereof.

It should be noted that, had the physiological and pathological/histological studies of the present invention not been conducted, the interpretation of the model of increased $G_{s\alpha}$ would have been entirely different. Since steady-state adenylyl cyclase activity was not enhanced and since there was no evidence for hypertrophy on gross examination of the heart, i.e., heart weight-to-body weight was not increased, one might conclude that the increased expression of $G_{s\alpha}$ did not have profound physiological or pathological consequences. Moreover, in vivo cAMP levels, which may fluctuate on a minute-to-minute basis or actually be heterogeneously distributed throughout the heart, may not be faithfully recapitulated by in vitro steady-state assays. [D. M. F. Cooper et al. (1995) Nature 374:421–24]. Therefore, the results provided by the physiological and pathological studies were surprising.

V. The Relationship of Enhanced $G_{s\alpha}$ Expression to the Pathogenesis of Heart Failure The results of the present invention have implications for the understanding of the pathogenesis of heart failure. There are currently two opposing views as to the role of adrenergic mechanisms in the pathogenesis and therapy of heart failure. One point of view holds that catecholamine desensitization is a signature of heart failure (M. R. Bristow et al. (1982) N. Engl. J Med. 307:205–11; D. E. Vatner et al. (1989) J. Clin. Invest. 84:1741–48; K. Kiuchi et al. (1993) J. Clin. Invest. 91:907–14), resulting in a critical defect in the normal compensatory mechanism of increased sympathetic drive. This viewpoint proposes that by replacing the sympathetic tone, e.g., through increasing the expression of β-adrenergic receptors (C. A. Milano et al. (1994) Science 264:582–86) or through treatment with adrenergic agonists, heart failure can be ameliorated. A variety of therapeutic approaches have been devised to augment the adrenergic support that dissipates with heart failure, e.g., dobutamine [Dies et al. (1986) Circ. (Abstract) 74:11–38; M. J. Krell et al. (1986) Am. Heart J. 112:787–92], prenalterol [H. Lambertz et al. (1984) Circ. 69:298–305], xamoterol [Ryden et al. (1990) Lancet 336:1–6], and milrinone [M. Packer et al. (1991) N. Engl. J Med 325:1468–75]. Unfortunately all of these therapeutic strategies have failed to materially alter the course of heart failure; indeed some have a deleterious effect (often increasing mortality).

In contrast, the opposite approach, i.e., β-adrenergic receptor-blockade, may be more useful. [S. N. Heilbrunn et al. (1989) Circ. 79:483–90; F. Waagstein et al. (1989) Circ. 80:551–63]. The fact that inhibition of β-adrenergic function is salutary in heart failure, particularly in view of recent beneficial effects of another β-blocker, carvedilol, in heart failure, provides further support for this approach. [M. Metra et al. (1994) J. Am. Coll. Cardiol. 24:1678–87; S. L. Olsen et al. (1995) J. Am. Coll. Cardiol. 25:1225–31]. Indeed, the results presented in the Experimental section, infra, support the latter concept. That is, while the normal physiological compensatory mechanisms of "fight or flight" (which include increased sympathetic drive) are important for the acute adjustments required in exercise, excitement and hypotension, on a chronic basis, these mechanisms are deleterious, as evidenced by the histological studies in the older transgenic mice (see the Experimental section, infra). While the precise mechanism underlying this deleterious effect remains unclear, the "$G_{s\alpha}$ transgenic mouse" may offer clues as to how enhanced sympathetic nerve-drive might trigger cell death via mechanisms such as apoptosis. A further extension of this concept is that catecholamine desensitization mechanisms, which are pathognomonic of heart failure, are actually salutary chronic compensatory mechanisms, and that overcoming these compensatory mechanisms by enhancing sympathetic activation is deleterious over the long term.

VI. Screening Potential Therapeutic Compounds

As indicated above, the present invention relates to transgenic animals and methods for testing the usefulness of chemical compounds in heart failure. It is anticipated that the animal model will provide definitive data about the effectiveness of agents currently used in heart disease as well as new experimental agents.

The major aspects of the screening process are discussed in the Experimental section below. Briefly, the chemical compounds being tested will be administered to the transgenic non-human animals of the present invention using any suitable route (e.g., oral, parenteral, rectal, etc.) over a suitable time period (e.g., several months) to determine whether they abrogate the pathological effects of $G_{s\alpha}$ overexpression. The present invention is not limited to screening any particular compounds or group of compounds. Chemical compounds to be tested include compounds (known or unknown) from chemical classes that have been shown to be effective in treating heart failure (e.g., calcium channel blockers, angiotensin-converting enzyme (ACE) inhibitors and β-blockers). It is well-known in the art that compounds of a particular class (e.g., the ACE inhibitors) often have a similar chemical structure; it is also well-known in the art that derivatives of such compounds (e.g., compounds created by the addition or deletion of a functional group) may improve efficacy and/or decrease adverse effects. The present invention contemplates that derivatives of known compounds will be tested using the non-human transgenic animal to examine their efficacy in treating and/or preventing heart failure.

It is anticipated that known compounds will be tested first because many of the effects of these compounds on humans are already known. In this situation, the screening process can be used to gather data such as which compounds are most effective at particular stages of heart failure. In addition, mortality and pathology studies will be carried out with compounds with a new mechanism of action (e.g., antioxidants and endothelin antagonists) to determine whether they prevent the pathologic changes seen in the transgenic mice. Of course, the animal testing will need to be supplemented and confirmed by testing on human subjects; however, the present animal model allows a large sample population to be tested at an early stage.

VII. Other Transgenic Animal Models

The previous discussion has been directed at a transgenic mouse as a model for heart failure. However, the present invention is not limited to a mouse model. Rather, other transgenic animal models might also be used to study heart failure and are intended to be within the scope of the present invention.

Pigs and rabbits represent two classes of animals that provide alternative animal models of heart failure. Examination of certain aspects of the pig heart will illustrate this point. The heart rate and coronary blood flow of pigs closely resembles that in humans. In addition, physiological stresses like ischemia can be superimposed on the pig to determine if the change is accelerated. The Experimental section below contains an example directed at a transgenic pig model.

From the above, it should be clear that the transgenic animals of the present invention provide a tool not only for investigating the biologic mechanisms underlying heart failure, but also for evaluating new therapies aimed at preventing or arresting its progression.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); pmol (picomoles); g (grams); mg (milligrams); μg (micrograms); ng (nanograms); L (liters); ml (milliliters); μl (microliters); cm (centimeters); mm (millimeters); μm (micrometers); nm (nanometers); ° C. (degrees Centigrade); hr (hour); sec (second); min (minutes); kd (kilodaltons); g (unit of force equal to the force exerted by gravity on a body at rest); IV (intravenous); α-MHC (α-myosin heavy chain); cAMP and cyclic AMP (adenosine 3':5'-monophosphoric acid); LVFS (left ventricular fractional shortening); LVID (left ventricular internal dimension); LVIDs (left ventricular internal dimension at the end of systole); LVIDd (left ventricular internal dimension at the end of diastole); EF (ejection fraction); iso (isoproterenol); NE (norepinephrine); $G_s$ or $G_s$ protein (GTP-binding regulatory protein or heterotrimeric guanine nucleotide-binding stimulatory protein); $G_{s\alpha}$ (α subunit of the $G_s$ protein); cDNA (complementary deoxyribonucleic acid); mRNA (messenger ribonucleic acid); rRNA (ribosomal ribonucleic acid); PAGE (polyacrylamide gel electrophoresis); Tween (polyoxyethylene-sorbitan); SDS (sodium dodecyl sulfate); EDTA (ethylene diamine tetraacetic acid); EGTA {[ethylene-bis(oxy-ethylenenitrilo)] tetra-acetic acid}; $MgCl_2$ (magnesium chloride); NaCl (sodium chloride); NaF (sodium fluoride); KCl (potassium chloride); $NaPO_4$ (sodium phosphate); Tris (tris (hydroxymethyl)-aninomethane); Tris HCl (Tris buffer titrated with HCl); HEPES (4-(2-hydroxyethyl)-1-piperazineethanesulfonate); GppNHp (guanyl-5'-yl imidodiphosphate); DTT (dithiothreitol); SSC (saline-sodium citrate buffer); NS (not significant); S.E.M (standard error of the mean); GTPγS (guanosine 5'-O-(3-thio) triphosphate); IBMX (3-isobutyl-1-methyl-xanthine); Adobe Systems Corporation, Mountain View, Calif.); Aldrich (Aldrich Chemical Co., Milwaukee, Wis.); Amersham (Amersham, Arlington Heights, Ill.); Baxter (Deerfield, Ill.); Beckman (Beckman Instruments, San Ramon, Calif.); Bio-Rad (Richmond, Calif.); Braintree (Braintree Scientific, Inc., Braintree, Mass.); Brinkmann Instruments (Westbury, N.Y.); Clay Adams (Clay Adams Co., Parsippany, N.J.); Grass Instruments (Quincy, Mass.); Hamilton Company (Reno, Nev.); Harvard Apparatus (Harvard Apparatus, Inc., S Natick, Mass.); Millipore (Bedford Mass.); Interspec-ATL (Ambler, Pa.); Jackson Laboratory (Jackson Laboratory, Bar Harbor, Me.); Lotus (Mountain View, Calif.); Millipore (Bedford, Mass.); Molecular Dynamics (Molecular Dynamics, Sunnyvale, Calif.); New England Nuclear (New England Nuclear, Boston, Mass.); NIH (National Institutes of Health, Bethesda, Md.); Pharmacia (Piscataway, N.J.); Promega (Promega Corp., Madison, Wis.); S & S and Schleicher & Schuell (Schleicher & Schuell, Inc., Keene, N.H.); Science Accessories (Southport, Conn.); Sigma (Sigma Chemical Co., St. Louis, Mo.); Sony Corporation (Tokyo, Japan); Universal Imaging (Universal Imaging Corporation, West Chester, Pa.).

Unless otherwise indicated in the examples that follow, comparisons between transgenic and control animal values were made using a paired t test. P<0.05 was taken as a minimal level of significance.

EXAMPLE 1

Construction of a $G_{S\alpha}$ Transgene

In order to study the effect of altered expression of $G_{S\alpha}$ in the hearts of transgenic mice, a minigene encoding the short isoform of $G_{S\alpha}$ was constructed. The minigene used the promoter from the rat α-myosin heavy chain (MHC) gene to drive expression of $G_{S\alpha}$ sequences. The minigene (i.e., transgene) was constructed as follows. A 0.9 kb EcoRI-XbaI (blunted) fragment, containing a 0.6 kb promoter portion, the first exon, the first intron and the first 43 base pairs of the second exon proximal to the initiation ATG was isolated from the rat α-MHC gene. [V. Mardavi et al. (1984) Proc. Natl. Acad. Sci. USA 81:2626]. This construct was digested with XbaI and the ends were made blunt by treatment with the Klenow fragment; thereafter, it was digested with EcoRI and the 0.9 kg fragment containing the promoter, exon 1, intron 1 portion of exon 2 was isolated on a low melting point (LMP) agarose gel.

A 1.1 kb XhoI (blunted)-MluI fragment of the dog cDNA of $G_{S\alpha}$ containing exons 1–12 was isolated by digestion of construct 6A [Y. Isikawa et al. (1990) J. Biol. Chem. 265:8458] with XhoI followed by treatment with the Kienow fragment to fill-in the 3' recessed termini (i.e., to blunt the ends). Thereafter, it was digested with MluI and the 1.1 kb fragment containing exons 1–12 was isolated on a LMP gel.

A 1.3 kb MtuI-BamHI fragment containing intron 12, exon 13 and the polyadenylation signal was isolated by digestion of the human $G_{S\alpha}$ gene [Kozasa et al, (1988) Proc. Natl. Acad. Sci. USA 85:2081] with MluI and BamHI and the 1.3 kb fragment was isolated on a LMP gel.

The above fragments were combined and inserted by using a four-way ligation into pGEM-7Zf (+) (Promega) digested with EcoRI and BamHI. E. coli strain DHα5 was transformed with the resulting vector. The resulting minigene, referred to as the α-MHC-$G_{S\alpha}$ transgene, is shown schematically in FIG. 1.

In FIG 1, the restriction fragments derived from the rat α-MHC gene (light grey box), the canine $G_{S\alpha}$ gene (black box) and the human $G_{S\alpha}$ gene (dark grey box) are shown using solid boxes (top of figure). The restriction sites used for subcloning are indicated above these boxes; the designation "(b)" indicates blunted sites. The bottom portion of FIG. 1 depicts the different components of the transgene. Exons are shown as solid boxes, and introns are depicted by solid lines. The "MHC promoter" contains 0.6 kb of 5' flanking sequence, the first exon (Ep1), the first intron and a portion of the second exon (Ep2) from the rat α-MHC gene. "6A$G_{S\alpha}$ cDNA" is a canine cDNA coding for the short isoform of the $G_{S\alpha}$ protein from exon 1 (E1) to exon 12 (E12). "h$G_{S\alpha}$" is a portion of the human $G_{S\alpha}$ gene containing intron 12, exon 13 (E13) and the polyadenylation signal (polyA). The 0.5 kb BamHI restriction fragment used as a probe for Southern and Northern blot analysis is indicated on the top of FIG. 1.

A portion of the human $G_{S\alpha}$ gene was used in place of canine gene sequences to provide sequences corresponding to exon 13 and the polyadenylation signal because the canine equivalent could not be obtained, even after repeated library screening. The amino acid sequence within this domain is identical between the human and canine $G_{S\alpha}$ thus the putative chimeric $G_{S\alpha}$ protein would possess the same amino acid sequence as the wild type canine $G_{S\alpha}$ protein. Furthermore, it has been previously reported that the addition of introns increases transcriptional efficiency of transgenes in transgenic mice. [R. L. Brinster et al. (1988) Proc. Natl. Acad. Sci. USA 85:836–40].

The resulting construct containing the α-MHC-$G_{S\alpha}$ transgene will be deposited with the American Type Culture Collection.

The α-MHC-$G_{S\alpha}$ transgene was prepared for microinjection as follows. Host cells containing the transgene construct were grown and plasmid DNA was isolated using standard techniques [e.g., QIAGEN-tips (QIAGEN) used according to the manufacturer's instructions]. The plasmid was digested with EcoRI and BamHI and a 3.3 kb restriction fragment was purified on a 0.8% agarose gel. The 3.3. kb α-MHC-$G_{S\alpha}$ transgene DNA band was excised from the gel, and the DNA was electroeluted using standard procedures [Current Protocols in Molecular Biology, Ausubel, et al., eds., John Wiley and Sons, Inc., pp.2.6.1–2.6.3 (1994)]. The electroeluted DNA was then concentrated and purified using an Elutip-d column (Schleicher and Schuell) according to the manufacturer's protocol and prepared for microinjection.

The isolated transgene was then microinjected into fertilized mouse eggs as described below to generate transgenic mice.

EXAMPLE 2

Generation of Transgenic Mice

C57BL/6J mice (Jackson Laboratory) were used as embryo donors. Fertilized eggs at the pronuclear stage were collected from the oviducts of superovulated C57BL/6J females that had been mated to C57BL/6J males. Founder transgenic mice were created by microinjection of approximately 1000 copies of the linear transgene (prepared as described in Example 1) into the male pronucleus of the fertilized mouse eggs using techniques which are standard in the art [Wagner et al. (1981) Proc. Natl. Acad. Sci. USA 78:6376–80; Hogan, et al. (1986) Manipulating the Mouse Embryo, Cold Spring Harbor Laboratory Press, Cold Spring Harbor, N.Y.]. Microinjected eggs were implanted into the oviduct of 1-day pseudopregnant female mice for gestation to term. Positive founders (identified as described below) were bred to adult normal C57BL/6×C3HI (B6C3) $F_1$ hybrid females to establish independent germ lines.

a. Screening Of Transgenic Mice By Genomic Southern Blotting

Three weeks after the birth of animals resulting from the microinjected eggs, total genomic DNA was extracted from the tail of these mice using standard techniques. [B. Hogan et al. (1986) Manipulating the Mouse Embryo: A Laboratory Manual, Cold Spring Harbor Laboratory, Cold Spring Harbor, N.Y., pp. 174–76]. The extracted DNA was analyzed for the presence of the integrated α-MHC-$G_{S\alpha}$ transgene sequences by Southern blotting. Ten micrograms of genomic DNA from each mouse tail was digested with BammH and electrophoresed on 0.8% agarose gels. The DNA was transferred to a nylon membrane and probed with a 0.5 kb BamHI restriction fragment derived from the 6A $G_{S\alpha}$ cDNA (see FIG. 1). The 0.5 kb BamHl restriction fragment was radiolabeled with [$^{32}$P]-dCTP, using the Multiprime DNA Labeling System (Amersham) according to the manufacturer's instructions.

The Southern blots were prehybridized in a solution containing 50% formamide, 5×SSC (43.8 g/l NaCl, 6.9 g/l $NaH_2PO_4 \cdot H_2O$ and 1.85 g/l EDTA, pH adjusted to 7.4 with NaOH), 5×Denhardt's solution [50×Denhardt's contains per 500 ml: 5 g Ficoll (Type 400, Pharamcia), 5 g BSA (Fraction V; Sigma)], 25 mM sodium phosphate (pH 6.5), 0.25 mg/ml salmon sperm DNA and 0.1% SDS. Prehybridization was conducted for a minimum of 2 hours at 42° C. Hybridization of the Southern blots was performed using the radiolabeled 0.5 kb BamHI probe in a solution containing 50% formamide, 5×SSC, 5×Denhardt's solution, 25 mM sodium phosphate (pH 6.5), 0.25 mg/ml salmon sperm DNA and 0.1% SDS. The blots were hybridized for 48 hours at 42° C., and then washed in a solution containing 0.2% SDS, 0.2× SSC at 60° C. for 30 minutes, followed by autoradiography. A representative autoradiogram is shown in FIG. 2.

Figure 2:
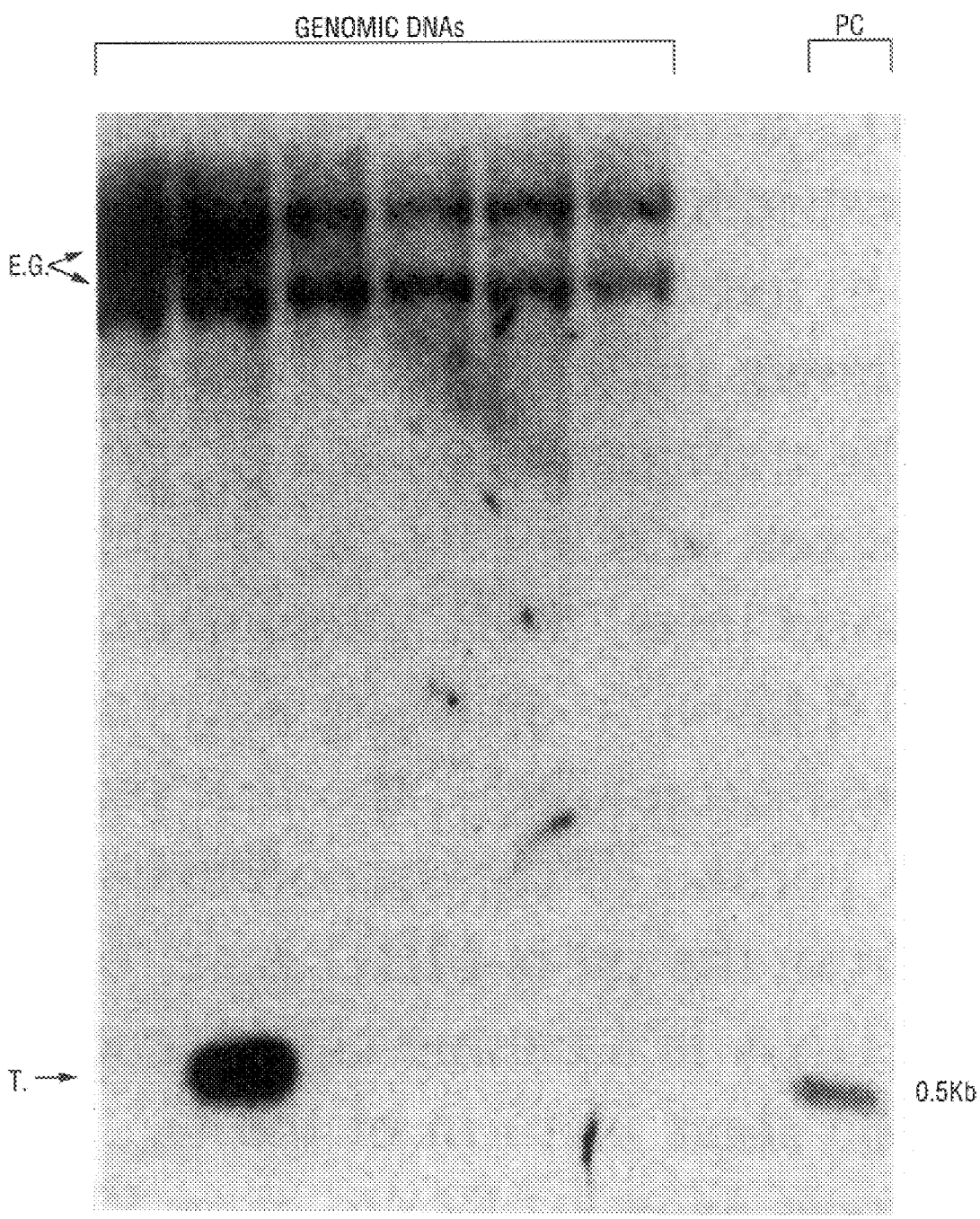
FIG. 2 depicts the results of screening of transgenic mice by Southern blot analysis.

Referring to FIG. 2, "PC" indicates 10 pg of the pGEM-7Z plasmid containing the transgene digested with BamHI, which was run as a positive control to assess the sensitivity of the detection assay, "E.G." indicates the endogenous gene, and "T." is the transgene, indicating that the mouse corresponding to this genornic DNA (second lane) is a positive founder. Each lane contains 10 μg of mouse genomic DNA, which was digested with BamHI (with the exception of the lane marked "PC" which contained 10 pg of the plasmid containing the transgene as described above).

Screening by Southern blot analysis was conducted on 116 mice (57 male and 59 female) resulting from injection of fertilized eggs. Of these mice, 10 (2 male and 8 female mice) were positive, as shown by genomic Southern blotting with a 0.5 kb portion of the $G_{S\alpha}$ cDNA as the probe (FIG. 2).

Breeding of these 10 founder animals with normal mice gave 5 independent germ lines. Three of the initial founders remained infertile. Two other founders produced no positive litters, suggesting that these two mice were probably chimeric.

EXAMPLE 3

Characterization of Expression Levels of Transgenes

The expression of $G_{S\alpha}$ in the heart and other tissues of transgenic animals was examined. This example presents quantitative data relating to the level of $G_{s\alpha}$ mRNA and protein expression and discusses the relationship between the two.

a. $G_{s\alpha}$ mRNA Expression In Transgenic Mice

Total RNA was isolated from mouse tissues using standard techniques. The isolated total RNA was fractionated on 1.0% agarose-formaldehyde gels and transferred to a nylon membrane (i.e., a Northern blot). The Northern blots were probed using either a 0.5 kb BamHI cDNA fragment (described above) or an oligonucleotide corresponding to the 28S ribosomal RNA sequence; the oligonucleotide was a 32-mer with the following sequence: 5'-CGGCAGCGGCCGTCAGCTCTCACC TGCCCTCG-3' (SEQ ID NO:1). [Gonzalez et al, *Proc. Natl. Acad. Sci. USA* (1985) 82:7666]. The 0.5 kb BamHI restriction fragment was radiolabeled with [$^{32}$P]dCTP as described in Example 2. The oligonucleotide probe complementary to 28S ribosomal RNA sequences was radiolabeled using [γ-$^{32}$P]ATP and T4 polynucleotide kinase.

Prehybridization and hybridization of Northern blots were performed at 42° C. in the 50% formamide solution described above (Example 2). After 24 hours of hybridization, the blot was washed in a solution containing 0.2×SSC and 0.2% SDS at 60° C. for 30 minutes, followed by autoradiography. The blots were then erased ("stripped") by incubation in a solution containing 0.001% SSC, 0.2% SDS at 95° C. for 30 min.) and the rehybridized with the 28S rRNA oligonucleotide probe. The amount of $G_{S\alpha}$ mRNA expression was standardized using 28S rRNA content as a control.

Expression of $G_{S\alpha}$ nRNA in the hearts of transgenic and normal (i.e., non-transgenic) mice was examined. Total cardiac RNA was isolated from the 5 independent germ lines (Example 2) and from normal mice. Cardiac RNA was isolated from $F_1$ animals bred from these 5 founder lines as well as from normal nice. Northern blots were prepared and hybridized as described above. A representative autoradiogram is shown in FIG. 3.

Figure 3:
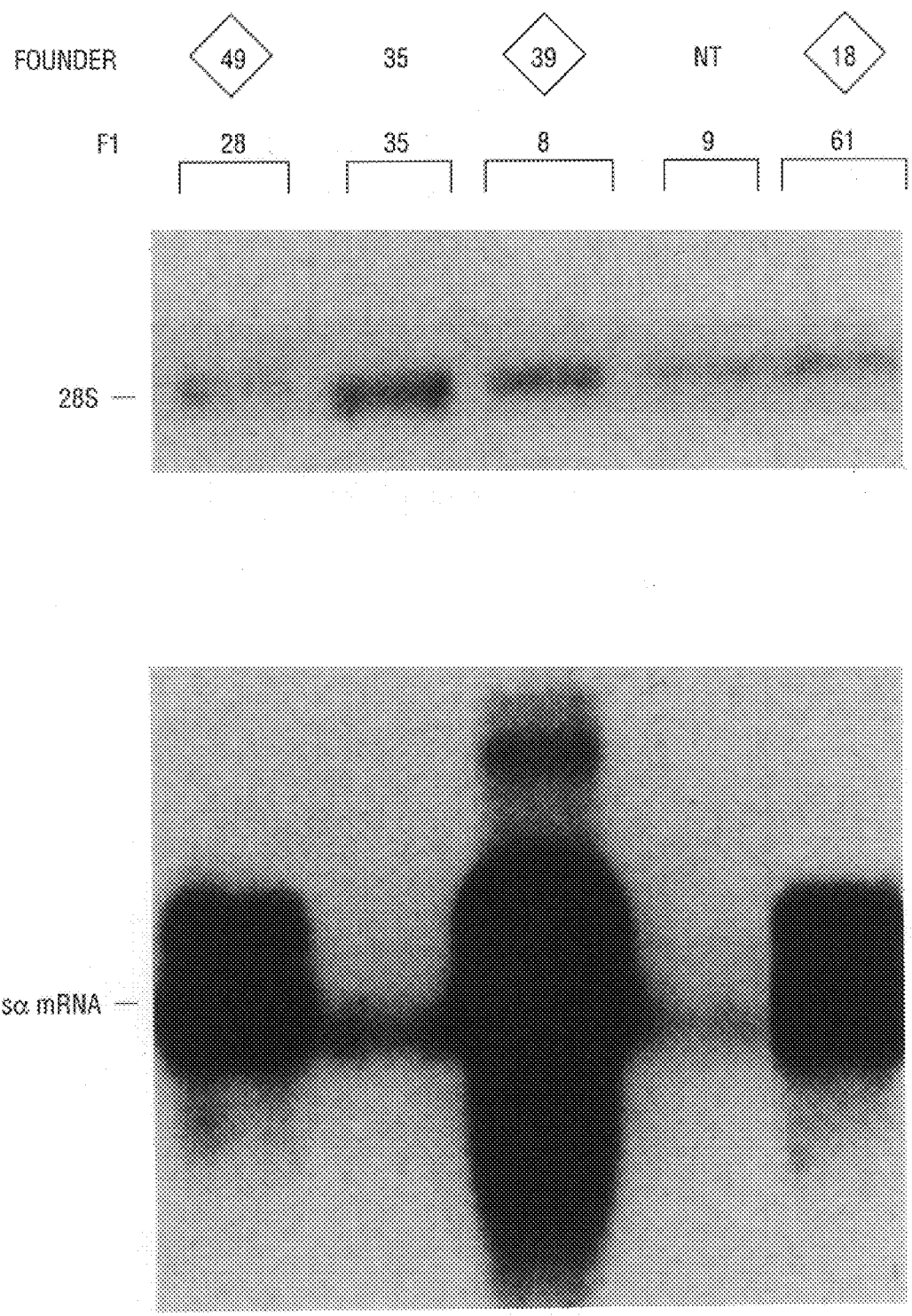
FIG. 3 indicates $G_{Sα}$ mRNA expression in the hearts of transgenic and non-transgenic mice as determined by Northern blot analysis.

In FIG. 3, each lane contains 30 μg of total RNA. As alluded to above, the $^{32}$P-labeled probe used for hybridization was either a 0.5 kb BamHI fragment derived from the $G_{S\alpha}$ cDNA (FIG. 3, bottom panel) or an oligonucleotide corresponding to the 28S ribosomal RNA sequence (FIG. 3, top panel). The numbers of the transgenic lines (founders) and of the $F_1$ mice (offspring) which were used in this assay are indicated on the top of FIG. 3 [For example, $F_1$ 28 was bred from founder 49]. The designation "NT" refers to a non-transgenic mouse. The numbers surrounded by a diamond ("◊") represent those lines that overexpressed $G_{S\alpha}$ mRNA.

The results shown in FIG. 3 demonstrate that transgenic lines 49, 39, and 18 were overexpressing $G_{S\alpha}$ mRNA in the heart. Lines 49 and 18 were both found to overexpress $G_{S\alpha}$ mRNA eight times the control level. Line 39 was found to overexpress $G_{S\alpha}$ mRNA 38 times the control level. Line 35 did not overexpress $G_{S\alpha}$ mRNA.

Two $G_{S\alpha}$ mRNA species of different sizes were detected in transgenic mice. The size of the smaller, more abundant $G_{S\alpha}$ mRNA species (the "major" band) was as expected if the $G_{S\alpha}$ transgene RNA were correctly spliced and is the same size as that of the endogenous $G_{S\alpha}$ message. A larger, but much less abundant message (the "minor" band) was also detected. The exact nature of this message (the "minor" band) is unknown; however, it could be an incompletely spliced species containing additional gene sequences (see FIG. 1). Thus, the major $G_{S\alpha}$ mRNA species was quantified as representing the expression of transgenic $G_{S\alpha}$ mRNA. Two lines (lines 18 and 49) both showed an eight-fold overexpression of $G_{S\alpha}$ mRNA (i.e., eight times greater than control). One line (line 39) showed a 38-fold overexpression. The two other lines (transgenic line 35 and non-transgenic line 8) did not show any overexpression of $G_{S\alpha}$ mRNA. Line 39, which showed the highest expression of $G_{S\alpha}$ mRNA, was further analyzed as described below.

b. Transgene Expression Exhibits Cardiac-Specificity

To assess the tissue and organ specificity of mRNA expression produced with the α-MHC promoter, Northern blot analysis was performed using total RNA extracted from lung, liver, kidney, skeletal muscle and brain. This experiment compared mice from line 39 (which had shown the highest expression of $G_{S\alpha}$ mRNA) with control mice from the same line. The results are depicted in FIG. 4.

For the Northern blot analysis, each lane contained 30 μg of total RNA, which was isolated from one of the aforementioned mouse tissues (i.e., lung, liver, kidney, skeletal muscle or brain). Samples were electrophoresed in a 1.0% agarose formaldehyde gel and the RNA was transferred to a nylon membrane. The resulting blots were then probed sequentially with the 0.5 kb BamHI $G_{S\alpha}$ cDNA probe (FIG. 4, bottom panel) or an oligonucleotide corresponding to the 28S ribosomal RNA sequence (FIG. 4, top panel) as described above. The 28S ribosomal RNA probe served as an internal control for total RNA loading and transfer efficiency. The top of FIG. 4 indicates the different organs and tissues tested. The "T" designation indicates a transgenic animal from line 39, while the "C" designation indicates a non- transgenic control from the same line.

Figure 4:
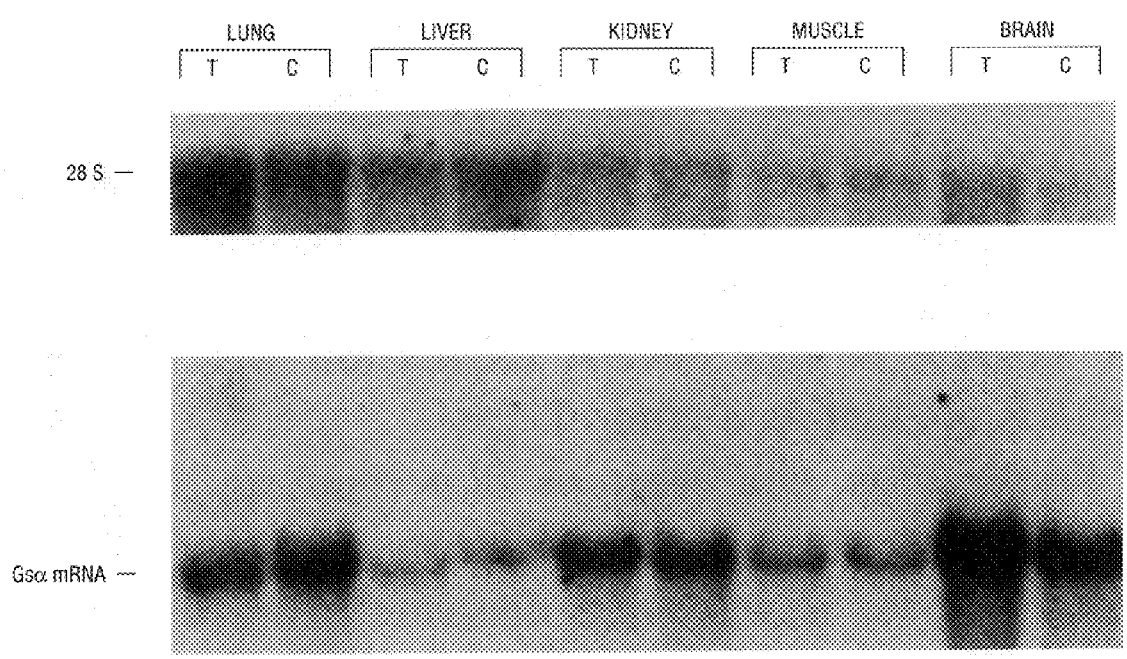
FIG. 4 indicates $G_{Sα}$ mRNA expression in various tissues of transgenic mice as determined by Northern blot analysis.

As shown in FIG. 4, this analysis showed a difference in $G_{S\alpha}$ mRNA expression between transgenic and control animals only in the brain. This difference between transgenic and control animals, however, did not reach a level comparable to that observed in the heart (2-fold overexpression in the brain versus 38-fold in the heart). Similar cardiac-specific expression was also seen in other lines, including transgenic line 18.

c. $G_{S\alpha}$ Protein Levels In Transgenic Mice

The effect of increased mRNA expression, induced by the transgene, on protein content was also assessed. For this assessment, Western blotting of cardiac $G_{S\alpha}$ protein was performed on membranes prepared from transgenic mice overexpressing $G_{S\alpha}$ mRNA or from normal mice using a commercially available antiserum specific for $G_{S\alpha}$ (New England Nuclear).

The membrane preparation was created according to the following procedure. One control mouse (from the same founder line as from the transgenic mouse) was sacrificed at the same time as each transgenic mouse. Hearts were dissected from the mice and homogenized in 10 mM Tris-HCl, pH 8.0, using a Polytron (Brinkmann Instruments). The homogenates were centrifuged twice at 48,000 g for 10 min and filtered through gauze. The resulting pellets were then resuspended in solution containing 100 mM Tris-HCl, pH 7.2, 1 mM EGTA and 5 mM $MgCl_2$ and rehomogenized (as described above).

Protein concentration was measured by the method of Bradford [Bradford, *Anal. Biochem.* 72:248–54 (1976)] using bovine serum albumin (BSA) as the standard. The membrane preparation was then aliquoted to be used for the adenylyl cyclase and $G_s$ reconstitution assays (described below) and Western blotting. Twenty micrograms of each membrane preparation was electrophoresed on a 4–20% gradient SDS-polyacrylamide gel. The membrane preparation proteins were then transferred to a polyvinylidene difluoride membrane (Immobilon, Millipore) for Western blotting immunodetection.

Western blotting immunodetection was performed with a 1:2000 dilution of $G_{S\alpha}$ antiserum (New England Nuclear) followed by a 1:300 dilution of anti-rabbit Ig peroxidase-linked species-specific whole antibody using the ECL detection system (Amersham). This antibody detected both mouse and canine $G_{S\alpha}$ proteins. After checking the linear relationship between staining and the amount of protein analyzed, $G_{S\alpha}$ protein was quantified by densitometry, using a computing densitometer (model 300 A, Molecular Dynamics). The developed Western blot is shown in FIG. 5.

Figure 5A:
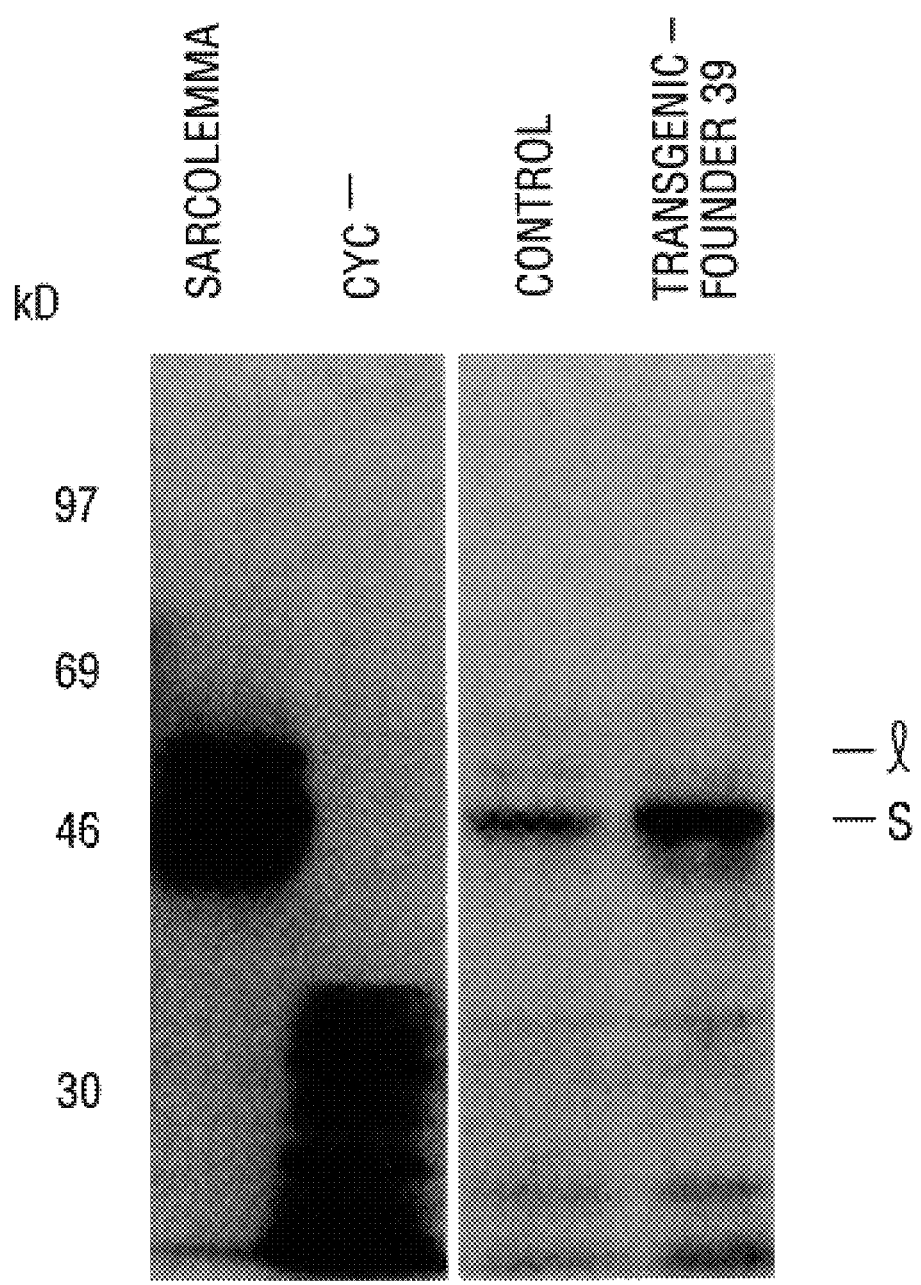
FIGS. 5A–B. 5A indicates $G_{Sα}$ protein expression in the hearts of transgenic and control mice as determined by Western blot analysis.

The results shown in FIG. 5a depict $G_{S\alpha}$ protein expression in the hearts of transgenic and control mice as determined by Western blot analysis. As a positive control (lane 1, "sarcolemma"), a membrane preparation from enriched dog sarcolemma [prepared as described in Kiuchi et al. (1993) *J. Clin. Invest.* 91:907] was loaded. The lane labeled "cyc-" contains the negative control, a membrane preparation from S49 cyc⁻(prepared as described below). The other two lanes, labeled "control" and "transgenic-founder 39" were loaded with 20 µg of membrane proteins prepared from a control mouse (third lane from the left) or transgenic mouse hearts (transgenic derived from line 39; fourth lane from the left). Approximate the size of the molecular weight markers (in kilodaltons) are listed on the left side of FIG. 5a under the heading "kD". Referring to the labeling on the right side of FIG. 5a, "l" indicates the band corresponding to the long $G_{S\alpha}$ isoform, which was used as a control for the loading, and "s" indicates the band corresponding to the short $G_{S\alpha}$ isoform, which was overexpressed.

Densitometry, using the long $G_{S\alpha}$ isoform as an internal control of loading and transfer, gave a semi-quantitative assessment of $G_{S\alpha}$ protein overexpression. Line 39, which showed a 38-fold overexpression of $G_{S\alpha}$ mRNA, demonstrated a 2.8-fold overexpression of the protein.

Figure 5B:
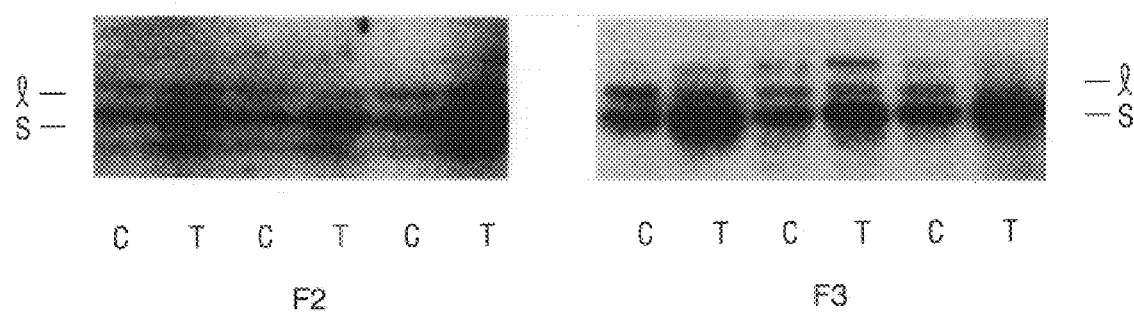

The degree of $G_{S\alpha}$ overexpression between offspring and generations within the same line was examined. FIG. 5b shows a comparison, by Western blot analysis, of $G_{S\alpha}$ protein expression among offspring from different generations. In FIG. 5b, the following abbreviations are used: "l" indicates the band corresponding to the long $G_{S\alpha}$ isoform; "s" indicates the band corresponding to the short $G_{S\alpha}$ isoform; "T" indicates transgenic mice and the "C" indicates control mice; "F2" and "F3" refer to the second generation and the third generation, respectively, of offspring derived from transgenic line 39. Denistometery was performed as described above.

The increase in membrane $G_{S\alpha}$ protein in the transgenic offspring was 2.8-fold. Thus, the degree of $G_{S\alpha}$ overexpression was consistent among offspring and generations within the same line. In contrast, using an antiserum specific for $G_{i\alpha2}$ [described in Liao and Homcy (1992) *Circ. Res.* 70:1018–26], no difference between transgenic and control mice was observed.

d. Relationship Of $G_{S\alpha}$ mRNA Content To $G_{S\alpha}$ Protein Levels

An obvious discrepancy exists between the steady-state mRNA levels (e.g., the 38-fold increase in line 39) induced by the transgene and the resulting increase in $G_{S\alpha}$ protein content (e.g., the 2.8-fold increase in line 39). While not limiting the invention to a particular theory, several potential mechanisms that might explain this finding are discussed. As previously alluded to, the size of the "major" band (ie., the size of the smaller, more abundant $G_{S\alpha}$ mRNA species) detected in the transgenic mice is similar to that of endogenous $G_{S\alpha}$ mRNA; one would expect this result if the RNA precursor was correctly spliced, thus making it unlikely that incorrect processing of the precursor RNA was contributing to the discrepancy in amounts of mRNA and protein. The size of the "minor" band (i.e., the larger, less abundant $G_{S\alpha}$ mRNA species) detected in transgenic mice is similar to that of the transgene itself ($G_{S\alpha}$ cDNA plus intron 12, see schematic in FIG. 1). When the transgene was constructed, care was taken to insure that the Kozak consensus sequence [Kozak (1986) *Cell* 44:283–92] present in the endogenous $G_{S\alpha}$ mRNA would be recapitulated. The total 5'-flanking sequence, based on the size of the principal mRNA species detected, is similar to that of the endogenous mRNA. Nevertheless, the possibility that the chimeric $G_{S\alpha}$ mRNA is less efficiently translated than is the wild type cannot be excluded.

It is also possible that the explanation for the discrepancy between mRNA and protein content has a post-translational basis wherein the nascent protein is rapidly catabolized. $G_{S\alpha}$ exists as a heterotrimeric complex in association with $\beta\gamma$ subunits. Rapid turnover of individual components of a multi-subunit protein has previously been shown when only one of the subunits is overexpressed in transfected cell lines. [Kurosaki et al. (1991) *Proc. Natl. Acad. Sci. USA* 88:3837–41]. It is possible that $\beta\gamma$ availability is rate-limiting and that "free" $G_{S\alpha}$ subunit is rapidly degraded within the cardiocyte. Recently, it has been shown that $G_{S\alpha}$ is palmitoylated, likely a requirement for its efficient association with the plasma membrane. [Linder et al. (1993) *Proc. Natl. Acad. Sci. USA* 90:3675–79; Taussig et al. (1993) *Science* 261:218–21]. One cannot readily assess whether incomplete post-translational processing of $G_{S\alpha}$ in the transgenic cardiocytes might contribute to lower than expected steady-state levels. Since $G_{S\alpha}$ has been found in soluble fractions [Lewis and Bourne (1992) *J. Cell Biol.* 119:1297–1307), the amount of $G_{S\alpha}$ in soluble fractions was compared between transgenic and control mice. However, no difference was found.

EXAMPLE 4

Quantification of Functional $G_s$ Activity

To assess whether the overexpressed $G_{S\alpha}$ protein was functional, $G_s$ activity was measured by a reconstitution assay in sarcolemma prepared from transgenic mice. The $G_s$ activity from transgenic mice (lines 39 and 18) was compared with that from control mice from the same lines.

Reconstitution of $G_s$ into S49 cyc$^-$ membranes was performed using the stable reconstitution protocol devised by P. C. Sternweis and A. G. Gilman [*J. Biol. Chem.* 254:3333–40 (1979)]. Briefly, cardiac membranes were first solubilized in 2% cholate in a buffer of 16 mM Tris, pH 8.0, 0.8 mM EDTA, and 0.8 mM DTT. The cholate extract was centrifuged at 20,000×g for 30 min, and then the endogenous adenylyl cyclase was inactivated by incubation at 30° C. for 10 min. Thereafter, the supernatant was diluted into a Lubrol buffer in preparation for reconstitution into 60 $\mu$g of S49 cyc$^-$ membranes; the S49 cyc$^-$ membranes were prepared according to the method, known in the relevant art, of E. M. Ross et al [*J. Biol. Chem.* 252:5761–75 (1977)].

Aluminum fluoride-responsive adenylyl cyclase activity was assessed over a range of solubilized cardiac membrane (1.5–4.5 $\mu$g for the crude membrane preparation) at 30° C. for 15 min; under these conditions, it is known to produce a linear response. The slope of this line (pmol of cAMP per min vs. added solubilized membrane preparation) was used as a measure of $G_s$ functional activity. [Longabaugh et al. (1988) *J. Clin. Invest.* 81:42–24]. Measurements were performed with a control from the same founder line for each transgenic sample. Solubilized cardiac membranes were prepared from the control mice and reconstituted into S49 cyc$^-$ membranes using the same procedure as for the transgenic mice.

As an index of the consistency of the cardiac membrane preparation, Na$^+$, K$^+$-ATPase enzymatic activity was measured according to the method of L. R. Jones et al. (1980) *J. Biol. Chem.* 225(20):9971–80. Briefly, Na$^+$, K$^+$-ATPase enzymatic activity was measured in a medium that contained 50 mM histidine, 3 mM MgCl$_2$, 100 mM NaCl, 10 mM KCl, and 3 mM Tris/ATP (pH 7.0). Na$^+$, K$^+$-ATPase enzymatic activity was defined as that activity that was not inhibited by ouabain.

Figure 6:
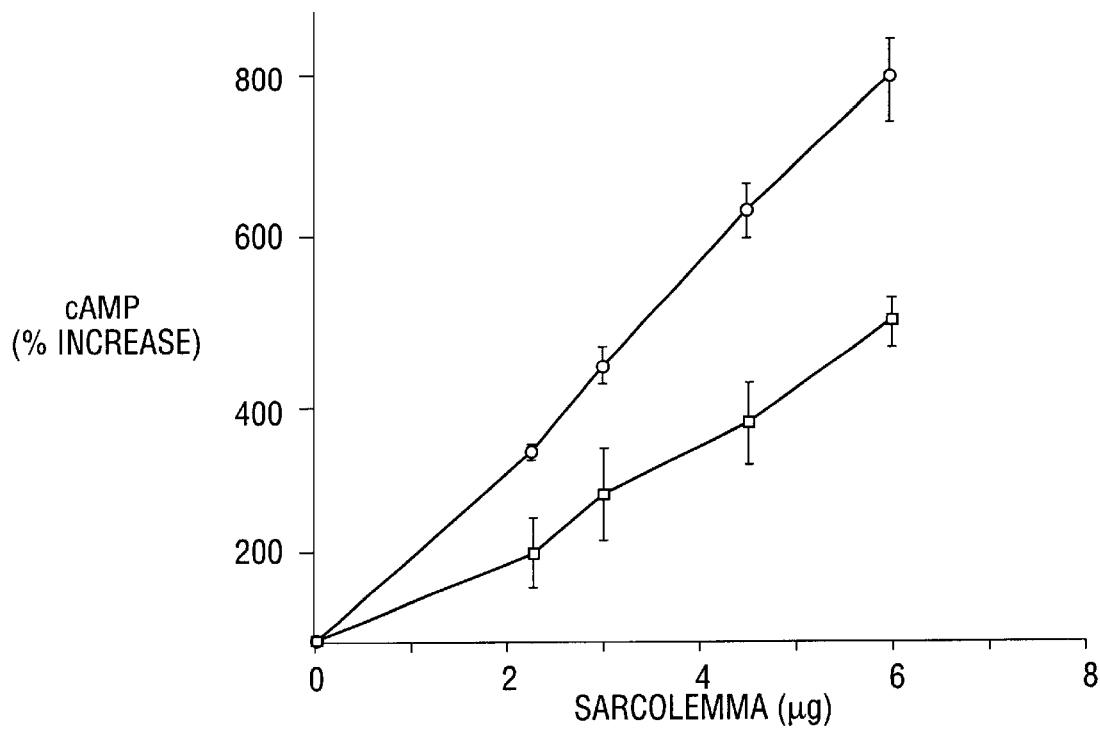
FIG. 6 is a graph depicting cardiac $G_s$ functional activity in transgenic mice.

FIG. 6 depicts the results of cardiac $G_s$ functional activity. The circles in FIG. 6 represent data points for the transgenic mice, whereas the squares represent data points for the control mice. The values in FIG. 6 are expressed as the percent increase over the adenylyl cyclase activity of cyc$^-$ membranes alone, and results are expressed as the mean±S.E.M. (n=4, p<0.01).

There was increased functional $G_s$ activity in the hearts of transgenic mice. More specifically, functional $G_s$ activity was higher in line 39 (188±10%, mean±S.E.M) compared to control animals from the same line. Thus, increased functional activity accompanied the increase in $G_{S\alpha}$ protein and mRNA levels. However, the absolute increment over control levels previously shown for $G_{S\alpha}$ mRNA and protein was not maintained. That is, while previous experiments indicated a 38-fold increase in mRNA (38±3, n=4) and a 2.8-fold increase in protein (2.8±0.2, n=8) over control, there was only a 1.9-fold increase in $G_{S\alpha}$ functional activity (1.9±0.1, n=4).

A similar pattern was observed in transgenic mouse line 18. In line 18, there was an 8-fold increase in mRNA (8.1±0.07, n=4), a 1.4-fold increase in protein (1.4±0.02, n=6), and a 1.2-fold (1.2±0.05, n=5) increase in $G_{S\alpha}$ functional activity. The mRNA data for line 18 are depicted in FIG. 3; the data related to protein levels and functional $G_{S\alpha}$ activity are not shown.

EXAMPLE 5

Effect of $G_{S\alpha}$ Protein Overexpression on Adenylyl Cyclase

In this example, the effect of $G_{S\alpha}$ protein overexpression on (i) basal and stimulated steady-state cardiac adenylyl cyclase activity and (ii) the time course of activation of cardiac adenylyl cyclase by GppNHp were assessed.

a. Effect Of $G_{S\alpha}$ Overexpression On Basal And Stimulated Steady-State Cardiac Adenylyl Cyclase Activity To assess whether $G_{S\alpha}$ overexpression in the heart resulted in increased adenylyl cyclase activity, the steady-state adenylyl cyclase activity in transgenic and control animals was compared by measuring the production of cAMP in sarcolemmal membranes under basal or stimulated conditions.

The following procedures were used in this example. Fifteen micrograms per tube of the crude cardiac membrane preparations were used for the adenylyl cyclase assay. Adenylyl cyclase activity was measured by a modification of the method of Y. Salomon. [*Adv. Cyclic Nucleotide Res.* 10:35–55 (1979)]. Briefly, fixed-time assays were performed in a final volume of 100 $\mu$l of a solution containing 20 mM HEPES (pH 8.0), 5 mM MgCl$_2$, 0.1 mM cAMP, 0.1 mM ATP and $^{32}$P-ATP (4 $\mu$Ci per assay tube), 1 mM creatine phosphate, 8 $\mu$g/ml creatine phosphokinase, and 0.5 mM IBMX as an inhibitor of cAMP phosphodiesterase. Each reaction was initiated by the addition of the membranes; the reaction mixture was incubated at 30° C. for 15 min, and the reaction was stopped by the addition of 100 $\mu$l of 2% SDS. Thereafter, cAMP was separated from ATP by successively passing the solution through Dowex (Bio-Rad) and alumina columns (Bio-Rad). To monitor recovery throughout the assay, $^3$H-labeled cAMP was included in the incubation mixture. The radioactivity was measured by liquid scintillation counting.

Stimulated adenylyl cyclase activities were measured with addition of 100 $\mu$M GTP+100 $\mu$M isoproterenol (GTP+iso), 100 $\mu$M GTP$\gamma$S, 10 mM NaF or 100 $\mu$M forskolin (Sigma). All measurements were performed in quadruplicate, with a non-transgenic control from the same founder line for each transgenic sample. Cyclic AMP production in the presence of GTP+iso was linear over 20 min in these preparations.

Figure 7:
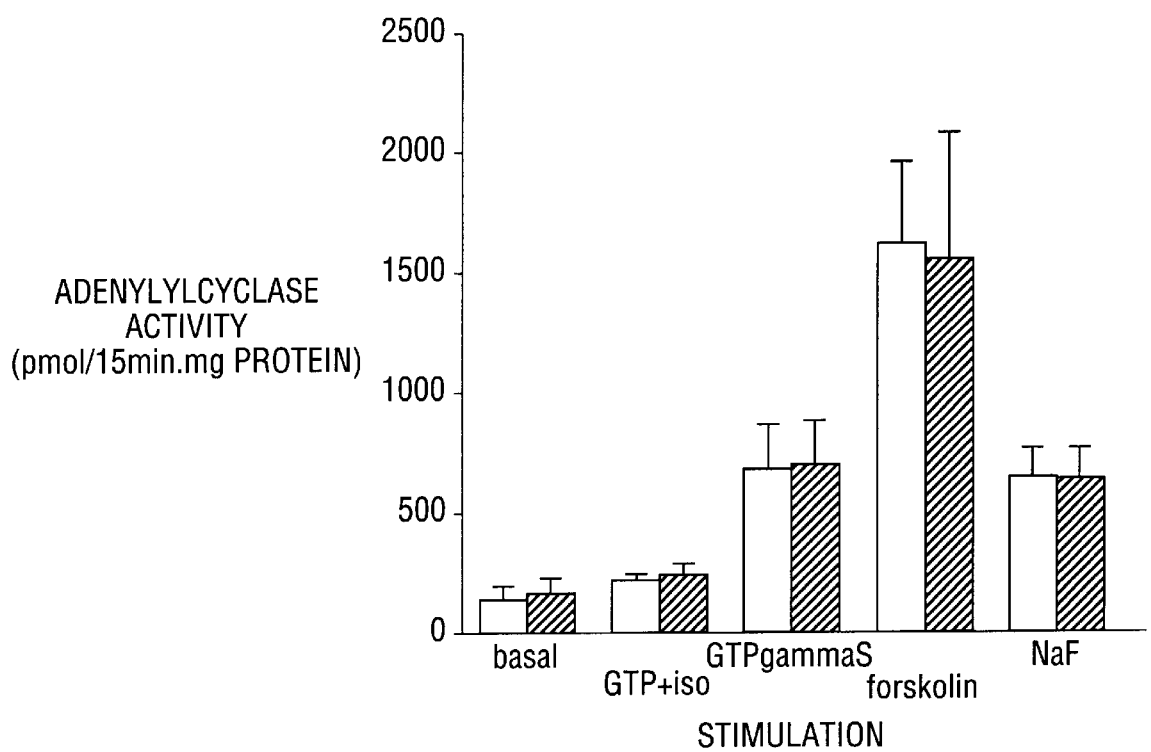
FIG. 7 is a bar graph depicting basal and stimulated cardiac adenylyl cyclase activity in transgenic mice.

The results are depicted in FIG. 7 in the form of a bar graph. Control values are represented as open bars, and values for transgenic mice (line 39) are represented as solid bars. Results are expressed as the mean±S.E.M. (n=8, p=NS). Referring to FIG. 7, no significant increase in steady-state adenylyl cyclase activity was detected under either basal or stimulated (GTP+iso, GTP$\gamma$S, NaF or forskolin) conditions. The data indicate that, under steady-state conditions, $G_{S\alpha}$ overexpression in the heart does not alter the maximal number of $G_{S\alpha}$-adenylyl cyclase complexes formed in myocytes.

There are a variety of studies which have suggested that the concentration of $G_s$ is several-fold in excess over that of both β-adrenergic receptor and the catalyst adenylyl cyclase in cell membranes. [A. A. Alousi et al. (1991) *FASEB J.* 5:2300–03; C. W. Woon et al. (1989) *J. Biol. Chem.* 264:5687–93]. However, it is not clear, in a particular cell type such as the cardiocyte which is replete in multiple $G_s$-coupled receptors and effectors including ion channels, that the availability of the G protein might be functionally limiting in the process of signal transduction. The present invention's measurements of adenylyl cyclase activity following catecholamine stimulation suggest that this latter possibility is not operative, at least under steady-state conditions.

b. Effect Of $G_{s\alpha}$ Overexpression On The Time Course Of Activation Of Cardiac Adenylyl Cyclase By GppNHp To assess further whether $G_{s\alpha}$ overexpression in the heart resulted in a more rapid stimulation of adenylyl cyclase, progress curves were constructed of cAMP production under GppNHp stimulation following the protocol described by L. Birmbaumer et al. [*J. Biol. Chem.* 255:3542–51 (1980)].

The same general procedure and reaction mixture [ie., 100 μl of a solution containing 20 mM HEPES (pH 8.0), 5 mM $MgCl_2$, 0.1 mM cAMP, 0.1 mM ATP and $^{32}$P-ATP (4 μCi per assay tube), 1 mM creatine phosphate, 8 μg/ml creatine phosphokinase, and 0.5 mM IBMX as an inhibitor of cAMP phosphodiesterase] previously described were used for this experiment. The reaction mixture was brought to a final incubation volume of 1.0 ml by the addition of GppNHp, thereby forming an "incubation mixture" with a final concentration of GppNHp of 111 μM.

The data points of the progress curves (FIGS. 8a and 8b) were obtained by withdrawing 100 μl aliquots from the incubation mixtures (ie., one control incubation mixture and one transgenic incubation mixture) at the indicated times (i.e., every 3 min), and stopping the reactions by adding the withdrawn aliquots to 100 μl of 2% SDS. Results of the progress curves were standardized by expressing them as a percentage of the maximal production of cAMP achieved at 30 min with 333 μM of GppNHp. The results reflect the mean±SD of 3 control and 3 transgenic mice.

Figure 8A:
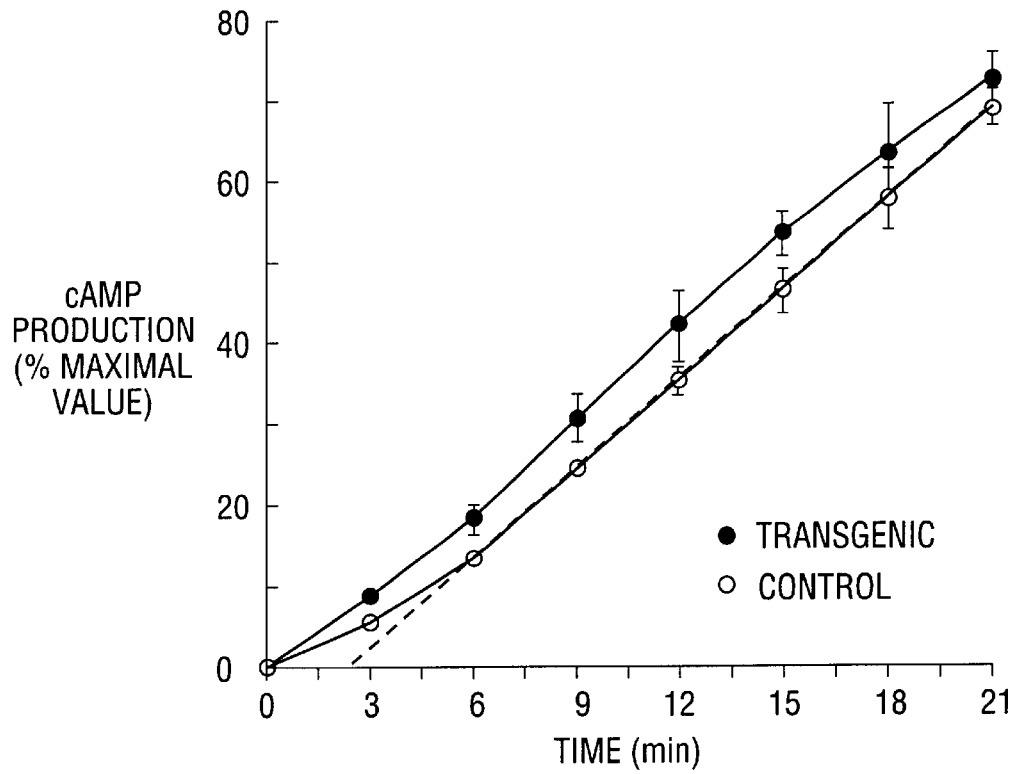
FIGS. 8A and 8B depict time-courses of activation of cardiac adenylyl cyclase by 111 μM of GppNHp in transgenic and control mice.

Steady-state slopes of cardiac adenylyl cyclase activity were calculated from 12 to 21 minutes, over which activity was constantly linear (FIG. 8a). With a concentration of 111 μM of GppNHp in the reaction mixture, the steady-state slopes of cardiac adenylyl cyclase activity were similar between 3 transgenic and 3 control mice (line 39) (FIG. 8a). However, as shown in FIG. 8a, there is a greater initial lag period necessary for GppNHp to exert its stimulatory effect in cardiac membranes from control mice (open circles) than in cardiac membranes from transgenic mice (solid circles). Initial slopes were estimated by calculation of the regression line forced to pass through the origin between 0 and 9 min. The significance of this regression line was always checked.

Figure 8B:
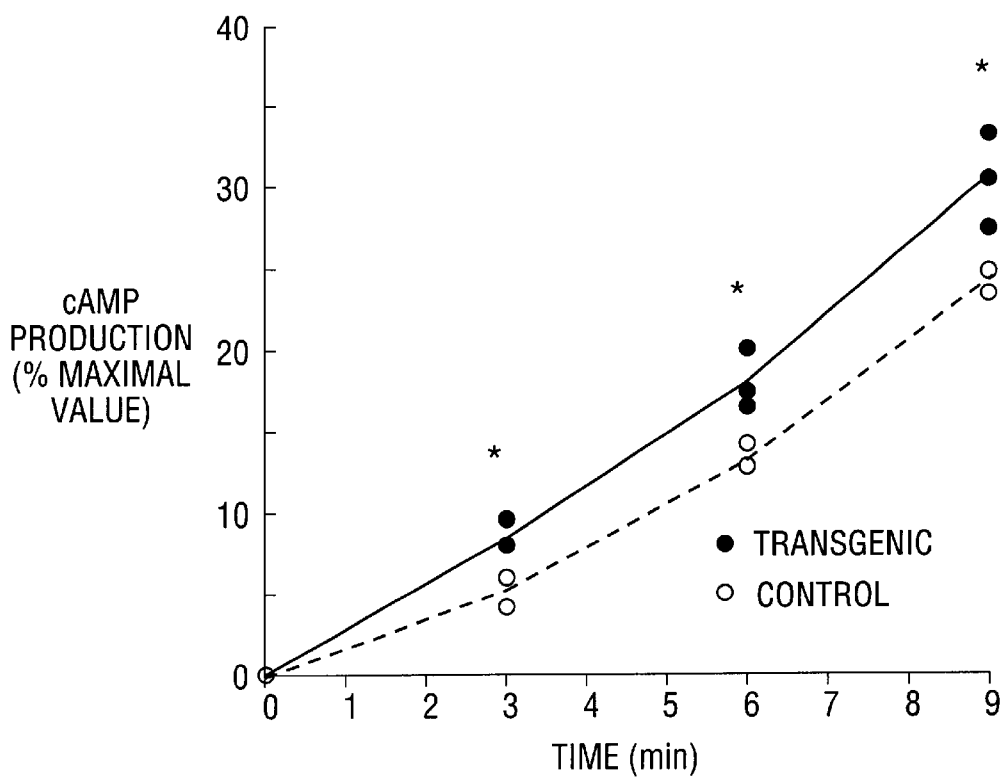

FIG. 8b emphasizes the greater lag period necessary in control mice for GppNHp to exert its stimulatory effect. That is, there was a significantly higher production of cAMP in transgenic mice as compared to control mice at 3, 6 and 9 min; indeed, the presence of the (*) above the time points indicates that there was a statistically significant difference between the transgenic mice and the control mice.

When plotted as a function of GppNHp concentration, steady-state activities, as indicated above, were similar between transgenic and control mice, with an apparent $K_a$ value of 0.15 μM in both cases. This $K_a$ value is within the 0.05-to-0.25 μM range previously described in rat liver under the same conditions. [L. Birmbaumer et al. (1980) *J. Biol. Chem.* 255:3542–51]. This lack of difference between transgenic and control mice suggests that under steady-state conditions, the number of GppNHp-bound $G_{s\alpha}$-adenylyl cyclase complexes in the heart is limited by the availability of the adenylyl cyclase, irrespective of the amount of GppNHp-bound $G_{s\alpha}$.

Moreover, as presented above, there was a significantly higher production of cAMP in transgenic mice as compared to control mice at the early time points. This finding of enhanced rate of adenylyl cyclase activation can be understood in the following context. A variety of data have previously shown that the rate of exchange of GDP for GTP at the G protein is rate-limiting in the activation of adenylyl cyclase, as shown in the following equation:

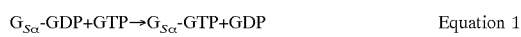

$$G_{s\alpha}\text{-GDP}+\text{GTP} \rightarrow G_{s\alpha}\text{-GTP}+\text{GDP} \qquad \text{Equation 1}$$

Overexpression of $G_{s\alpha}$ would therefore generate more $G_{s\alpha}$-GDP, and thus more $G_{s\alpha}$-GTP by a simple mass action effect (as exemplified by Equation 1), leading to an enhancement in the rate of catalytic activation. Similarly, the increased amount of $G_{s\alpha}$-GDP in the transgenic mice is reflected in the increase in the relative number of β-adrenergic receptors binding agonist with high affinity, i.e., increased ternary complex formation in the transgenic mice. The above data indicate that a relatively small change in the content of $G_{s\alpha}$ protein can impact receptor-$G_s$ coupling and the rate of adenylyl cyclase activation in the heart. Under steady-state conditions, maximal adenylyl cyclase activation remains unchanged in transgenic mice as compared to controls, suggesting that maximal catalytic activity is, indeed, limited by the availability of the adenylyl cyclase enzyme itself.

c. Effect Of Varying The Concentration Of GppNHp On Initial And Steady-State Production Of cAMP The experiment described in the previous section determined the effect of $G_{s\alpha}$ overexpression on the time course of activation of cardiac adenylyl cyclase by GppNHp. In that experiment, the reaction mixture was brought to a final concentration of GppNHp of 111 μM in a final incubation volume of 1.0 ml. The experiment described hereafter was performed in order to determine the effect of varying the concentration of GppNHp on initial and steady-state production of cAMP.

The same general procedure and reaction mixture [i.e., 100 μl of a solution containing 20 mM HEPES (pH 8.0), 5 mM $MgCl_2$, 0.1 mM cAMP, 0.1 mM ATP and $^{32}$P-ATP (4 μCi per assay tube), 1 mM creatine phosphate, 8 μg/ml creatine phosphokinase, and 0.5 mM IBMX as an inhibitor of cAMP phosphodiesterase] previously described were used for this experiment. As in the previous section, the reaction mixture was brought to a final incubation volume of 1.0 ml by the addition of GppNHp; however, in this experiment, progress curves were constructed over a range of final GppNHp concentrations (0.017 to 333 μM).

FIGS. 9a–d depict progress curves comparing initial and steady-state slopes of cardiac adenylyl cyclase activity in three transgenic (line 39) and three control mice using the different concentrations of GppNHp. Results of the progress curves were standardized by expressing the rate of cAMP production as a function of GppNHp concentration. The rate of cAMP production (% maximal production per minute) was calculated by dividing either the steady state or the initial slope of cAMP production by the amount of maximal cAMP production achieved with 333 μM GppNHp for 30 minutes. Steady-state (12 to 21 min) and initial (0 to 9 min) slopes were calculated for control mice (open circles or squares) and transgenic mice (solid circles or squares) and plotted as a function of GppNHp concentration. The results are expressed as mean±SD.

Figure 9A:
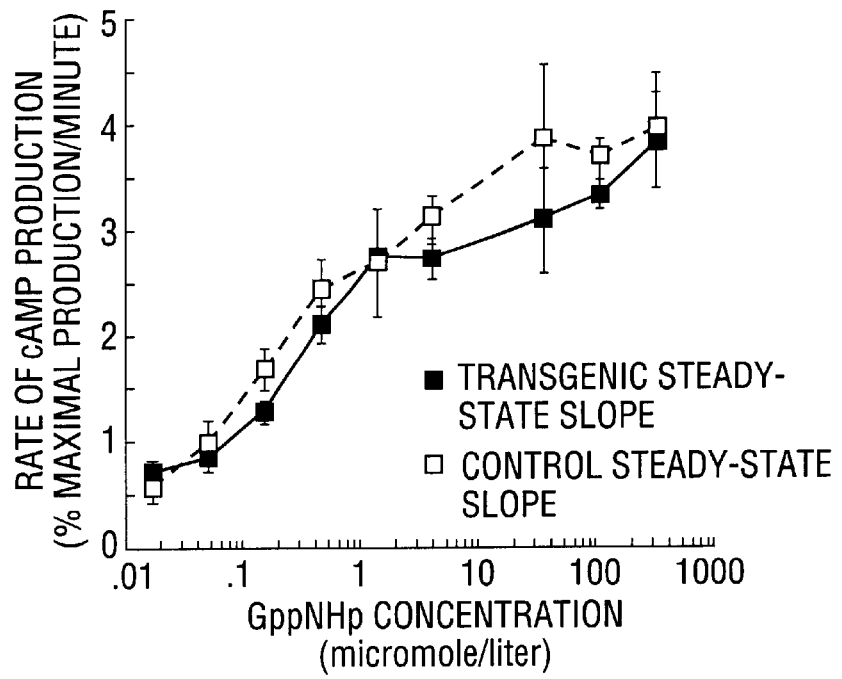
FIGS. 9A–9D depict comparisons of initial and steady-state slopes of cardiac adenylyl cyclase activity in transgenic and control mice, using different concentrations of GppNHp.
Figure 9B:
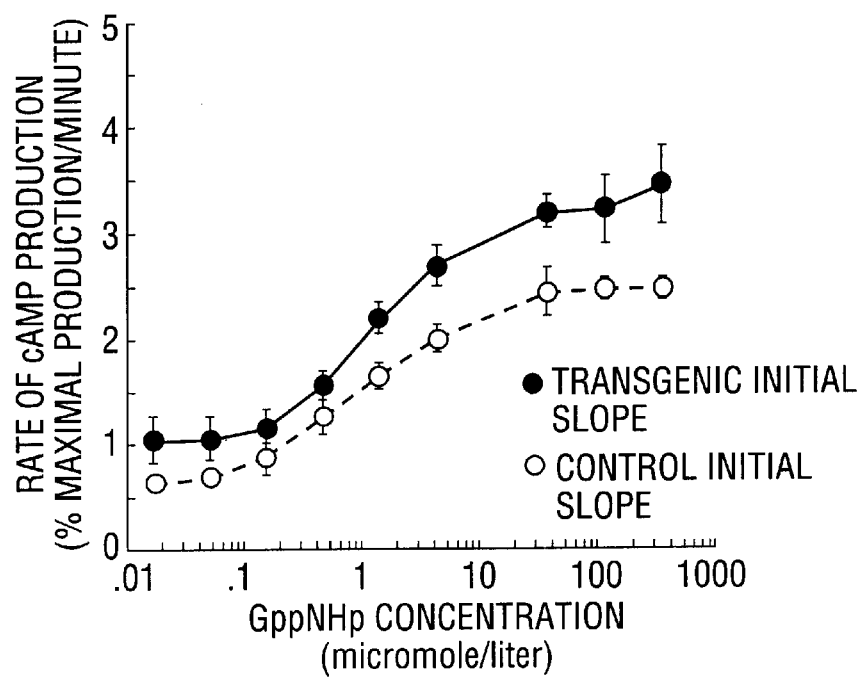
Figure 9C:
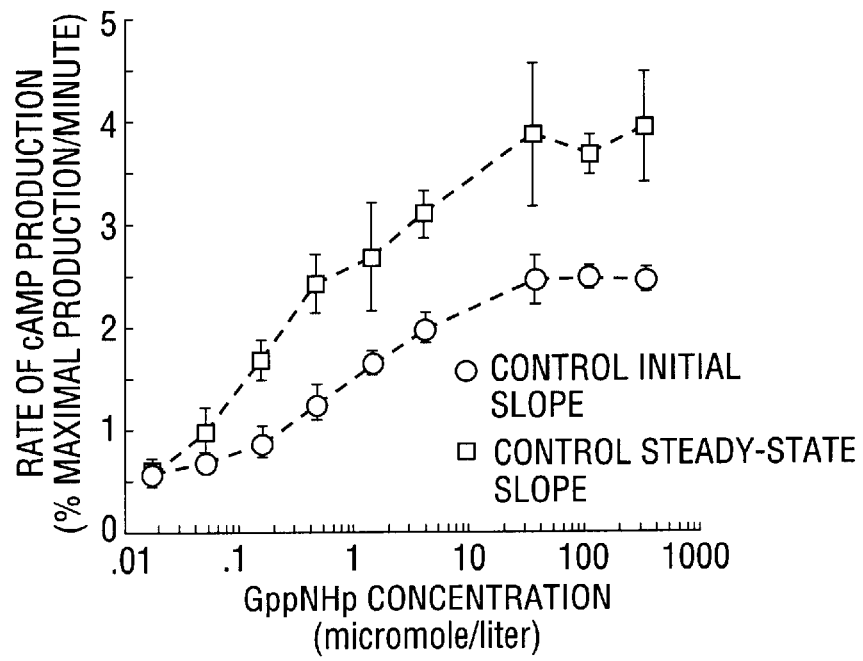
Figure 9D:
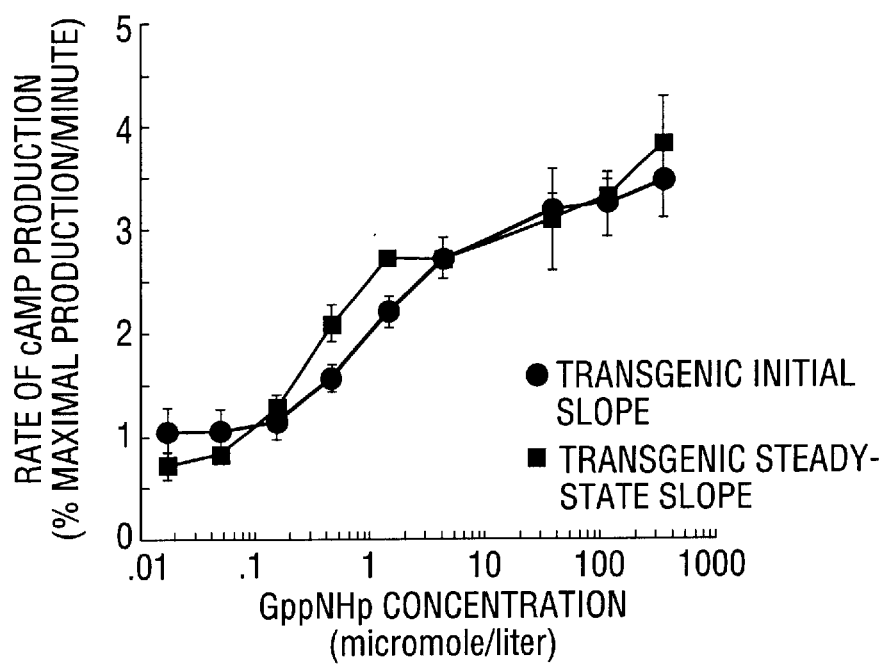

FIG. 9a compares steady-state slopes between transgenic and control mice. The results show that varying the concentration of GppNHp exerted the same effect on the steady-state production of cAMP in both populations of mice. FIG. 9b compares initial slopes between transgenic and control mice. In contrast to the steady-state slopes, the initial slopes significantly differed between transgenic and control mice, independently of the concentration of GppNHp that was used. FIG. 9c compares initial and steady-state slopes in control mice; the initial slope was significantly lower in control animals (FIG. 9, left lower), reflecting the existence of a lag period in the progress curve. Finally, FIG. 9d compares initial and steady-state slopes in transgenic mice. In contrast to the control mice, the initial slope was similar to the steady-state slope, reflecting a disappearance or decrease in the lag period, independent of the concentration of GppNHp that was used.

The results of this experiment using a range of GppNHp concentrations confirm the results obtained using a fixed concentration (111 $\mu$M) of GppNHp. More specifically, the steady-state slopes of cardiac adenylyl cyclase activity were similar between the transgenic and control mice, whereas the initial slopes differed significantly, the control animals exhibiting a lag period.

EXAMPLE 6

Effect of $G_{S\alpha}$ Overexpression on Cardiac Beta-Adrenergic Receptor Agonist Binding The previous example was concerned with the effect of $G_{S\alpha}$ overexpression directly on adenylyl cyclase activity. In contrast, this example is directed at the effect of $G_{S\alpha}$ overexpression on cardiac $\beta$-adrenergic receptor agonist binding.

Competitive inhibition agonist binding curves were constructed by the methods described by K. Kiuchi et al. (1993) *J. Clin. Invest.* 91:907–14. Specifically, $\beta$-adrenergic receptor agonist binding studies were conducted using 85 $\mu$l of the crude sarcolemma, 25 $\mu$l of $^{125}$I-cyanopindolol (0.07 nM), 25 $\mu$l of isoproterenol ($10^{-9}$ to $5 \times 10^{-4}$ M) with 22 concentrations of isoproterenol, and 15 $\mu$l of Tris buffer. Assays were performed in duplicate, incubated at 37° C. for 40 min, terminated by rapid filtration on GF/C filters (Millipore), and counted in a gamma counter for 1 min (Beckman). The binding data were analyzed by the LIGAND program. [P. J. Munson and D. Rodbard (1980) *Anal. Biochem.* 107:220–39]. In the computer analysis, the F test was used to compare the best fit for the ligand binding competition data. The best fit, two-site versus one-site, was determined by the p value for the F test. When the data were best fit to a single low-affinity site, the number of receptors in the high-affinity state was set to zero.

The isoproterenol competitive inhibition binding curves for the control and transgenic animals were fitted to a two-site model, i.e., a high affinity site ($K_H$) and a low affinity site ($K_L$). The average percentages of $\beta$-adrenergic receptors binding agonist with high affinity and low affinity are shown in Table 1; in Table 1, significant differences (p<0.05) between the control group and the transgenic group are represented by an (*) symbol. The relative number of high-affinity sites was significantly greater in transgenic than in control mice. Eighty percent of the total binding was specific binding.

TABLE 1

Agonist Binding Studies

| Isoproterenol binding affinity (nM) | Control (n = 10) | Transgenic (n = 9) |
|---|---|---|
| $K_H$ | 6.3 ± 2.0 | 20.0 ± 8.8 |
| $K_L$ | 376 ± 158 | 956 ± 672 |
| High-affinity receptor sites (%) | 55 ± 4 | 73 ± 7* |
| Low-affinity receptor sites (%) | 45 ± 4 | 27 ± 7* |

EXAMPLE 7

Physiological Studies of Responses to Isoproterenol and Norepinephrine

Prior examples have addressed, among other things, steady-state cardiac adenylyl cyclase activity stimulated by isoproterenol and the effect of $G_{S\alpha}$ overexpression on cardiac $\beta$-adrenergic receptor agonist binding. In contrast, this example is directed specifically at the heart's physiological responses to isoproterenol and norepinephrine.

a. Methodology

Five transgenic mice (10.3±0.2 months old) and five wild type/control mice (10.3±0.2 months old; from the same genetic background as the transgenic mice) of either sex (each group had 3 males and 1 female) were bred as described previously. [A. A. Alousi et al. (1991) *FASEB J.* 5:2300–03]. Four of five animals from the transgenic and the control groups were used for the isoproterenol studies (i.e., animals 1–4 from each group) and for the norepinephrine studies (i.e., animals 2–5 from each group). Thus, three animals from each group were common to both isoproterenol and norepinephrine studies, one animal from each group was only used for isoproterenol studies, and one animal from each group was only used for norepinephrine studies.

At least one day prior to initiation of the study, PE10 tubing (Clay Adams) was inserted into each animal's right jugular vein under a dissecting microscope; the catheter was tunneled subcutaneously to the animal's back, where it exited the animal's body. After determination of body weight, mice were anesthetized with ketamine (0.065 mg/g body weight), acepromazine (0.002 mg/g body weight), and xylazine (0.013 mg/g body weight) injected intraperitoneally. The mice were allowed to breathe spontaneously. Thereafter, the chests of the mice were shaved, and the mice were positioned prone on a warmed saline bag as support. The saline bag was attached to a warming pad (Deltaphase Isothermal Pad, Braintree, Mass.) to keep temperature constant at 37° C. [B. D. Hoit et al. (1995) *Circ Res.* 77:632–37].

Electrocardiographic leads were attached to each limb using needle electrodes (Grass Instruments). Echocardiography was performed by using an Interspec Apogee X-200 ultrasonograph (Interspec-ATL). A dynamically-focused 9 MHz annular array transducer was applied from below, using the saline bag as a standoff. The heart was first imaged in the 2-dimensional mode in the parasternal long-axis and short axis views. The short axis views, which included papillary muscles, were generally used to position the M-mode cursor perpendicular to the ventricular septum and LV posterior wall.

Studies were recorded on one-half inch S-VHS videotape (Sony Corporation, Tokyo, Japan), and freeze-frames were printed on a Sony Color Printer (UP-5200, Sony Corporation). The ECG was printed on the ultrasonograph for heart rate measurement. The images were scanned into a Macintosh IICi computer (Apple Computer) and digitized at 300 pixels/inch. Gray-scale equalization was made using the Photoshop program (Adobe Photoshop, Adobe Systems Corporation, California), and the images were imported into NIH-Image Program (NIH, Bethesda, Md.) for measurement. Using the transducer and the technique described in the preceding paragraph, M-mode measurements of left ventricular internal dimension (LVID) were made from more than 3 beats and averaged, using the leading edge-to-leading edge convention adopted by the American Society of Echocardiography. [D. J. Sahn et al. (1978) Circ. 58:1072–83]. End-diastolic measurements were taken at the time of the apparent maximal LV diastolic dimension, while end-systolic measurements were made at the time of the most anterior systolic excursion of the posterior wall. Left ventricular percent fractional shortening (LVFS) was calculated as follows: LVFS=[(LVIDd-LVIDs)/LVIDd]×100. Left ventricular ejection fraction was calculated by the cubed method as follows: LVEF=[(LVIDd)$^3$-(LVIDs)$^3$]/LVIDd$^3$.

M-mode echocardiographic measurements of the left ventricle were performed at baseline, and during intravenous infusion of isoproterenol. In control mice, infusions were at 0.01 μg/kg/min, 0.02 μg/kg/min, and 0.04 μg/kg/min for 5 minutes each in succession, using a micro syringe (Hamilton Microliter Syringes, Hamilton Company, Nevada) and a Harvard Infusion Pump (Harvard Apparatus, Inc.). In transgenic mice, infusions were at 0.005 μg/kg/min, 0.01 μg/kg/min, 0.02 μg/kg/min; the lower dose (0.005 μg/kg/min) was infused due to the enhanced response of the transgenic mice to isoproterenol (see Table 2, infra). The total amount of the infusion volume was less than 100 μl in each mouse. At least three days before the isoproterenol infusion, each mouse received an infusion of saline as control to insure that the volume of infusion alone did not contribute to enhanced ventricular performance.

At least one week after the isoproterenol infusion, a similar protocol was performed involving intravenous norepinephrine. Specifically, infusions at 0.1 μg/kg/min, 0.2 μg/kg/min and 0.4 μg/kg/min were used in control mice. The 0.1 μg/kg/min and 0.2 μg/kg/min doses were also used in transgenic mice, but a lower dose (0.05 μg/kg/min) was infused in transgenic mice rather than the higher does (0.4 μg/kg/min) used in the control mice. The difference in dosing regimen was due to the fact that preliminary experiments had indicated that the transgenic mice responded with a positive effect on left ventricular function at a lower dose than the control mice; the control mice did not respond at all to the lowest doses and the transgenic mice reached the top of the dose-response curve, ie., nearly 100% ejection fraction, at a lower dose than the control mice. Thus, the lowest dose was only examined in the transgenic mice and the highest dose was only examined in the control mice.

In this example (and in Example 8 that follows), all data were reported as mean±standard error. Comparisons between transgenic and control mice were made using Student's t-test for group data. The dose-response curves were analyzed by one-way ANOVA for repeated measurements. If the ANOVA demonstrated significant overall differences, individual comparisons between baseline and the responses to each dose were made by analysis of contrasts. This was done instead of other tests since the repeated-measures data are not independent at dose levels, but rather are correlated (data are from the same animals). Analysis of contrasts involves comparison of the means of selected levels of a factor or a combination of factors when there is a specific question about the effects of a subset of the levels of factors in the experiment. As was the case in the preceding examples, $p<0.05$ was taken as the minimal level of significance.

b. Response To Isoproterenol

Figure 10A:
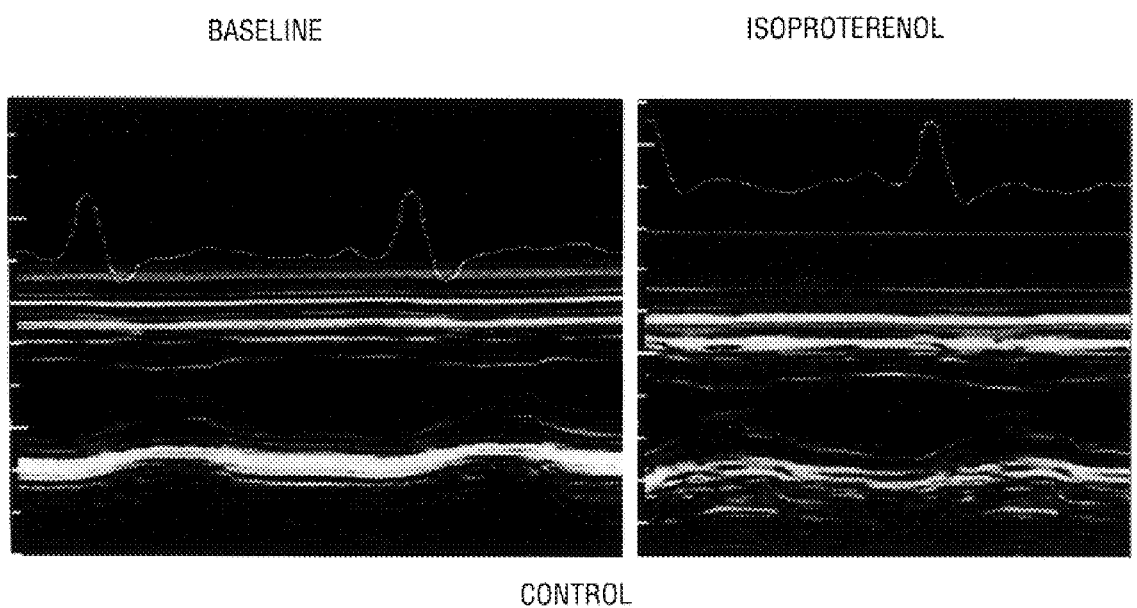
FIGS. 10A and 10B are echocardiographic recordings in response to isoproterenol 0.02 μg/kg/min in a representative (i) control mouse (FIG. 10A) and (ii) transgenic mouse (FIG. 10B).
Figure 10B:
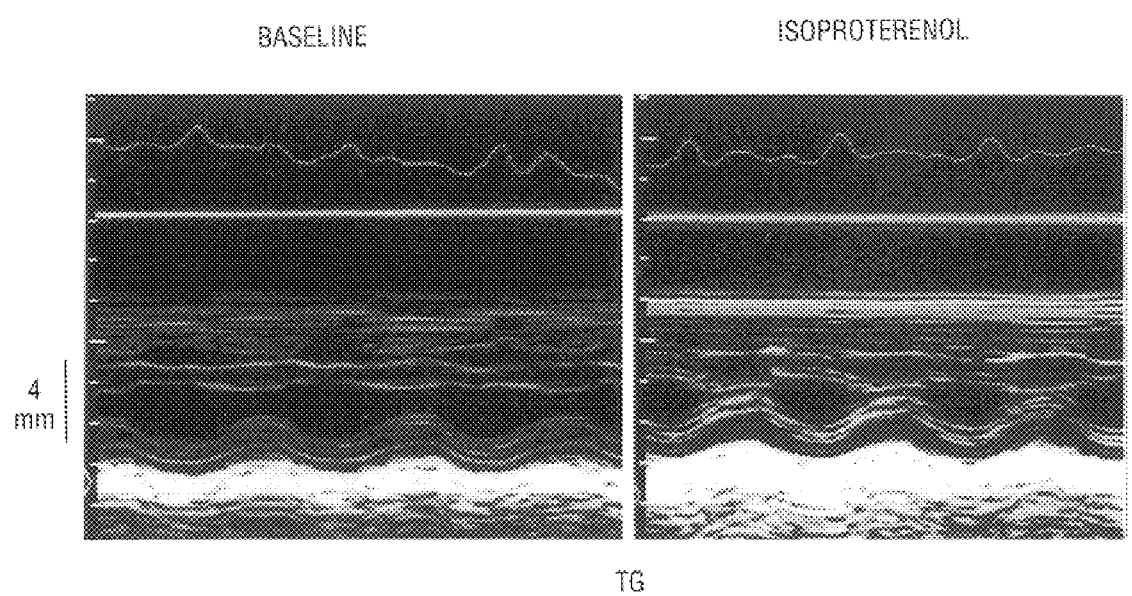

Responses to isoproterenol in control mice and in transgenic mice are summarized in Table 2. In addition, FIGS. 10a and 10b illustrate echocardiographic recordings in response to isoproterenol 0.02 μg/kg/min in a control mouse (FIG. 10a) and a transgenic mouse (FIG. 10b); those figures are representative of the echocardiographic recordings of the entire group of control and transgenic mice studied.

In Table 2, significant differences ($p<0.05$) between the control group and the transgenic group are represented by an (*) symbol listed with the appropriate data for the transgenic mouse. The (†) symbol indicates significant differences ($p<0.05$) within a group (i.e., control or transgenic) between a response value and the baseline value. In Table 3, the designation "ID" refers to internal dimension, and the designation "TG" refers to transgenic.

As summarized in Table 2, both the baseline heart rate and the chronotropic responses to increasing doses of isoproterenol were greater in transgenic mice than in control mice. In addition, left ventricular end-diastolic dimensions decreased dose-dependently in both groups. Contractility was assessed by ejection fraction (calculated from the distance between the ventricular septum and the left ventricular posterior wall at end-diastole and end-systole) in response to an isoproterenol infusion of 0.02 μg/kg/min. As indicated in Table 2, contractility was greater in transgenic mice than in control mice.

TABLE 2

Effects Of Isoproterenol On Hemodynamics

| | Isoproterenol infusion (μg/kg/min) | | | | |
|---|---|---|---|---|---|
| | Baseline | 0.005 | 0.01 | 0.02 | 0.04 |
| Heart Rate (beats/min) | | | | | |
| Control (n = 4) | 212 ± 18 | | 213 ± 16 | 236 ± 8 | 289 ± 18† |
| TG (n = 4) | 364 ± 9* | 369 ± 12 | 389 ± 10* | 433 ± 38*† | |
| LVID (mm) | | | | | |
| end-disatole | | | | | |
| Control (n = 4) | 3.9 ± 0.1 | | 4.0 ± 0.1 | 3.9 ± 0.1 | 3.6 ± 0.1† |
| TG (n = 4) | 3.6 ± 0.2 | 3.5 ± 0.3 | 3.4 ± 0.2* | 3.1 ± 0.1*† | |

TABLE 2-continued

Effects Of Isoproterenol On Hemodynamics

| | Isoproterenol infusion (µg/kg/min) | | | | |
|---|---|---|---|---|---|
| | Baseline | 0.005 | 0.01 | 0.02 | 0.04 |
| end-systole | | | | | |
| Control (n = 4) | 2.5 ± 0.1 | | 2.4 ± 0.0 | 2.0 ± 0.1† | 1.3 ± 0.2† |
| TG (n = 4) | 2.2 ± 0.1* | 2.0 ± 0.1 | 1.6 ± 0.1*† | 1.0 ± 0.1† | |
| Fractional Shortening (%) | | | | | |
| Control (n = 4) | 36.2 ± 1.8 | | 38.5 ± 1.1 | 48.3 ± 3.2† | 62.8 ± 5.7† |
| TG (n = 4) | 39.6 ± 3.2 | 42.5 ± 3.2 | 53.5 ± 3.5*† | 67.9 ± 4.2*† | |
| Ejection Fraction (%) | | | | | |
| Control (n = 4) | 73.9 ± 2.2 | | 76.7 ± 1.2 † | 85.8 ± 1.6† | 94.1 ± 2.0† |
| TG (n = 4) | 77.5 ± 3.4 | 80.6 ± 3.2 | 89.5 ± 2.6*† | 96.3 ± 1.3*† | |

Figure 11A:
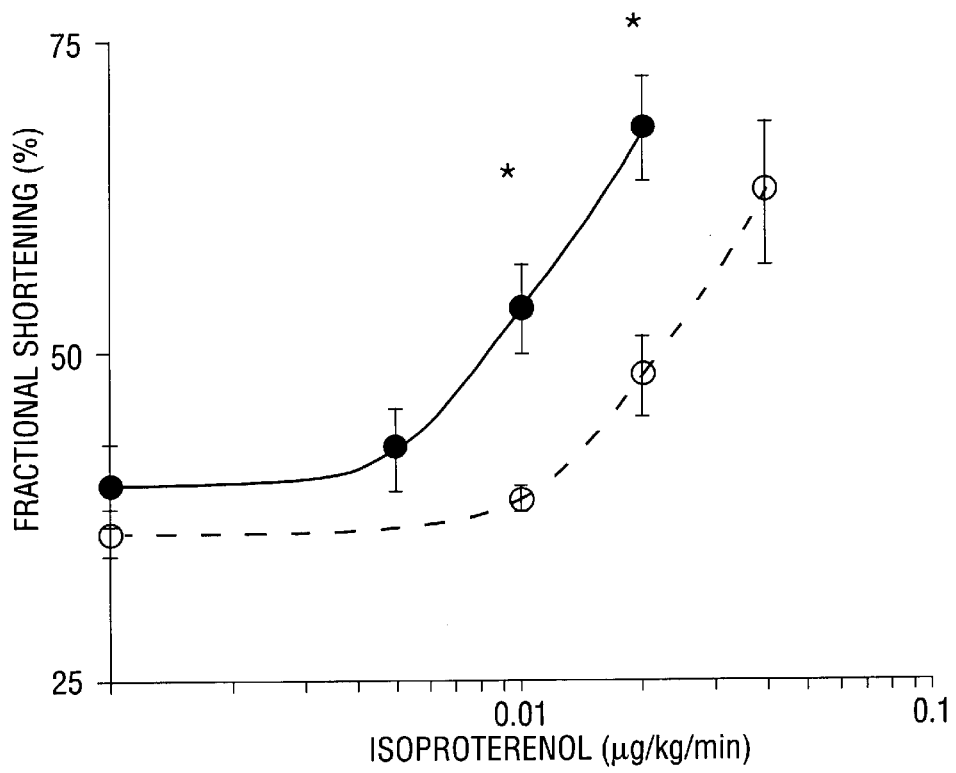
FIGS. 11A–C. 11A is a graph showing the relationship of left ventricular fractional shortening in response to graded infusion of isoproterenol (i.e.,a dose-response curve).
Figure 11B:
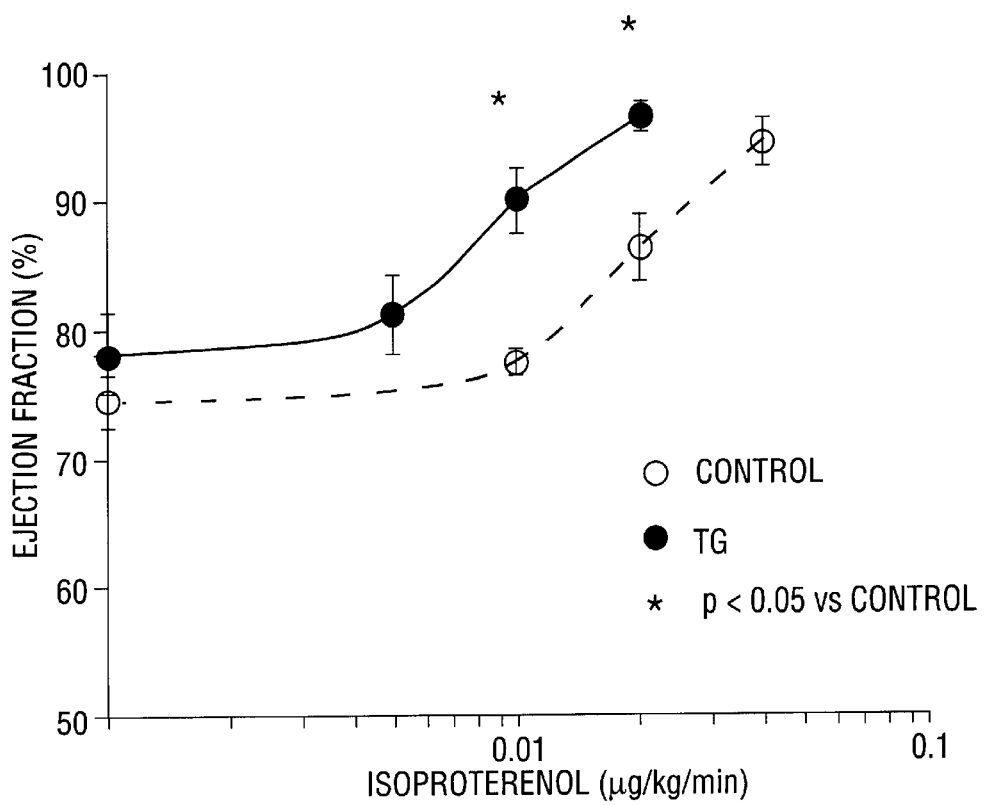

Baseline levels of left ventricular fractional shortening and ejection fraction were not significantly different. However, isoproterenol infusion produced significantly greater increases in both fractional shortening and ejection fraction in transgenic mice (FIGS. 11a and 11b, respectively). FIGS. 11a and 11b are graphs showing the dose-response relationship of left ventricular fractional shortening and ejection fraction, respectively, in response to graded infusion of isoproterenol. Referring to those figures, there was a leftward shift in the dose-response relationship for both left ventricular ejection fraction and fractional shortening (each point represents the mean±S.E.M). In other words, a lower dose of isoproterenol was required in transgenic mice than in control mice to achieve the same response (i.e., left ventricular ejection fraction and fractional shortening).

The effect of isoproterenol (and norepinephrine, described below) was examined in transgenic and control mice with heart rate constant in order to evaluate whether the higher heart rates in the mice with overexpressed $G_{S\alpha}$ were having an influence on the experimental results. Three transgenic mice (10.8±1.8 months old) and three wild-type control mice (10.7±1.7 months old) were studied with an acutely implanted 1.8 Fr Millar micromanometer (Millar Instruments, Houston, Tex.) and with heart rate held constant. After administration of the anesthetic regiment described above [ketamine (0.065 mg/g body weight), acepromazine (0.002 mg/g body weight), and xylazine (0.013 mg/g body weight) injected intraperitoneally], a 25 gauge needle was inserted into the left ventricle through the chest wall. The needle was utilized for electrical pacing (Grass Stimulator, model SD9, Grass Instruments) and a 1.8 Fr Millar was connected for measurement of left ventricular pressure. The left ventricular pressure signal was differentiated (frequency response of 700 Hz) for calculation of contractility (LV dP/dt; change in left ventricular pressure over time). Measurements of left ventricular pressure, left ventricular contractility, and heart rate were recorded on a multichannel type recorder and played back on a multichannel oscillograph (mfrs/model #s for recorder and oscillograph).

Figure 11C:
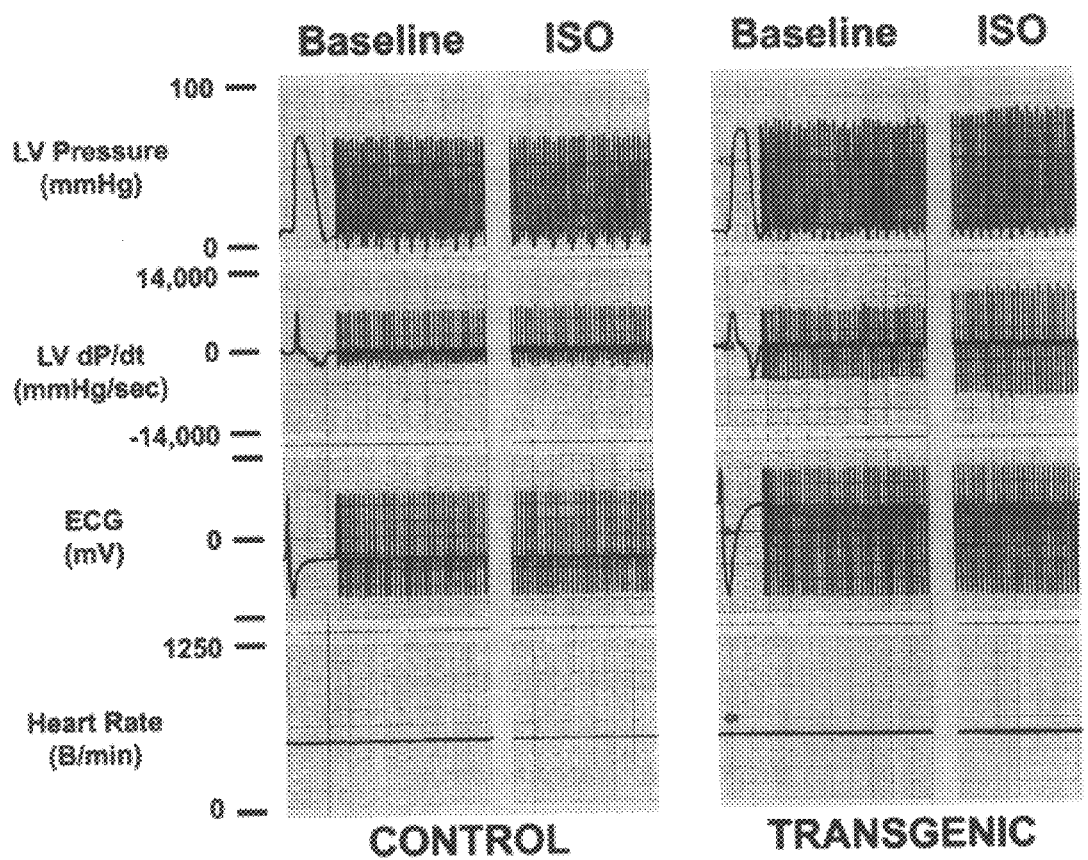

In the three wild-type control mice with heart rate held constant (8.0±0.0 Hz), isoproterenol (0.02 µg/kg/min) increased left ventricular contractility (LV dP/dt) by 13±2% from a baseline of 6923±281 mm Hg/sec. This was significantly less (p<0.01) than that observed in the three transgenic mice with heart rate held constant (9.0–0.6 Hz), where the same isoproterenol regimen increased contractility by 33±2% from a similar baseline to that of the wild-type control mice. FIG. 11c depicts an example of phasic waveformns of left ventricular pressure (LV Pressure; mm Hg), left ventricular contractility (LV dP/dt; mm Hg/sec), electrocardiograms (mV), and heart rate (beats/minute) in a wild-type control (left) and a transgenic mouse (right) in response to isoproterenol (ISO). With heart rate constant, isoproterenol induced a greater effect on contractility in the transgenic mouse.

c. Response To Norepinephrine

Responses to norepinephrine in control and transgenic mice are summarized in Table 3. In Table 3, significant differences (p<0.05) between the control group and the transgenic group are represented by an (*) symbol listed with the appropriate data for the transgenic mouse. The (†) symbol indicates significant differences (p<0.05) within a group (i.e., control or transgenic) between a response value and the baseline value. In Table 3, the designation "ID" refers to internal dimension, and the designation "TG" refers to transgenic.

The data in Table 3 indicate that at baseline, the heart rate in transgenic mice was significantly greater than in control mice. The heart rate remained significantly greater in transgenic mice upon norepinephrine infusion at 0.1 µg/kg/min and 0.2 µg/kg/nin (the two infusion rates received by both groups of animals). However, norepinephrine had no significant chronotropic effect on either group (as indicated by the absence of the "†" symbol in the data directed at heart rate); this was most likely due to secondary reflex cardiac slowing induced by the rise in blood pressure. In contrast to isoproterenol, norepinephrine infusion had no effect on left ventricular end-diastolic dimensions in either the transgenic or the control group. However, similar to isoproterenol, norepinephrine produced significantly greater increases both in fractional shortening and ejection fraction in transgenic mice.

TABLE 3

Effects Of Norepinephrine On Hemodynamics

| | Norepinephrine Infusion (µg/kg/min) | | | | |
|---|---|---|---|---|---|
| | Baseline | 0.05 | 0.1 | 0.2 | 0.4 |
| Heart Rate (beats/min) | | | | | |
| Control (n = 4) | 246 ± 26 | | 241 ± 27 | 252 ± 33 | 272 ± 44 |
| TG (n = 4) | 321 ± 18* | 320 ± 13 | 322 ± 16* | 341 ± 18* | |
| LVID (mm) | | | | | |
| end-diastole | | | | | |
| Control (n = 4) | 4.0 ± 0.1 | | 4.0 ± 0.1 | 4.1 ± 0.1 | 4.0 ± 0.1 |
| TG (n = 4) | 3.7 ± 0.2 | 3.6 ± 0.1 | 3.6 ± 0.2* | 3.6 ± 0.1* | |
| end-systole | | | | | |
| Control (n = 4) | 2.6 ± 0.1 | | 2.4 ± 0.1 | 2.2 ± 0.1† | 1.7 ± 0.2† |
| TG (n = 4) | 2.4 ± 0.2 | 2.1 ± 0.1 | 1.7 ± 0.2*† | 1.5 ± 0.2*† | |
| Fractional Shortening (%) | | | | | |
| Control (n = 4) | 34.5 ± 2.4 | | 39.9 ± 0.5 | 47.0 ± 3.1† | 58.2 ± 3.9† |
| TG (n = 4) | 35.9 ± 3.2 | 41.9 ± 3.9 | 52.2 ± 4.8*† | 59.4 ± 4.1*† | |
| Ejection Fraction (%) | | | | | |
| Control (n = 4) | 71.6 ± 3.2 | | 78.3 ± 0.1 | 84.8 ± 2.6† | 92.3 ± 2.0† |
| TG (n = 4) | 73.2 ± 4.0 | 79.8 ± 4.0 | 88.3 ± 3.8*† | 92.8 ± 2.1*† | |

Finally, the effect of norepinephrine on left ventricular contractility was assessed, using the methodology described above for isoproterenol, in order to evaluate whether the higher heart rates in the mice with overexpressed $G_{s\alpha}$ were having an influence on the experimental results. In three wild-type control mice with heart rate held constant (6.0±0.0 Hz), norepinephrine (0.1 µg/kg/min) increased left ventricular contractility (LV dP/dt) by 28±4% from a baseline of 7292±461 mm Hg/sec. This was significantly less (p<0.05) than that observed in the three transgenic mice with heart rate held constant (8.3±1.2 Hz), where the same norepinephrine regimen increased contractility by 65±8% from a similar baseline to that of the wild-type control mice. The fact that norepinephrine significantly increased left ventricular function (i.e., ejection fraction and fractional shortening) but did not increase heart in the transgenic mice indicates that the inotropic action of sympathomimetic amines can be dissociated from their chronotropic actions.

d. Augmentation Of Responsiveness To Sympathomimetic Amines By $G_{s\alpha}$ Overexpression As indicated by the data presented above, responsiveness to sympathomimetic amines is augmented in mice with $G_{s\alpha}$ overexpression (i.e., transgenic mice). With intravenous infusion of either isoproterenol or norepinephrine, ventricular systolic performance, as reflected by ejection fraction and fractional shortening of the left ventricle, was enhanced in the transgenic mice. Because these sympathomimetic amines exert opposing effects on preload and afterload, these changes in indices of ventricular performance cannot be ascribed to loading conditions, but rather to a true change in the inotropic state.

When relating the in vivo physiological consequences of cardiac $G_{s\alpha}$ overexpression to the molecular and biochemical alterations in vitro, the experimental results raise an interesting conundrum. As previously presented, adenylyl cyclase at steady-state is not altered whether activated with agonist plus GTP, GppNHp, NaF or forskolin; that finding is consistent with a scenario in which the sarcolemmal content of the catalyst itself has not changed. Nevertheless, in vivo, the transgenic hearts hyper-respond to catecholamines as compared to the control (wild-type) hearts. Moreover, unpublished observations indicate that the activation of more distal effector pathways such as the L-type $Ca^{2+}$ channel, known to be regulated by cAMP-dependent protein kinase A, was markedly enhanced in transgenic cardiocytes. [Y-F Xioa et al., "Enhancement of cardiac $G_{s\alpha}$ and chloride-currents in transgenic mice overexpressing $G_{s\alpha}$ (Abstract) Circ. (1995) (In press)]. Thus, there are apparently contradictory observations.

Several hypotheses have been suggested to reconcile these observations. First, it is possible that these enhanced physiological responses are transduced via $G_{s\alpha}$ but not through adenylyl cyclase activation. There has been preliminary evidence that $G_{s\alpha}$ can directly modulate the activity of other effector pathways. [H. Kume et al. (1992) Proc. Natl. Acad. Sci. USA 89:11051–55; H-Y Wang et al. (1992) Nature 358:334–37; M. Bomsel and K. E. Mostov K. E. (1993) J. Biol. Chem. 268:25824–35]. Nevertheless, the enhanced inotropic and chronotropic responses seen in the results presented above are characteristic, if not classical, responses to enhanced cAMP generation.

A more attractive hypothesis is that steady-state cAMP measurements do not accurately reflect the activity of the β-adrenergic signaling pathway in the heart. Instead, the heart responds on a second-to-second basis to changing levels of norepinephrine released and removed at the synaptic terminal as the organism moves, changes posture, eats or becomes excited. In responding to these continuously changing demands, the heart operates on the steep portion of the receptor occupancy curve, with the precise position of operation continuously changing; as a result, one cannot conduct steady-state measurements in vitro to accurately mirror in vivo signaling activity. Biochemical measurements of the myocardial β-adrenergic receptor-$G_s$-adenylyl cyclase pathway made in vitro are thereby limited in that they may not accurately reflect the activity of this pathway in the dynamic range in which it operates in vivo. It is exactly in this framework that the increased $G_{s\alpha}$ levels in the transgenic cardiocytes are likely exerting their effect by allowing small changes in β-adrenergic receptor occupancy to signal the catalyst to activate more rapidly. Static measurements of second messenger activity, whether cAMP or $Ca^{2+}$, cannot capture the dynamic nature of these activities, particularly in the intact innervated heart, which responds to changing neural activity on a time frame measured in seconds.

Although the experiments in this example were carried out with exogenously administered sympathomimetic amines, one can readily extrapolate to the in vivo situation where sympathetic tone fluctuates on a moment-to-moment basis. Assuming that similar augmented inotropic and chronotropic effects would be observed with physiological increases in adrenergic drive, this transgenic model thus becomes useful for the study of the cardiac effects of chronic adrenergic hyperactivity.

EXAMPLE 8

Pathological Studies of Responses to Isoproterenol and Norepinephrine

The prior example was directed at the heart's physiological responses to isoproterenol and norepinephrine. In turn, this example presents the results of pathological studies of sympathomimetic amine-stimulated hearts.

a. Methodology

Separate groups of 9 transgenic mice (16.0±0.8 months old) and 8 wild-type mice (16.4≅0.8 months old; from the same genetic background as the transgenic mice) were used for this experiment. As was the situation in Example 7, all numerical data were reported as mean±standard error .

All mice were anesthetized with intraperitoneal sodium pentobarbital (Anpro Corp., Arcadia, Calif.). Thereafter, the animals' chests were opened and their hearts were either (i) removed and dissected fresh or (ii) perfused at 90 mm Hg with a brief saline wash followed by glutaraldehyde (administered via a 21 gauge trocar needle inserted directly into the left ventricular apex); these procedures are described further in the next paragraph. The hearts were then dissected to remove the atria and the right ventricular free wall, and each portion was weighed.

The hearts from the dissected animals (4 transgenic and 4 control mice) were fixed by immersion in 10% phosphate-buffered formalin. Formalin-fixed tissues were dehydrated, embedded in paraffin, and sectioned at 6 $\mu$m thickness. The sections were then stained with hematoxylin and eosin and Gomori aldehyde fuchsin trichrome. Formalin-fixed sections were also stained with picric acid sirius red. The hearts from the perfused animals (5 transgenic and 4 control mice) were treated by perfusion fixation with 2% phosphate-buffered glutaraldehyde. Glutaraldehyde perfusion-fixed tissues were dehydrated and embedded in Spurr epoxy resin and in glycol methacrylate, sectioned at 1 $\mu$m thickness. The Spurr epoxy resin sections were then stained with toluidine blue and the glycol methacrylate sections with methylene blue-basic fuchsin for light microscopic examination. The methacrylate sections were also stained with silver-gold (Accustain Silver stain, Sigma Diagnostics) to stain the basement membrane in order to outline cardiac myocytes for cross-sectional area measurement.

Myocyte cross-sectional area was measured from video prints of silver-stained 1 $\mu$m thick methacrylate sections of subendocardial and subepicardial regions of the left ventricle. Cross-sectional slides were defined as suitable for video prints if they had nearly circular capillary cross-sectional vessel profiles, and circular-to-oval myocyte cross-sectional profiles. No correction for oblique sectioning of the cardiac tissue was made. Video prints (1100×final magnification) were used to trace the outline of 40–130 myocytes in each region (i.e., subendocardial and subepicardial) using a sonic digitizer (Graf/Bar, Science Accessories, Southport, Conn.). The sonic digitizer pen was placed on the object to trace and moved completely around the outline to end at the starting point. The area was computed to an accuracy of 1.0 mm, as determined by ultrasonic precision.

Myocyte cross-sectional area was determined using specially-developed computer programs. Briefly, data collected from a single preparation, from multiple, fields, are transferred to a Lotus 1-2-3 worksheet for calculation of means, standard deviations, and standard error of the means. The mean area was first calculated for each region in each animal, and then the group mean was calculated for each region (i.e., subendocardial and subepicardial) and group (i.e., transgenic and wild-type control).

Myocardial connective tissue was quantitatively analyzed on a single cross-section of left ventricle and septum obtained mid-distance from the left ventricle's base to its apex. This cross-section was embedded in paraffin and stained with picric acid sirius red, which stains collagen specifically. Images were obtained from a video monitor and a Dage CCD72 monochrome video camera attached to an Olympus AHT microscope (Olympus Corp., Japan), using a 1×objective and a green (550 nm) filter at a final video screen magnification of 30×. The images were analyzed using a video-based Image-1 image analysis software Universal Imaging Corporation, West Chester, Pa.), which rapidly measures highlighted objects. The entire inner (subendocardial) and outer (subepicardial) halves of the left ventricle were traced and analyzed separately for volume percentage of collagen. Areas measured in each region ranged from 2.5–10 $mm^2$.

b. Pathological Findings

Figure 12A:
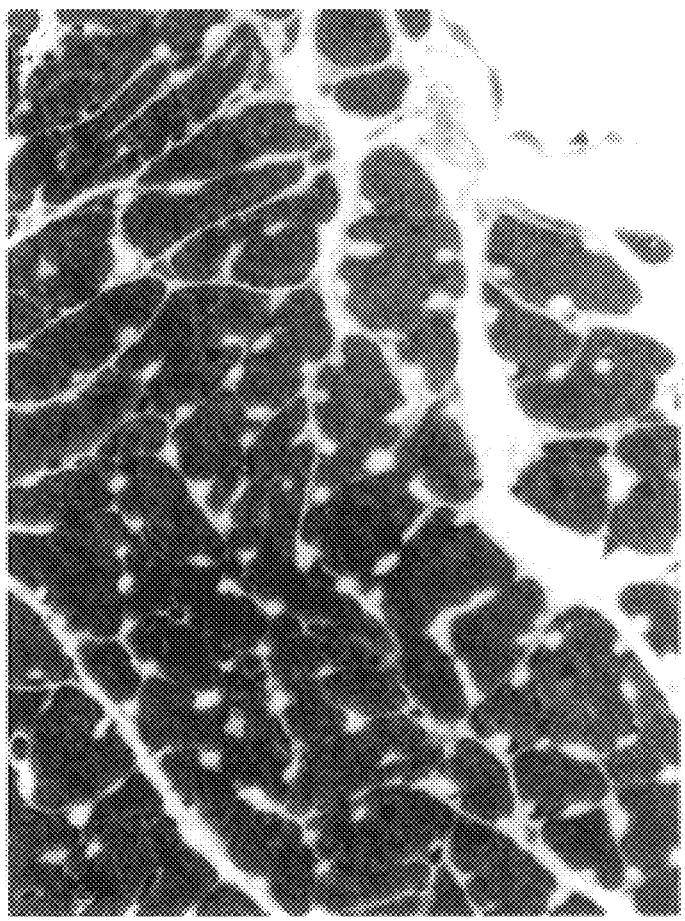
FIGS. 12 A–B. 12A is a photomicrograph of a toluidine blue-stained section of left ventricular subendocardium of 19-month old control mice.
FIG. 12B is a photomicrograph of a toluidine blue-stained section of left ventricular subendocardiuni of 15-month old transgenic mice. The photomicrographs depicted in FIGS. 12A and 12B were taken at the same magnification.
Figure 12B:
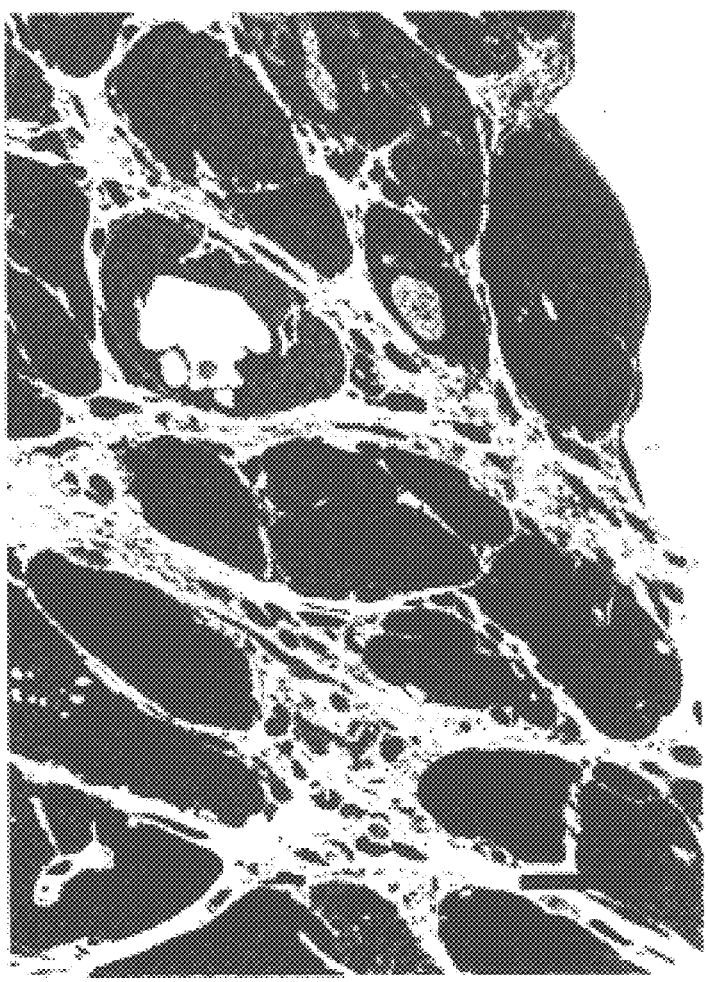

Pathological analysis involved both qualitative and quantitative assessment. The photomicrographs depicted in FIGS. 12a and 12b, each taken at the same magnification, were part of the qualitative assessment. FIG. 12a is a stained section of left ventricular subendocardium of 19-month old control mice, and FIG. 12b is a stained section of left ventricular subendocardium of 15-month old transgenic mice. The sections depicted in FIGS. 12a and 12b (bar=25 $\mu$m) are glutaraldehyde-fixed tissues that were dehydrated and embedded in Spurr epoxy resin; the samples were then sectioned at 1 $\mu$m thickness, and the sections were stained with toluidine blue. There is marked cellular hypertrophy in the transgenic mouse (FIG. 12b), with some large pale cells containing vacuoles, indicating degeneration. In addition, interstitial connective tissue is increased in the transgenic mouse compared to the section from the control mouse. Overall, six of the 9 transgenic mice had moderate to severe multifocal areas of mature replacement fibrosis and interstitial fibrosis throughout the left ventricle and septum, most severe in the subendocardium (see FIG. 12b).

Figure 13A:
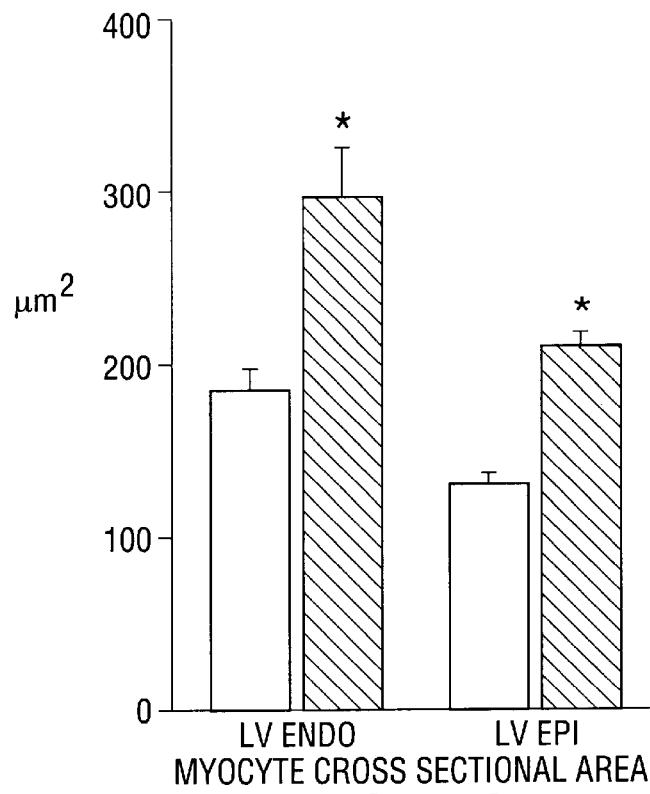
FIGS. 13A–B. 13A is a bar graph showing quantitative evaluation of myocyte cross-sectional area.

Quantitative assessment revealed that there was a marked increase in the cross-sectional area of cardiac myocytes, especially in the subendocardial half of the left ventricular myocardium (FIG. 13a). FIG. 13a is a bar graph showing quantitative evaluation of myocyte cross-sectional area. In FIG. 13a, the open bars represent control mice, whereas the hatched bars represent transgenic mice; comparison of myocyte cross-sectional area in left ventricular subendocardium and in left ventricular subepicardium are depicted on the left and right portions of FIG. 13a, respectively.

Figure 13B:
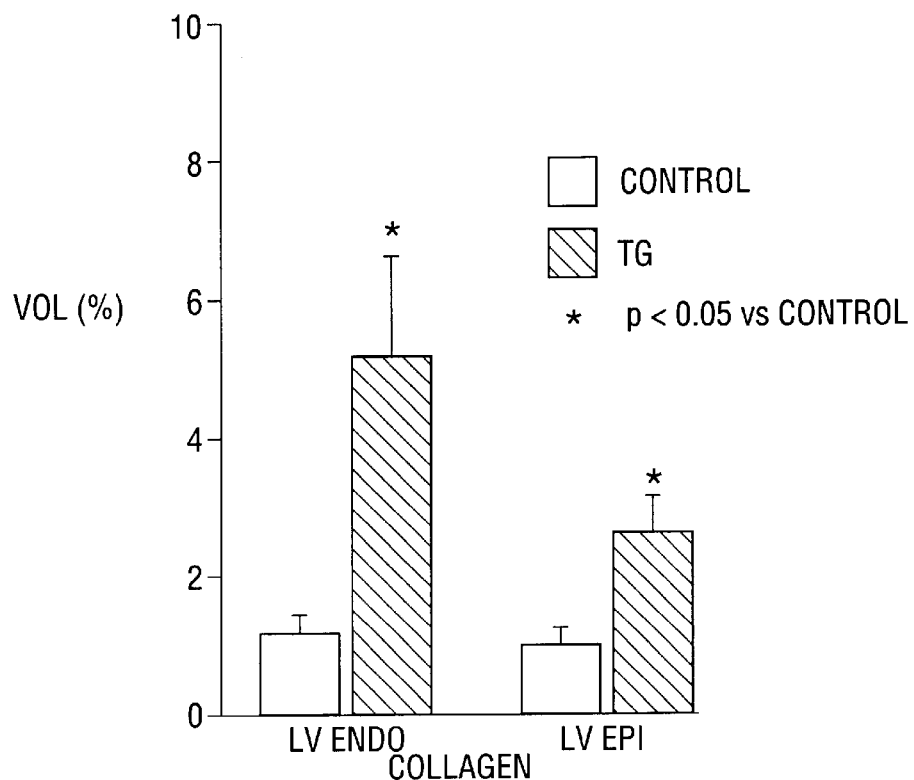

In the subendocardial regions, particularly in areas adjacent to focal fibrosis, there was extreme variability in myocyte cross sectional area; some myocytes were smaller than normal, suggesting atrophy, and others had very large cross-sectional areas, some exceeding 500 $\mu$m$^2$. Quantitative evaluation of myocardial fibrosis revealed a significant increase in volume percent collagen for the entire group of transgenic mice compared to control mice, most prominently in the subendocardium (FIG. 13b). FIG. 13b is a bar graph showing quantitative evaluation of myocardial fibrosis. In FIG. 13b, the open bars represent control mice, whereas the hatched bars represent transgenic mice; comparison of volume percent collagen in left ventricular subendocardium and in left ventricular subepicardium are depicted on the left and right portions of FIG. 13b, respectively.

Table 4 reports the body weights of the mice as well as the weights of some of the parts of their hearts. The following abbreviations are used in Table 4: BW (body weight), HW (heart weight), LV+S W (left ventricle plus septum weight), RVW (right ventricle weight), TG (transgenic mice). Analysis of the data in FIG. 4 indicates that the myocyte hypertrophy in transgenic mice was apparently offset by the cellular degeneration and necrosis. For, heart weight, even normalized to body weight, was not significantly elevated in the transgenic mice (5.07±0.34) as compared to controls (4.66±0.30).

evidence of myocardial cellular degeneration and extensive increases in fibrosis as reflected by the increased collagen, most prominent in the subendocardium. Significantly increased myocyte size confirmed the existence of hypertrophy in both the subepicardium and subendocardium, but again more prominently in the subendocardium where wall stresses are higher and the impact of reduced coronary reserve is greater. [L. Hitinger et al. (1995) Circ. 92:978–86].

Importantly, the hypertrophic process was not evident on gross morphology. Apparently, the cellular degeneration and myocyte loss, evident on light microscopy and corroborated by electron microscopy, offset the expected increased total heart weight, that should have been observed with myocyte hypertrophy. The hypertrophy presumably resulted as a compensatory response to the increases in cardiac work imposed by the chronically enhanced endogenous adrenergic function. With cellular degeneration and myocyte loss, cardiac function might be expected to decline and provide a further stimulus to hypertrophy in the remaining cardiocytes, potentially through local application of the Frank-Starling mechanism. In addition, a direct role of $G_{s\alpha}$ on myocardial growth cannot be ruled out.

EXAMPLE 9

Testing of Animals and Screening of Chemical Compounds

In order to screen for effective chemical compounds, transgenic mice having a phenotype that is consistent with

TABLE 4

Body Weights And Heart Weights

|  | BW g | HW mg | LV + SW mg | RVW mg | RW/BW mg/g | LV + SW/BW mg/g | RVW/BW mg/g |
|---|---|---|---|---|---|---|---|
| Control (n = 6) | 34.6 ± 2.9 | 160 ± 14 | 118 ± 12 | 31 ± 3 | 4.66 ± 0.30 | 3.42 ± 0.26 | 0.91 ± 0.04 |
| TG (n = 9) | 37.0 ± 2.7 | 187 ± 18 | 136 ± 12 | 31 ± 3 | 5.07 ± 0.34 | 3.69 ± 0.23 | 0.83 ± 0.05 |

Transmission electron microscopy (Phillips 400) revealed individual cells with myofibrillar disorganization and loss, small mitochondria, increased lipofuscin and bizarre nuclei, indicative of myocyte degeneration and atrophy in the transgenic mice (results not shown). Qualitative histological data from transgenic mice with ages similar to those in which physiology was examined indicated the presence of hypertrophied myocytes in transgenic mice 7 months old (n=3) and hypertrophied myocytes plus fibrosis in transgenic mice 10 months old (n=2) and 12 months old (n=5). Finally, 32% of the transgenic mice died of heart failure at about 11.5 months of age.

The transgenic mice develop a dilated cardiomyopathy as they age which becomes apparent at about 16 months of age.

c. Discussion Of The Histological Finding In Older Transgenic Mice

It is possible that the cumulative effects of increased endogenous sympathetic stimulation secondary to the overexpression of $G_{s\alpha}$ might result in catecholamine-induced myocardial injury. For example, a prior study in rats with infusion of isoproterenol for several weeks demonstrated myocardial hypertrophy with cellular necrosis and replacement fibrosis. [I. J. Benjamin et al. (1989) Circ. Res. 65:657–70]. Similarly, another prior study in mice with chronic isoproterenol administration demonstrated enhanced hypertrophic responses. [R. J. Robbins and J. L. Swain (1992) Am. J. Physiol. 262:H590–H597]. Indeed, in the experiments of the present invention, there was clear the syndrome of human heart failure are employed. When cardiac function in the $G_{s\alpha}$ tansgenic mice has been assessed at a relatively young age it is found to be relatively normal. However, with aging, the animals clearly develop significant pathologic changes in the myocardium; by about 16 months of age the mice display a dilated cardiomyopathy. Therefore, the physiologic function of the heart in older animals is analyzed, and the neurohormonal status of the animals is assessed. The myocardial status of animals used to screen for effective chemical compounds is examined directly by examining histological sections of the heart of treated versus control animals.

Regarding neurohormonal status, a variety of reflex mechanisms occur in human heart failure to deal with the perceived reduction in effective cardiac output. Specifically, the sympathetic nervous system is activated, the renin-angiotensin-aldosterone system is activated, and vasopressin levels can be elevated. Therefore, plasma will be obtained from the transgenic animals as they age to determine whether catecholamine levels increase; similarly, plasma renin activity and aldosterone and vasopressin levels will be measured and compared to the transgenic animals' normal litter mates. Simultaneously, since it is known that a cardinal sign of a failing heart is depletion of myocardial catecholamine content, that parameter will also be measured as the animals age and will be correlated with pathologic and physiologic findings. Finally, both serum and ventricular pro-atrial natriuretic factor levels, known to increase as the heart hypertrophies and failures ensues, will be measured.

Thereafter, a variety of drug interventions known to improve the syndrome of human heart failure will be assessed to determine whether, in fact, they have an effect on the physiology of the transgenic animals as well as on their survival. Along these lines, a variety of antagonists known to block the neurohormonal pathways discussed above will be assessed. Specifically, β-blockers will be employed since it has already been demonstrated that as a result of $G_{s\alpha}$ overexpression, the transgenic animals are hyperresponsive to catecholamines. Over the life of these animals, it is postulated that this hyperresponsiveness is directly deleterious to the myocardium.

The β-blockers will be administered to the animals by either implanting a subcutaneous pump or placing the drug directly into the animal's feed. The transgenic animals will be administered a variety of β-antagonists, including $β_1$-specific receptor antagonists (e.g., atenolol), $β_2$-specific receptor antagonists (e.g., butoxarnine), as well as non-specific antagonists (e.g., propranolol and nadolol). For at least a six-month period, starting no later than six months of age and probably continuing through adult life, several parameters will be measured in both the treated and control animals. It should be noted that four groups will be examined: wild-type untreated versus wild-type treated and transgenic untreated versus transgenic treated. As previously indicated, a number of categories will be assessed, including life span and myocardial function over time using echocardiographic techniques.

At sacrifice or death of the animals, the status of the myocardium as to replacement fibrosis, myocyte death and its underlying mechanism (particularly as mediated by apoptosis) will be examined. Moreover, gross factors such as heart weight, left and right ventricular weights, and atrial size will be analyzed. A more focused analysis of certain animals will also be carried out to determine whether myocyte hypertrophy has occurred even without an absolute increase in heart weight; this finding has been observed in transgenic mice, and it is possible that an intervention such as β-blockade might prevent some of these findings.

A similar analysis will be undertaken with drugs known to block other neurohormonal mediators, such as the ACE inhibitors. As with the β-blockers, the ACE inhibitors could either be administered through a subcutaneous pump or directly in the food; experimentation will be conducted to determine which is the most efficacious manner of administration. A sufficient dose of an ACE inhibitor will be employed to block all angiotensin II production as assessed by a plasma assay. In addition, steps will be taken to attempt to ensure generation of a maximal increase in plasma renin activity which would be expected to occur as a reflex response to ACE inhibition.

As previously alluded to, a variety of newer agents will be employed which block putatively important mediators of vascular dysfunction associated with the heart failure syndrome. Such agents include endothelin antagonists which are now available (e.g., BQ 123 and Bosentan). As with the β-blockers, there are specific endothelin A and B receptor antagonists as well as non-specific receptor antagonists. Similarly, angiotensin II receptor antagonists and vasopressin receptor antagonists will also be assessed.

There are also a variety of other drugs which work via different mechanisms of action that have been tied to effects on human heart failure, including antioxidants. The underlying data to support these hypotheses, however, are much weaker. Carvedilol is an example of a β-blocker with antioxidant effects as well as a vasodilative effect; it has been shown to have a clinical effect in human heart failure. Carvedilol will be tested in an attempt to demonstrate that it not only produces a positive effect on longevity, but also on the physiologic function of the heart in these animals as they age, as well as on the pathologic changes that occur over time.

EXAMPLE 10

Generation of Transgenic Pigs

In order to provide a large animal model of heart failure, transgenic pigs containing the $G_{s\alpha}$ transgene were generated. The larger heart size of animals such as pigs or rabbits provide enhanced physiological and biochemical data. In particular, the rate of coronary blood flow is comparable in pigs and humans.

The $G_{s\alpha}$ transgene is introduced into the fertilized eggs of pigs to generate transgenic pigs. Prepuberal (6 to 8 months of age) Landrace, Duroc, Hampshire and PBZ 991 gilts weighing 85 to 100 kg are used as embryo donors. Five days before hormonal treatment, gilts showing estrus are eliminated. The gilts are superovulated by administration of 1500 IU pregnant mare serum gonadotropin (PMSG; Biowet-Drwalew, Poland) followed by 1000 IU human chorionic gonadotropin (hCG; Biomed, Lublin, Poland). Gilts are mated twice with proven boars 24 and 36 hours after hCG injection.

Embryos are recovered from slaughtered gilts 48 to 52 hours after the hCG injection. Zygotes and 2-cell embryos are flushed from the removed oviducts with 50 ml/oviduct of phosphate buffered saline containing albumin (PBS-albumin supplemented medium) and the number of ovulations is determined.

Eggs at the pronuclear stage are injected after centrifugation in a microcentrifuge with the linearized $G_{s\alpha}$ transgene as described in Example 2. The microinjected embryos are transferred to recipients. Genornic DNA is isolated from piglets born to the recipient sows and Southern blot analysis is conducted as described in Example 2 to determine which piglets are transgenic. Transgenic founder animals are bred with normal pigs to establish independent germ lines. The transgenic pigs are characterized as described in Examples 3–8 above. Transgenic pigs which have a phenotype consistent with the syndrome of heart failure are used to screen for compounds which provide beneficial effects on the physiology and survival of the pigs as described in Example 9 above.

From the above, it should be evident that the heart model of the present invention provides for transgenic animals and methods for testing the usefulness of chemical compounds in treating heart failure.

We claim:

1. A transgenic mouse from 8 to 16.8 months of age displaying manifestations of heart failure selected from the group consisting of (a) shortness of breath relative to a control mouse, (b) pitting edema relative to a control mouse, (c) an enlarged tender liver relative to a control mouse, (d) engorged neck veins relative to a control mouse, and (e) pulmonary rates relative to a control mouse, wherein the genome of said mouse comprises a murine α-myosin heavy chain gene promoter operably linked to a nucleotide sequence encoding $G_{s\alpha}$ MRNA, and expresses $G_{s\alpha}$ mRNA in its cardiac tissue at a level that is at least 3-fold higher than in cardiac tissue of a control mouse.

2. The mouse of claim 1, wherein said mouse does not overexpress said $G_{s\alpha}$ mRNA in the skeletal muscle of said mouse.

3. The mouse of claim 1, wherein sail manifestations of heart failure are further selected from the group consisting of (f) increased myocardial contractility in the presence of a sympathomimetic amine selected from the group consisting of isoproterenol and norepinephrine relative to a control mouse, (g) increased heart rate in the presence of isoproterenol relative to a control mouse, (h) increased collagen volume in subendocardium relative to a control mouse, and (i) increased baseline heart rate relative to a control mouse.

4. The mouse of claim 1, wherein said manifestations of heart failure are further selected from the group consisting of (f) increased myocardial contractility in the presence of a sympathomimetic amine selected from the group consisting of isoproterenol and norepinephrine relative to a control mouse, (g) increased heart rate in the presence of isoproterenol relative to a control mouse, (h) increased collagen volume in subendocardium relative to a control mouse, and (i) increased baseline heart rate relative to a control mouse.

5. The mouse of claim 1, wherein said $G_{s\alpha}$ is selected from the group consisting of the short isoform of $G_{s\alpha}$ and the long isoform of $G_{s\alpha}$.

6. A transgenic mouse from 8 to 16.8 months of age displaying manifestations of heart failure selected from the group consisting of (a) shortness of breath relative to a control mouse, (b) pitting edema relative to a control mouse, (c) an enlarged tender liver relative to a control mouse, (d) engorged neck veins relative to a control mouse, and (e) pulmonary rates relative to a control mouse, wherein said mouse expresses $G_{s\alpha}$ mRNA, in its cardiac tissue at a level which is at least 3-fold higher than in cardiac tissue of a control mouse, wherein the genome of said mouse contains a murine α-myosin heavy chain gene promoter element operably linked to a nucleotide sequence encoding a $G_{s\alpha}$ protein.

7. The mouse of claim 6, wherein said $G_{s\alpha}$ is selected from the group consisting of the short isoform of $G_{s\alpha}$ and the long isoform of $G_{s\alpha}$.

8. A method for producing a transgenic mouse expressing $G_{s\alpha}$ mRNA in cardiac tissue, said method comprising:

a) introducing into an embryonal cell of a mouse a murine α-myosin heavy chain gene promoter operably linked to a nucleotide sequence encoding a $G_{s\alpha}$ protein;

b) transplanting the transgenic embryonal target cell formed thereby into a recipient female parent; and c) identifying at least one transgenic offspring containing said nucleotide sequence in said offspring's genome, wherein at from 8 to 16.8 months of age said offspring displays manifestations of heart failure selected from the group consisting of (a) shortness of breath relative to a control mouse, (b) pitting edema relative to a control mouse, (c) an enlarged tender liver relative to a control mouse, (d) engorged neck veins relative to a control mouse, and (e) pulmonary rates relative to a control mouse, and expresses $G_{s\alpha}$ mRNA in its cardiac tissue at a level which is at least 3-fold higher than in cardiac tissue of a control offspring.

9. The method of claim 8 wherein said promoter is capable of directing the expression of said nucleotide sequence encoding a $G_{s\alpha}$ protein in a cardiac-specific manner.

10. The method of claim 9, wherein said offspring is further characterized by no overexpression of $G_{s\alpha}$ MRNA in skeletal muscle.

11. The method of claim 8, wherein said $G_{s\alpha}$ is selected from the group consisting of the short isoform of $G_{s\alpha}$ and the long isoform of $G_{s\alpha}$.

12. A method for producing a transgenic mouse expressing $G_{s\alpha}$ mRNA in cardiac tissue, said method comprising:

a) introducing into an embryonal cell of a mouse a murine α-myosin heavy chain gene promoter operably linked to a nucleotide sequence encoding a $G_{s\alpha}$ protein, wherein said promoter is capable of directing the expression of said nucleotide sequence encoding a $G_{s\alpha}$ protein in a cardiac-specific manner;

b) transplanting the transgenic embryonal target cell formed thereby into a recipient female parent; and c) identifying at least one transgenic offspring containing said nucleotide sequence in said offspring's genome, wherein at from 8 to 16.8 months of age said offspring displays manifestations of heart failure selected from the group consisting of (a) shortness of breath relative to a control mouse, (b) pitting edema relative to a control mouse, (c) an enlarged tender liver relative to a control mouse, (d) engorged neck veins relative to a control mouse, and (e) pulmonary rates relative to a control mouse, and expresses $G_{S\alpha}$ mRNA in its cardiac tissue at a level which is at least 3-fold higher than in cardiac tissue of a control offspring.

13. The method of claim 12, wherein said offspring is further characterized by no overexpression of $G_{S\alpha}$ mRNA in skeletal muscle.

14. The method of claim 12, wherein said $G_{S\alpha}$ is selected from the group consisting of the short isoform of $G_\alpha$ and the long isoform of $G_{S\alpha}$.

15. A method for screening compounds for the ability to prevent or treat the manifestations of heart failure in a mouse, comprising:

a) providing a transgenic mouse from 8 to 16.8 months of age displaying manifestations of heart failure selected from the group consisting of (a) shortness of breath relative to a control mouse, (b) pitting edema relative to a control mouse, (c) an enlarged tender liver relative to a control mouse, (d) engorged neck veins relative to a control mouse, and (e) pulmonary rates relative to a control mouse, wherein the genome of said mouse comprises a murine α-myosin heavy chain gene promoter operably linked to a nucleotide sequence encoding $G_{s\alpha}$ mRNA, and expresses $G_{s\alpha}$ mRNA in its cardiac tissue at a level which is at least 3-fold higher than in cardiac tissue of a control mouse;

b) administering a compound to said mouse; and c) measuring an improvement in the physiologic function of the heart of said mouse and thereby identifying a compound as therapeutic.

16. The method of claim 15, wherein said administration of said compound occurs prior to the onset of manifestations of heart failure.

17. The method of claim 15, wherein said administration of said compound occurs after the onset of manifestations of heart failure.

18. The method of claim 15, wherein said compound is a β-adrenergic receptor antagonist.

19. The method of claim 18, wherein said β-adrenergic receptor antagonist is selected from the group consisting of $β_1$-specific adrenergic receptor antagonists, $β_2$-specific adrenergic receptor antagonists, and non-selective β-adrenergic receptor antagonists.

20. The method of claim 15, wherein said compound is an angiotensin-converting enzyme inhibitor.

21. The method of claim 15, wherein said $G_{S\alpha}$ is selected from the group consisting of the short isoform of $G_{S\alpha}$ and the long isoform of $G_{S\alpha}$.

22. A transgenic mouse from 10.1 to 10.5 months of age displaying manifestations of heart failure selected from the group consisting of (a) shortness of breath relative to a control mouse, (b) pitting edema relative to a control mouse, (c) an enlarged tender liver relative to a control mouse, (d) engorged neck veins relative to a control mouse, and (e) pulmonary rates relative to a control mouse, wherein the genome of said mouse comprises a murine α-myosin heavy chain gene promoter operably linked to a nucleotide sequence encoding $G_{s\alpha}$ mRNA, and expresses $G_{s\alpha}$ mRNA in its cardiac tissue at a level that is at least 3-fold higher than in cardiac tissue of a control mouse.

23. The mouse of claim 22, wherein said $G_{S\alpha}$ is selected from the group consisting of the short isoform of $G_{S\alpha}$ and the long isoform of $G_{S\alpha}$.

24. A transgenic mouse from 8 to 16.8 months of age displaying manifestations of heart failure selected from the group consisting of (a) shortness of breath relative to a control mouse, (b) pitting edema relative to a control mouse, (c) an enlarged tender liver relative to a control mouse, (d) engorged neck veins relative to a control mouse, and (e) pulmonary rates relative to a control mouse, wherein the genome of said mouse comprises a rat α-myosin heavy chain gene promoter operably linked to a nucleotide sequence encoding the short isoform of $G_{s\alpha}$ mRNA, and expresses $G_{s\alpha}$ mRNA in its cardiac tissue at a level that is at least 3-fold higher than in cardiac tissue of a control mouse.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

CGGCAGCGGC CGTCAGCTCT CACCTGCCCT CG                                32